United States Patent [19]
Davis et al.

[11] Patent Number: 5,484,735
[45] Date of Patent: Jan. 16, 1996

[54] IMMUNOASSAY OF GLYCOSYLATED PROTEINS EMPLOYING ANTIBODY DIRECTED TO REDUCTIVELY GLYCOSYLATED N-TERMINAL AMINO ACIDS

[75] Inventors: Lyman E. Davis, Chicago; Byron E. Anderson, Morton Grove, both of Ill.

[73] Assignee: Northwestern University, Evanston, Ill.

[21] Appl. No.: 151,073

[22] Filed: Nov. 12, 1993

Related U.S. Application Data

[63] Continuation-in-part of Ser. No. 68,525, May 27, 1993, abandoned, which is a continuation of Ser. No. 397,781, Aug. 23, 1989, abandoned.

[51] Int. Cl.$^6$ .......................... G01N 33/53; G01N 33/542
[52] U.S. Cl. ...................... 436/548; 435/7.1; 435/7.9; 435/14; 435/240.27; 435/70.21; 436/536; 530/387.5; 530/387.9; 530/388.25; 530/389.3
[58] Field of Search .................. 435/7.1, 7.9, 14, 435/240.27, 70.21; 436/536, 548; 530/387.5, 387.9, 388.25, 389.3

[56] References Cited

U.S. PATENT DOCUMENTS

| | | | |
|---|---|---|---|
| 3,941,763 | 3/1976 | Sarantakis | 530/313 |
| 4,200,435 | 4/1980 | Stroupe et al. | 436/67 |
| 4,247,533 | 1/1981 | Cerami et al. | 436/542 |
| 4,255,385 | 3/1981 | Stroupe et al. | 436/67 |
| 4,268,270 | 5/1981 | Gabbay et al. | 436/67 |
| 4,269,605 | 5/1981 | Dean et al. | 436/67 |
| 4,349,352 | 9/1982 | Manning et al. | 436/67 |
| 4,371,374 | 2/1983 | Cerami et al. | 436/87 |
| 4,372,747 | 2/1983 | Gabbay et al. | 436/67 |
| 4,376,110 | 3/1983 | David et al. | 435/5 |
| 4,399,227 | 8/1983 | Niederau et al. | 436/67 |
| 4,423,034 | 12/1983 | Nakagawa et al. | 436/67 |
| 4,438,204 | 3/1984 | Deeg et al. | 436/67 |
| 4,478,744 | 10/1984 | Mezei et al. | 530/322 |
| 4,629,022 | 12/1986 | Dean | 180/69.22 |
| 4,629,692 | 12/1986 | Dean | 435/7.7 |
| 4,636,463 | 1/1987 | Altman et al. | 435/7.92 |
| 4,647,654 | 3/1987 | Knowles et al. | 530/326 |
| 4,649,122 | 3/1987 | Lee | 436/67 |
| 4,658,022 | 4/1987 | Knowles et al. | 530/402 |
| 4,727,036 | 2/1988 | Knowles et al. | 530/387.9 |
| 4,778,752 | 10/1988 | Curtiss et al. | 435/7.92 |
| 4,797,473 | 1/1989 | Tarsio et al. | 530/388.25 |
| 4,806,468 | 2/1989 | Wagner et al. | 435/7.1 |
| 4,810,391 | 3/1989 | Bruegger | 210/656 |
| 4,835,097 | 5/1989 | Saunders | 435/4 |
| 4,837,170 | 6/1989 | Ohe et al. | 436/548 |
| 4,861,728 | 8/1989 | Wagner | 436/501 |
| 4,868,130 | 9/1989 | Hargreaves | 436/526 |
| 4,876,188 | 10/1989 | Smith et al. | 435/7.25 |
| 4,879,036 | 11/1989 | Takahashi et al;. | 210/635 |
| 4,956,301 | 9/1990 | Ismail et al. | 436/87 |
| 5,071,767 | 12/1991 | Portenhauser et al. | 436/15 |
| 5,116,762 | 5/1992 | Vogt et al. | 436/15 |
| 5,149,633 | 9/1992 | Vogt et al. | 435/25 |
| 5,206,144 | 4/1993 | Zeuthen et al. | 435/7.25 |

FOREIGN PATENT DOCUMENTS

| | | |
|---|---|---|
| 0111211 | 6/1984 | European Pat. Off. . |
| 185870 | 7/1986 | European Pat. Off. . |
| 0201187 | 11/1986 | European Pat. Off. . |
| 3439610 | 4/1986 | Germany . |
| 61-172064 | 8/1986 | Japan . |
| 2-8743 | 1/1990 | Japan . |

OTHER PUBLICATIONS

Abraham et al., *J. Lab. Clin. Med.*, 102, 187 (1983).
Avrameas and Ternynck, *Immunochemistry*, 6, 53 (1969).
Bannon et al., *Clinical Chemistry*, 30, 485 (1984).
Berzofsky et al., *Biochemistry*, 15, 2113 (1976).
Broughton and Strong, *Clinical Chemistry*, 22, 726 (1976).
Brownles et al., *Diabetes*, 29, 1044 (1980).
Brownlee et al., *Ann. Int. Medicine*, 101, 527 (1984).
Bunn, *Diabetes*, 30, 613 (1981).
Bunn, *Amer. J. Med.*, 70, 325 (1981).
Cole et al., *Metabolism*, 27, 289 (1978).
Cully et al., *Recent Progress in Clinical Chemistry* (scientific presentation Sep. 1992).
Curtiss and Witzum, *Diabetes*, 34, 452 (1985).
Davis et al., *Fed. Proc.*, 42, 1872 (1983).
Davis et al., *Biochemistry International*, 10, 395 (1985).
Day et al., *J. Biol. Chem.*, 254, 595 (1979).
Dische et al., *Arch. Biochem. Biophys.*, 2, 169 (1949).
Ehrlich et al., *J. Immunology*, 131, 1906 (1983).
Fairbanks and Zimmerman, *Mayo Clin. Proc.*, 58, 770 (1983).
Friedman et al., *Int. J. Peptide Protein Res.*, 6, 183 (1974).
Friquet et al., *Molecular Immunology*, 21, 673 (1984).
Fujiwara et al., abstract of presentation at 31st Immunometric Assay Symposium, Nov. 14, 1993.

(List continued on next page.)

*Primary Examiner*—Toni R. Scheiner
*Attorney, Agent, or Firm*—Willian Brinks Hofer Gilson & Lione

[57] ABSTRACT

An immunoassay for a protein that is non-enzymatically glycosylated on the alpha amino group of its N-terminal amino acid, the immunoassay comprising: providing a sample containing the glycosylated protein; reacting the glycosylated protein with a reducing agent so that the sugar residue on the N-terminal amino acid is reduced; contacting the reduced glycosylated protein with an antibody directed to Glc-ol-X which is prepared by immunizing an animal with an immunogen of the formula (Glc-ol-X-L)$_n$-carrier; and detecting or quantitating the reduced glycosylated protein bound to the antibody. In the formula (Glc-ol-X-L)$_n$-carrier: X is the N-terminal amino acid of the glycosylated protein, except that X cannot be lysine; L is a bond or a linker group; Glc-ol is the reduced form of the sugar attached to X on the glycosylated protein, and Glc-ol is attached to the alpha amino group of X; the carrier is an immunogenic compound other than the glycosylated protein; and n is from 1 to the number of available coupling sites on the carrier. Also, the antibody, the immunogen, and methods of making them. Finally, a kit for quantitating a protein glycosylated on its N-terminal amino acid.

30 Claims, 25 Drawing Sheets

OTHER PUBLICATIONS

Furth, *New Scientist*, 3, 58 (1988).
Furth, *Analytical Biochemistry*, 175, 374 (1988).
Garlick and Mazer, *J. Biol. Chem.*, 258, 6142 (1983).
Go et al., *Clin. Chim. Acta,* 163, 63 (1987).
Goldstein, *New Engl. J. Med.,* 384 (1984).
Gould et al., *Ann. Clin. Biochem.,* 21, 16 (1984).
Hayashi and Makino, *Clin. Chim. Acta,* 149, 13 (1985).
Herold et al., *Ann. Clin. Lab. Science,* 13, 482 (1983).
Hjerten and Yang, *J. Chromatography,* 316, 301 (1984).
Javid et al., *Brit. J. Haemotology,* 38, 329 (1978).
Jovanovic and Peterson, *Am J. Med.,* 70, 331 (1981).
Kemp et al., *J. Pediatrics,* 105, 394 (1984).
Kennedy and Merimee, *Ann. Int. Med.,* 95, 56 (1981).
Kohler and Milstein, *Nature,* 256, 495 (1975).
Lane et al., *J. Immun. Methods,* 92, 261 (1986).
Little et al., *Clin. Chem.,* 29, 1080 (1983).
Little et al., *Clin. Chem.,* 29, 1113 (1983).
Lowrey and Soeldner, *Analytical Biochemistry,* 154, 424 (1986).
Makhlouf et al., *Carbohydrate Research,* 132, 93 (1984).
McDonald et al., *J. Biol. Chem.,* 253, 2327 (1978).
Means and Feeney, *Biochemistry,* 7, 2192 (1968).
Merrifield *J. Am. Chem. Soc.,* 85, 2149 (1963).
Miedema and Casparie, *Ann. Clin. Biochem.,* 21, 2 (1984).
Moore et al., *Ann. Clin. Biochem.,* 23, 85 (1986).
Moyle et al., *J. Immunology,* 20, 439 (1983).
Nakayama et al., *Clin. Chim. Acta,* 158, 293 (1986).
Nathan et al., *New Engl. J. Med.,* 310, 341 (1984).
Nerenberg et al., *J. Immun. Methods,* 24, 19 (1978).
Ney et al., *Analytical Biochemistry,* 118, 294 (1981).
Olufemi et al., *Clin. Chim. Acta,* 163, 125 (1987).
Peacock, *J. Clin. Pathol.,* 37, 841 (1984).
Playfair et al., *Br. Med. Bull.,* 30, 24 (1974).
Reif, *Immunochemistry,* 6, 723 (1969).
Rendell et al., *Clin. Chem.,* 31, 229 (1985).
Rucklidge et al., *Biochemica et Biophysica Acta,* 747, 165–170 (1983).
Shapiro et al., *J. Biol. Chem.,* 255, 3120 (1980).
Smith et al., *Anal. Biochem.,* 150, 76 (1985).
Staros et al., *Anal. Biochem.,* 156, 220 (1986).
Svendsen et al., *Diabetologia,* 21, 549 (1981).
Waddell and Hill, *J. Lab. Clin. Med.,* 48, 311 (1956).
Walton et al., *Carbohydrate Research,* 153, 285–293 (1986).
Walton and McPherson, *Carbohydrate Research,* 153, 285 (1986).
Weinryb et al., *Drug Metab. Rev.,* 10, 271 (1979).
Witzum et al., *Proc. Natl. Acad. Sci.,* 80, 2757 (1983).
Wong et al., *Anal. Biochem.,* 139, 58 (1984).
Yue et al., *Diabetologia,* 24, 377 (1983).
Yue et al., *Diabetes,* 29, 296 (1980).
Yue et al., *Diabetes,* 31, 701 (1982).
Curtiss et al, J. Clin. Invest., vol. 72, 1427 (1983).

TUBE ASSAY CLINICAL SAMPLES
Regression Line of % Hb A1c VS OD 405 nm

INHIBITION ASSAY USING CLINICAL SAMPLES

REGRESSION ANALYSIS
Inhibition Assay VS Electrophoresis

HETEROGENOUS Hb A1c ASSAY

IMMUNOASSAY OF GLYCOSYLATED PROTEINS EMPLOYING ANTIBODY DIRECTED TO REDUCTIVELY GLYCOSYLATED N-TERMINAL AMINO ACIDS

This application is a continuation-in-part of application Ser. No. 08/068,525, filed May 27, 1993, now abandoned, which was a continuation of application Ser. No. 07/397,781, filed Aug. 23, 1989, now abandoned.

BACKGROUND OF THE INVENTION

This invention relates to a method of detecting and quantifying glycosylated proteins. More particularly, the invention relates to an immunoassay for detecting and quantitating proteins that are glycosylated on their amino-terminal (N-terminal) amino acid. One such protein is hemoglobin $A_{1c}$ ($HbA_{1c}$), and the invention is particularly directed to immunoassays for detecting and quantitating $HbA_{1c}$. The invention also relates to antibodies specific for reduced glycosylated N-terminal amino acids that are used in the immunoassays of the invention and to immunogens and methods for making these antibodies.

The in vivo glycosylation (also called "glycation") of proteins may occur either enzymatically or non-enzymatically. In non-enzymatic glycosylation, a sugar is covalently coupled to the epsilon amino groups of available lysine residues or to the alpha amino group of accessible amino terminal (N-terminal) amino acids of the protein.

Non-enzymatic glycosylation of proteins with glucose proceeds in two stages. First, glucose combines with the amino group of the lysine or of the N-terminal amino acid to form an aldimine compound (a Schiff base). This reaction is reversible, and dissociation to unmodified protein and glucose readily occurs. Next, the aldimine intermediate is converted to a stable ketoamine derivative (1-deoxyfructose) by the Amadori rearrangement. Finally, over a period of weeks, the free carbonyls of the ketoamine derivatives form crosslinks between the glycosylated protein and adjacent proteins, and the resulting aggregates are called advanced glycosylation products.

Non-enzymatic glycosylation occurs in normal mammals and to a much greater extent in diabetic patients. Patients afflicted with diabetes are incapable of metabolizing glucose in a conventional manner resulting in increased amounts of glucose in their blood and urine. In diabetic and normal individuals, glucose has been shown to bind non-enzymatically to the amino groups of many proteins, including hemoglobin, collagen, albumin, lens crystallins, fibrinogen, lipoproteins, ferritin, myelin, transferrin, and immunoglobulins, although such glycosylation occurs to a greater extent in diabetics than in normals.

The quantitative measurement of glycosylated proteins in diabetes is clinically important for two reasons. First, the measurement of glycosylated protein levels allows for the monitoring of blood glucose levels over an extended time period and allows the assessment of diabetic metabolic control. The time period over which mean blood glucose concentrations may be determined is largely dictated by the length of time a given assayed protein normally remains in the circulation. Since transferrin and human serum albumin are normally present in the circulation for a short to intermediate time (the half-life of transferrin is about 8 days, and the half-life of albumin is about 10– 14 days), the measurement of the glycosylated forms provides a means of assessing short to intermediate glycemia. Hemoglobin is normally present in the circulation for a long time (the half-life of hemoglobin being about 2 to 3 months), and the measurement of glycosylated hemoglobin provides a means of assessing long term glycemia.

Second, non-enzymatic glycosylation has been implicated in the development of chronic diabetic complications, including accelerated cataract formation (due to advanced glycosylation products of crystallin lens protein) and atherogenesis (due to lipoprotein entrapment on arterial walls) contributing to the narrowing of blood vessels of the heart, brain, eyes, kidneys, and periphery. The measurement of glycosylated proteins and their advanced products may, therefore, be of prognostic value in the pathological sequelae involved in chronic hyperglycemia.

The main component of human hemoglobin (about 80–90% of the total hemoglobin) is $HbA_o$. It has a tetrameric structure comprising two alpha and two beta chains. $HbA_o$ is not glycosylated on its N-terminal amino acids. Preparations of $HbA_o$ isolated by ion exchange chromatography have been shown to contain a small proportion of $HbA_o$ molecules glycosylated on the available epsilon amino groups of lysines.

$HbA_{1a1}$, $HbA_{1a2}$, $HbA_{1b}$ and $HbA_{1c}$ are minor components of human hemoglobin identical in structure to $HbA_o$, except for the presence of a sugar residue covalently attached to the N-terminal valine residue of the beta chain. The sugar residues attached to the valine residues of $HbA_{1a1}$, $HbA_{1a2}$ and $HbA_{1c}$ are fructose diphosphate, glucose-6-phosphate and 1-deoxyfructose, respectively. The sugar attached to valine in $HbA_{1b}$ is not known.

About 4 to 5% of the total hemoglobin is $HbA_{1c}$ in normal persons, but the amount is substantially higher in diabetes, generally being about 8 to 10%, but sometimes as high as 20%. Also, its concentration varies widely in relation to diabetic control.

$HbA_{1c}$ is the most frequently measured glycosylated protein for clinical purposes, and a number of tests have been developed to measure it. See, e.g., Furth, *Analytical Biochemistry*, 175, 347–60 (1988); Peacock, *J. Clin. Pathol.*, 37, 841–51 (1984); Miedema and Casparie, *Ann. Clin. Biochem.*, 21, 2–15 (1984); and U.S. Pat. No. 4,629,692. Glycohemoglobin assays used routinely in clinical laboratories include: (1) affinity chromatography using m-aminophenylboronate columns; (2) cation exchange chromatography; (3) electrophoresis; and (4) isoelectric focusing. The most commonly used clinical methods are cation exchange chromatography for $HbA_{1c}$ and affinity chromatography for glycosylated hemoglobin. See Bodor et al., *Clin. Chem.*, 38, 2414–2418 (1992).

Each of the four measurement techniques that are currently in clinical use suffers from one or more of the following disadvantages: relatively high cost per sample measured; lack of specificity in the analyte measured; sensitivity to slight variations in conditions such as ionic strength, pH and temperature; difficulty in standardization; lack of reproducibility; being time consuming and labor intensive; inability to automate; and difficulty in assaying many samples simultaneously. See U.S. Pat. No. 4,629,692; Furth, *Analytical Biochemistry*, 175, 347–60 (1988); Peacock, *J. Clin. Pathol.*, 37, 841–51 (1984).

Immunoassays for measuring glycosylated proteins, particularly $HbA_{1c}$, are known. These various immunoassay techniques, and the antigens and antibodies used in them, will now be discussed.

First, European Patent Application No. 201,187 describes the preparation of monoclonal antibodies using purified HbA$_{1c}$. In particular, the application reports the preparation of monoclonal antibodies that preferentially bind to the glycated amino groups of hemoglobin, such as that of the N-terminal valine residues of the HbA$_{1c}$ beta chains. In particular, a glycated heptapeptide whose sequence corresponds to the sequence of the N-terminus of the beta chain of HbA$_{1c}$ inhibited the binding of one of these monoclonal antibodies to HbA$_{1c}$, whereas the non-glycated heptapeptide and the reduced glycated heptapeptide did not inhibit this binding. The patent application teaches that these monoclonal antibodies can be used in known immunoassay techniques to quantitate HbA$_{1c}$. It should be noted that only 2 out of 320 hybridomas produced monoclonal antibody preferentially reactive with HbA$_{1c}$, suggesting that little antibody specific for HbA$_{1c}$ is normally produced by immunized animals.

U.S. Pat. No. 4,629,692 (Dean) teaches an immunoassay method for determining total non-enzymatically glycosylated proteins and protein fragments in a biological fluid. The immunoassay method employs an antibody which selectively recognizes and binds Amadori-rearranged glucose residues (i.e., 1-deoxy-D-fructosyl residues). The immunogen used to prepare the antibody is Amadori-rearranged glucose covalently bound to a carrier molecule. Polylysine is the preferred carrier, and the Amadori-rearranged glucose is preferably attached to the epsilon amino groups of the lysine residues. The immunogen is prepared by glycosylating the carrier non-enzymatically in vitro. A linker may be used between the Amadori-rearranged glucose and the carrier. The preferred linker is lysine. Other linkers including lysine analogs and amino-functionalized amino acids such as ornithine and hydroxylysine may be used.

The antibody prepared as described above can be used in a conventional immunoassay to quantitate total glycosylated proteins in a biological fluid such as serum. To determine the level of a specific glycosylated protein, such as HbA$_{1c}$, it must first be separated from the other non-enzymatically glycosylated proteins. For instance, the Dean patent teaches that HbA$_{1c}$ can be separated by phenylboronate affinity chromatography and then quantitated using the disclosed antibody.

U.S. Pat. No. 4,658,022 (the '022 patent) teaches the preparation of antibodies to a linear peptide epitope of a protein. The linear peptide epitope comprises from 2 to 15 amino acids of any portion (N-terminal, C-terminal, or other portion) of the protein's sequence and may be modified with non-peptide groups such as carbohydrates. The linear peptide epitope is coupled to an immunogenic carrier for purposes of immunizing an animal. To perform the immunoassay, the antibodies are contacted with the protein which has been denatured sufficiently to expose, or increase the exposure of, the linear peptide epitope used for the preparation of the antibody. The use of monoclonal antibodies is preferred.

The '022 patent and U.S. Pat. No. 4,647,654 (the '654 patent) teach the use, in the system described above, of a glycosylated peptide containing at least 2 amino acids, preferably 5 to 15 amino acids, of the N-terminal sequence of hemoglobin coupled to an immunogenic carrier to prepare an antibody. The '654 patent teaches that a linker which optimizes antigenicity and coupling properties may be used between the peptide epitope and the carrier. The linker may comprise one or more amino acids not found in the normal sequence of hemoglobin. Both patents teach that monoclonal antibodies can be produced in this manner which are specific for the glycosylated synthetic peptide and the corresponding epitope on the HbA$_{1c}$ molecule when the HbA$_{1c}$ molecule is denatured to expose the epitope0 These antibodies do not cross-react with HbA$_o$ or with non-glycosylated peptides. The immunoassays used are conventional, except for the denaturation of hemoglobin. It should be noted that only 9 out of 200 hybridomas produced monoclonal antibody preferentially reactive with HbA$_{1c}$, suggesting that little antibody specific for HbA$_{1c}$ is normally produced by immunized animals.

U.S. Patent No. 4,478,744 (Mezei et al.) teaches the preparation of antibodies to a protein using a peptide antigen, the amino acid sequence of which corresponds to a portion of the amino acid sequence of the protein. With respect to hemoglobin, the patent teaches the preparation of antibodies to glycosylated hemoglobin, specifically HbA$_{1c}$, using a peptide consisting of 4 to 10, preferably 7, amino acids, the sequence of which corresponds to the N-terminal sequence of the beta chain of hemoglobin. The peptide is glycosylated before or after being coupled to an immunogenic carrier protein or polypeptide. The peptide-carrier combination is used to immunize an animal, preferably one that does not normally produce HbA$_{1c}$. Mezei et al. teaches that the resultant antibodies are specific for HbA$_{1c}$ and may be used in conventional immunoassays to quantitate HbA$_{1c}$. However, the '654 patent discussed above describes experiments showing that a polyclonal sheep antiserum produced according to the Mezei et al. method has no detectable specificity for HbA$_{1c}$ in an ELISA assay even when affinity purified (see Example 8 of the '654 patent). Also see, European Patent Application 201,187 discussed above.

U.S. Pat. No. 4,247,533 (Cerami et al.) and Javid et al., British Journal of Haematology, 38, 329 (1978) teach the preparation of antibodies to HbA$_{1c}$. The antibodies are produced by immunizing an animal, preferably one that does not normally form HbA$_{1c}$, with column purified human HbA$_{1c}$. The resulting antibody reacted equally well with HbA$_o$ and HbA$_{1c}$ and was, therefore, absorbed repeatedly with HbA$_o$. The absorbed antibody clearly distinguished HbA$_o$ from its glycosylated derivatives, but still cross-reacted slightly with human HbA$_{1a}$ and HbA$_{1b}$ and with dog and mouse HbA$_{1c}$. It also showed strikingly less reactivity with NaBH$_4$ reduced HbA$_{1c}$ than with unreduced HbA$_{1c}$. Also, certain reduced glycodipeptides, including reduced glycosylated valyl-histidine, failed to inhibit the reaction of the absorbed antibody with HbA$_{1c}$. The absorbed antibody was of low affinity and low titer. To overcome this problem, a specially modified radioimmunoassay (RIA) was employed. The '654 patent discussed above teaches that the reproducibility of this method is open to question (see column 2, lines 38–41, of the '654 patent).

Curriss and Witztum, *J. Clin. Invest.*, 72, 1427 (1983) describes the generation and characterization of six murine monoclonal antibodies that bind reduced glycosylated human plasma lipoproteins, but do not react with nonglycosylated or unreduced glycosylated plasma lipoproteins. The antibodies were prepared by immunizing mice with three injections of homologous low density lipoprotein (LDL) reductively glycosylated in the presence of glucose and sodium cyanoborohydride, followed by one injection of reductively glycosylated human LDL just before harvesting spleen cells to prepare the hybridomas. In competitive inhibition RIA, the dominant epitope recognized by these antibodies on reduced glycosylated LDL was identified as glucitol-lysine, the reduced hexose alcohol form of glucose conjugated to the epsilon amino group of lysine (glucitol-lysine completely inhibited the binding of each of the antibodies to reduced glysosylated LDL). Each of the six antibodies reacted with all reduced glycosylated proteins studied, including high density lipoprotein, albumin, hemoglobin and transferrin. The antibodies were also capable of identifying and quantitating glucitol-lysine residues on total plasma proteins and isolated lipoproteins of normal and diabetic individuals after reduction of the proteins with $NaBH_4$.

Witztum et al., *Proc. Natl. Acad. Sci. USA,* 80, 2757 (1983) describes the preparation of polyclonal antibodies by immunizing guinea pigs with homologous glycosylated or reductively glycosylated LDL. Immunization with reductively glycosylated LDL produced a high-titered antiserum that reacted with reductively glycosylated guinea pig LDL, but not with unreduced glycosylated LDL. Glucitol-lysine was a highly effective inhibitor of the binding of this antibody to reductively glycosylated LDL, as were other reductively glycosylated human proteins, including hemoglobin, albumin and transferrin. LDL glycosylated in the absence of a reducing agent was also immunogenic, although the antiserum was of lower titer and affinity. Homologous reductively glycosylated albumin was also immunogenic, and immunization with this compound produced an antiserum that reacted with reductively glycosylated albumin, but not with unreduced glycosylated albumin or reductively glycosylated LDL. All antibody activities were measured in a solid-phase RIA.

Nakayama et al., *Clinica Chimica Acta,* 158, 293–99 (1986) describes an RIA for glycated human serum protein using antiserum obtained by immunizing guinea pigs with reductively glycated human albumin. The antiserum was affinity absorbed on columns of native human serum albumin, and the absorbed antiserum recognized reductively glycated albumin and glucitollysine, but not non-reductively glycated albumin, native human albumin, lysine, sorbitol or mannitol. The antiserum was also capable of identifying and quantitating native human serum albumin and nonreductively glycated albumin after reduction of the protein with $NaBH_4$.

Go et al., *Clinical Chimica Acta,* 163, 63–73 (1987) reports the development of an enzyme linked immunosorbent assay (ELISA) for glycosylated proteins using a polyclonal antiserum which was prepared using reductively glycosylated homologous high and low density lipoproteins (HDL and LDL) as the immunogen. The article teaches that the antiserum is specific for the glucose-lysine bond, and that it recognizes, in a dose-dependent manner, all reduced glycosylated proteins tested, including albumin, fibrinogen, LDL, HDL, polylysine and hemoglobin. The antiserum had no affinity for native proteins or for unreduced glycosylated proteins. The ELISA assay is reported to be sensitive and capable of measuring a large number of samples in a relatively short period of time, but the article teaches that the conditions of the assay are critical and that major deviations from the described protocol lead to loss in sensitivity and reproducibility. See page 66 of Go et al.

SUMMARY OF THE INVENTION

The present invention provides an immunoassay for a protein such as $HbA_{1c}$ that is non-enzymatically glycosylated on the alpha amino group of its N-terminal amino acid. Antibodies having specificity for Glc-ol-X are prepared as described below and used in the immunoassay. In the formula Glc-ol-X, X is the N-terminal amino acid of the glycosylated protein, and X may be any amino acid except lysine for the reasons discussed in detail below. Glc-ol is the reduced form of the sugar attached to X on the glycosylated protein. Glc-ol may be any reduced sugar, such as glucitol or mannitol.

The antibody, which is also part of the invention, is prepared by immunizing an animal with an immunogen of the formula $(Glc-ol-X-L)_n$-carrier wherein:

X and Glc-ol are as defined above, and Glc-ol is attached to the alpha amino group of X;

L is a bond or a linker group;

the carrier is an immunogenic compound other than the glycosylated protein; and n is from 1 to the number of available coupling sites on the carrier.

The glycosylated protein that is to be assayed must be treated with a reducing agent before contacting it with the antibody to perform the immunoassay. This step is necessary to convert the glycosylated N-terminal amino acid of the protein to the Glc-ol-X form. In this way the antibody of the invention will recognize the glycosylated protein and bind with it. The antibody will recognize the glycosylated protein selectively in the presence of non-glycosylated proteins, proteins glycosylated on the epsilon amino group of lysine and proteins glycosylated on other N-terminal amino acids. However, if a plurality of proteins are present in a test sample which have the same glycosylated N-terminal amino acid, some method of identifying or separating out the protein of interest must be used.

The invention further comprises the $(Glc-ol-X-L)_n$-carrier compound used as the immunogen to prepare the antibody and methods of making this compound. These methods comprise reductively glycosylating X or X-L to produce Glc-ol-X or Glc-ol-X-L. The Glc-ol-X and Glc-ol-X-L may then be directly coupled to the immunogenic carrier, or the Glc-ol-X may be coupled to L before being coupled to the carrier.

The invention also provides a kit for detecting or quantitating the glycosylated protein. The kit comprises a container of antibody directed to Glc-ol-X. The kit may also include one or both of the following: 1) a container of reducing agent for reducing the sugar residue on the N-terminal amino acid of the glycosylated protein; or 2) a container of a labeled component useful for detecting or quantitating the glycosylated protein bound to the antibody.

DETAILED DESCRIPTION OF THE PRESENTLY PREFERRED EMBODIMENTS OF THE INVENTION

Figure 1:
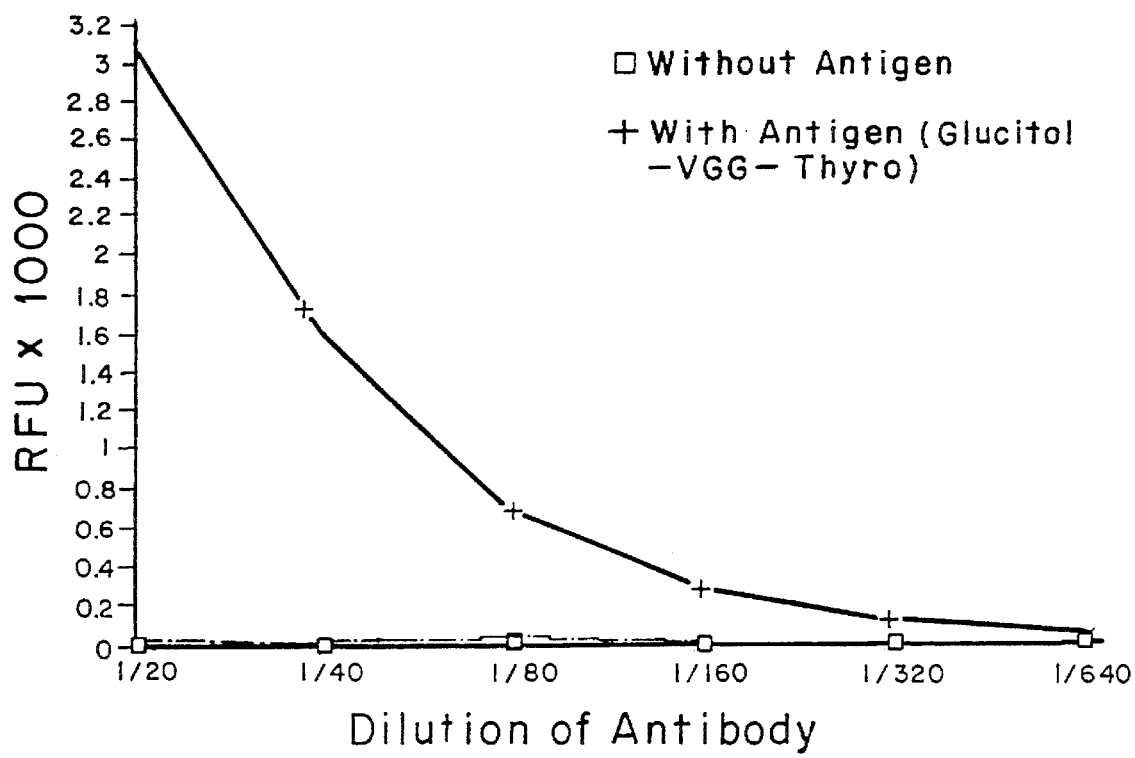
FIGS. 1–3: Graphs of relative fluorescence units (RFU) versus antibody dilution. The data on the graph were obtained by performing a direct binding enzyme linked fluorescence assay (ELFA) utilizing anti-glucitol-VGG-BSA antibodies which had been affinity purified on a column of glucitol-VGG Sepharose. The antigens are as indicated.

The immunogen used to stimulate production of the antibodies of the present invention comprises one or more Glc-ol-X-L residues coupled to an immunogenic carrier. X is the N-terminal amino acid of a protein that is glycosylated on the alpha amino group of its N-terminal amino acid. X may be any amino acid except lysine, and the glycosylated protein may be any such protein to which it is desired to produce an antibody, except those having lysine as the N-terminal amino acid.

The reason X cannot be lysine is as follows. Glycosylated proteins commonly contain lysine residues glycosylated on their epsilon amino groups. It is expected that antibodies formed to Glc-ol-lysine, where the Glc-ol is on the alpha amino group, would likely cross react with the more common glycosylated lysines having the sugar residue attached to their epsilon amino group. Thus, such antibodies would react with many different glycosylated proteins in a non-specific manner. The goal of the present invention is to avoid such a generalized non-specific reaction with numerous glycosylated proteins.

L in $(Glc\text{-}ol\text{-}X\text{-}L)_n$-carrier may be a bond linking Glc-ol-X to the carrier. If L is a bond, then X must terminate in a functional group such as carboxyl, thiol or hydroxyl which is active in a coupling reaction to an appropriate group in the carrier molecule.

L may also be any known linking group. For instance, L may be an aliphatic chain comprising from about 1 to about 20 atoms, excluding hydrogen. Normally the linking group will terminate in a functional group such as amino, carboxyl, thiol, hydroxyl or maleimido which is active in a coupling reaction to an appropriate group in the carrier molecule. It is most common to form amino or carboxyl derivatives and link them by conventional peptide condensation reactions to counterpart carboxyl and amino groups in the carrier.

Preferred linking groups are an amino acid or a peptide containing less than ten, preferably containing two, amino acids. The combination of X and the amino acid(s) of the linking group do not correspond to the N-terminal sequence of the glycosylated protein to which it is desired to form an antibody. The amino acid(s) of the linking group and the entire linking group are also preferably relatively non-immunogenic. For this reason, the amino acid glycine and the dipeptide glycine-glycine are particularly preferred linking groups.

When L is an amino acid or a peptide, it may be linked to X by known peptide synthetic methods. For instance, a solid phase peptide synthesis method like those described in Merrifield, *JACS*, 85, 2149 (1963); Davis et al., *Biochemistry International*, 10, 394–414 (1985); Stewart and Young, *Solid Phase Peptide Synthesis* (1969); U.S. Pat. No. 3,941,763; Finn et al. in *The Proteins*, third edition, volume 2, pages 105–253 (Neurath et al. ed. 1976); and Erickson et al. in *The Proteins*, third edition, volume 2, pages 257–527 (Neurath et al. ed. 1976) may be used. These methods may also be used to prepare L when it is a peptide. Suitable synthetic peptides which may be used for X, for L when L is a peptide, or for X-L when L is an amino acid or peptide, may also be purchased commercially from various sources including Sigma Chemical Co., St. Louis, Mo., Peninsula Laboratories, Belmont, Calif., Bachem Inc., Torrance, Calif. and Vega Biochemicals, Tucson, Ariz.

It is preferred that X be reductively glycosylated before being coupled to the carrier to prevent the formation of Glc-ol-lysine residues or other Glc-ol residues that might produce interfering or non-specific antibodies. Further, if L is an amino acid or a peptide having epsilon amino groups, it is preferable to reductively glycosylate X before it is attached to L.

To reductively glycosylate X (alone or after being attached to L), an excess of a sugar corresponding to the one found on the N-terminal amino acid of the glycosylated protein of interest is reacted with X or X-L in the presence of a carbohydrate reducing agent such as sodium cyanoborohydride [see Curriss and Witztum, *Clin. Invest.*, 72, 1427–1438 (1983) and Friedman et al., *Int. J. Pept. Protein Res.*, 6, 183–185 (1974)], pyridine-borane [see Wong et al., *Anal. Biochem*, 139, 58–67 (1984)], or sodium borohydride, [see Means and Feeney, Biochemistry, 7, 2191–2200 and Go et al., *Proc. Nat'l Acad. Sci. USA*, 80, 2751–2761 (1983)]. The reductively glycosylated X or X-L is separated from the carbohydrate reducing agent, and its non-glycosylated counterpart. This may be accomplished by conventional means, but preferably is accomplished using molecular sieve chromatography and, if necessary, ion exchange chromatography.

Suitable carriers are compounds capable of stimulating the production of antibodies to haptens coupled to them in a host animal. Such carriers are conventional and well-known. They are generally high molecular weight compounds. In most cases, the carrier will be a protein or polypeptide, although other materials such as carbohydrates, polysaccharides, lipopolysaccharides, nucleic acids, and the like of sufficient size and immunogenicity can be used.

Suitable immunogenic carrier proteins and polypeptides will generally have molecular weights between 4,000 and 10,000,000, and preferably greater than 15,000. Such suitable carriers include proteins such as albumins (e.g., bovine serum albumin, ovalbumin, human serum albumin), immunoglobulins, thyroglobulins (e.g., bovine thyroglobulin), hemocyanins (e.q., Keyhole Limpet hemocyanin) and polypeptides such as polylysine or polyalaninelysine.

Next the Glc-ol-X-L is coupled to the carrier. Methods of effecting this coupling are well-known. For instance, the Glc-ol-X-L residues may be coupled to the carrier with conjugating reagents such as glutaraldehyde, a water soluble carbodiimide such as 1-(3-dimethylaminopropyl)-3-ethylcarbodiimide hydrochloride (ECDI), N-N-carbonyldiimidazole, 1-hydroxybenzotriazole monohydrate, N-hydroxysuccinimide, n-trifluoroacetylimidazole cyanogen bromide, 3-(2'-benzothiazolyl-dithio) propionate succinimide ester hydrazides or affinity labeling methods. See also *Pierce Handbook and General Catalog* (1989) for a list of possible coupling agents.

Additional references concerning conventional immunogenic carrier materials and techniques for coupling haptens thereto are: Erlanger, *Methods In Enzymology*, 70, 85–104 (1980); Makela and Seppala, *Handbook of Experimental Immunology* (Blackwell 1986); Parker, *Radioimmunoassay of Biologically Active Compounds* (Prentice-Hall 1976); Butler *J. Immunol. Meth.*, 7, 1–24 (1974); Weinryb and Shroff, *Drug. Metab. Rev.*, 10, 271–83 (1979); Broughton and Strong, *Clin. Chem.*, 22, 726–32 (1976); Playfair et al., *Br. Med. Bull.*, 30, 24–31 (1974).

In the formula (Glc-ol-X-L)$_n$-carrier, n is the number of Glc-ol-X-L residues attached to the carrier. The number of such residues (the "epitopic density") on the carrier molecule will range from 1 to the number of available coupling groups on the carrier molecule. The epitopic density on a particular carrier will depend upon the molecular weight of the carrier and the density and availability of coupling sites. Optimal epitopic densities fall between about 10% and about 50% of the available coupling groups on the carrier molecule.

After the (Glc-ol-X-L)$_n$-carrier has been synthesized, it is used to prepare antibodies. Methods of preparing antibodies are well-known and conventional. For instance, the antibodies of the present invention may be prepared by injecting a suitable host animal (such as a rabbit, goat, horse or other mammal) with the immunogen of the invention in admixture with an adjuvant. The injections of immunogen are continued until an antiserum of suitable titer is obtained. The antiserum is harvested and may be further purified using known techniques if needed or desired. For instance, the antibodies may be affinity purified or may be fractioned such as by DE-52 chromatography.

Alternatively, the antibodies of the invention can be prepared by somatic cell hybridization by fusing cells from an immunized animal (such as rats, hamsters, mice or other mammal) with an immortal cell line such as myeloma cells. The fused cells are cloned, and monoclonal antibodies of appropriate specificity can be isolated by screening the cloned fused cells. Techniques of preparing monoclonal antibodies are well-known.

Thus, antibody suitable for use in the invention can be monoclonal or polyclonal antibody, can be an antiserum or a purified fraction thereof (such as DE-52 affinity purified or affinity adsorbed antibody), can be any of the known isotypes or subclasses (such as IgG, IgM, etc.), can be an antibody fragment (such as Fab, F(ab') or F(ab')$_2$ that is capable of binding antigen, can be a single-chain antibody prepared by recombinant DNA techniques, etc. The only requirement is that the final antibody preparation have specificity for the Glc-ol-X epitope and be capable of binding to this epitope on the reduced glycosylated protein which it is desired to assay in the immunoassay.

The antibodies of the invention can be used in any immunoassay method that allows the detection or quantitation of non-enzymatically glycosylated proteins in a biological material. Many such techniques are known.

The only modification necessary is that the glycosylated protein that is to be assayed must be treated with a reducing agent before contacting the protein with the antibody to perform the immunoassay. This step is necessary to convert the glycosylated N-terminal amino acid of the protein to the Glc-ol-X form. In this way the antibody of the invention, which is specific for Glc-ol-X, will recognize the glycosylated protein and bind with it. No other special conditions are necessary. In particular, it is not necessary to treat the glycosylated protein with various denaturing conditions as is required by certain prior art assay techniques.

Suitable immunoassay methods include radioimmunoassay, enzyme immunoassay and fluorescence immunoassay. The immunoassay may be done in the competitive binding format or may be an immunometric assay. It may be a homogenous or hererogenous assay. Suitable homogenous techniques are fluorescence quenching and enhancement, energy transfer immunoassay, double antibody steric hinderance immunoassay, substrate-labeled immunoassay, prosthetic group-labeled immunoassay and enzyme modulator-labeled immunoassay.

One preferred immunoassay format is a direct binding assay in which reduced glycosylated protein in a sample such as a red blood cell (RBC) lysate is immobilized on a solid surface. Suitable solid surfaces are well-known and include glass, polystyrene, polypropylene, polyethylene, nylon, polyacrylamide, and agaroses. The immobilized antigen is contacted with antibody which is specific for Glc-ol-X (primary antibody). The primary antibody may be labeled so that the antibody bound to the immobilized antigen can be detected or quantitated. The amount of antigen (protein glycosylated on its N-terminal amino acid) in the sample can be quantitated since the amount of label bound to the solid surface after unbound materials are washed away is proportional to the amount of antigen present in the sample. Alternatively, after washing away unbound primary antibody, a labeled secondary antibody which binds specifically to the primary antibody may be added as a means to detect and quantitate the glycosylated protein of interest that is present in the sample.

Especially preferred direct binding immunoassays are the assays described in detail in Examples 10, 13, 15 and 20–23. In particular, the direct binding assays described in Examples 13, 15 and 20–23 employ lysates of whole blood, making the assays very simple to perform. They also utilize a colorimetric detection system. Such a system can be used to quantitate glycosylated proteins, but can also be used for a qualitative or semi-quantitative assay since the end point can be observed with the naked eye. Thus, such assays may be particularly valuable in settings where expensive equipment and experienced laboratory personnel are not available, such as in a physicians' office, in a patient's home or in underdeveloped areas of the world. Most preferred is the direct binding assay described in Examples 20 and 21 wherein a whole blood sample is subjected to conditions which lyse the red blood cells, reduce the released hemoglobin and coat the reduced hemoglobin on the wells of a microtiter plate all in one step (i.e., lysis, reduction and coating occur simultaneously).

Suitable labels for either the primary or secondary antibody are well-known in the art. They include: 1) enzymes (e.g., horseradish peroxidase, malate dehydrogenase, staphylococcal nuclease, delta-5-steroid isomerase, yeast alcohol dehydrogenase, alphaglycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase and acetylcholine esterase); 2) fluorophores (such as fluorescein isothiocyanate, rhodamine, phycoerythrin, phycocyanin, allophycocyanin, o-phtaldehyde and fluorescamine), 3) radionucleotides (such as $^{125}$I); 4) bioluminescent labels (such as luciferin, luciferase and aequorin); 5) chemiluminescent labels (such as luminol, isoluminol, aromatic acridinium ester, imidazole, acridinium salt and oxalate ester); and 6) biotin. The binding and detection of these labels can be done using standard techniques known to those skilled in the art.

An alternate and also preferred immunoassay construct is an inhibition assay. In this type of assay, varying amounts of liquid phase reduced glycosylated protein such as reduced $HbA_{1c}$ in a RBC or whole blood lysate is used as the inhibitor. The inhibitor is mixed with and competes with a fixed amount of reduced glycosylated protein immobilized on a solid surface (such as those described above) for a limited number of available binding sites on the anti-Glc-ol-X antibody (primary antibody). By comparing the inhibition of primary antibody binding obtained for known inhibitor concentrations with that obtained with biological samples, the amount of glycosylated protein in the biological sample may be determined. The primary antibody may be labeled, or a labeled secondary antibody may be used. The labels are the same as described above. A particularly preferred inhibition assay is the inhibition ELFA described in Example 11.

A sandwich (capture, two-site) assay is also possible. In this assay, anti-Glc-ol-X antibody is immobilized on a solid surface such as those described above. The reduced glycosylated protein that is to be assayed is then contacted with the immobilized anti-Glc-ol-X antibody. After washing away unbound material, labeled antibody to the glycosylated protein is added, and the amount of labeled antibody bound is proportional to the amount of glycosylated protein in the original sample. The labels are the same as described above. The second labeled antibody does not have activity for Glc-ol-X, but is directed to another epitope on the glycosylated protein. Thus, this technique is particularly suitable for detecting or quantitating glycosylated protein when it is in admixture with other proteins that are glycosylated on the same N-terminal amino acid. Alternatively, the labeled antibody may be the antibody to Glc-ol, and the immobilized antibody may be the antibody directed to another epitope on the glycosylated protein.

Finally, a homogenous fluorescence polarization assay is possible. In such an assay, reduced glycosylated protein competes with Glc-ol-X-L or Glc-ol-X coupled to a fluorescent labeled low molecular weight carrier molecule (such as poly-L-lysine having a molecular weight of 3600) for the anti-Glc-ol-X antibody. The amount of fluorescence polarization is inversely related to the amount of reduced glycosylated protein in the test sample.

The specific concentrations, the temperature and times of incubation, as well as other assay conditions, can be varied in whatever immunoassay is employed depending on such factors as the concentration of the antigen in the sample, the nature of the sample, and the like. Those skilled in the art will be able to determine operative and optimal assay conditions for each determination while employing routine experimentation.

The biological material to be assayed according to the present invention may be any biological fluid containing the glycosylated protein of interest. It will usually be blood or a component thereof such as RBC lysates, serum or plasma, but may be other appropriate fluids such as saliva.

The invention also comprises a kit for detecting or quantitating a protein that is non-enzymatically glycosylated on the alpha amino group of its N-terminal amino acid. The kit is a packaged combination of one or more containers holding reagents useful in performing the immunoassays of the invention. Suitable containers for the reagents of the kit include bottles, vials, test tubes and microtiter plates.

The kit will comprise a container of antibody directed to Glc-ol-X. The antibodies are those describe above, and they may be labeled if they are to be used to detect or quantitate the glycosylated protein. The antibodies may be in solution, may be lyophilized or may be bound to a solid surface, such as those described above.

The kit may further comprise a container of reducing agent for reducing the sugar residue on the alpha amino group of the N-terminal amino acid of the glycosylated protein. These reducing agents are known and conventional and include those described above.

The kit may also comprise a container of a labeled component useful for detecting or quantitating the amount of the glycosylated protein bound to the antibody. This labeled component may be a labeled antibody specific for the anti-Glc-ol-X antibody, may be a labeled reduced glycosylated protein or peptide, or may be labeled Glc-ol-X or labeled Glc-ol-X-L such as Glc-ol-X or Glc-ol-X-L coupled to poly-L-lysine for fluorescence polarization.

Finally, the kit may contain other materials which are known in the art and which may be desirable from a commercial and user standpoint such as buffers, enzyme substrates, diluents, standards, etc. The kit may also include containers such as test tubes and microtiter plates for performing the immunoassay.

The invention is particularly directed to an immunoassay for glycosylated hemoglobin. More particularly, it is directed to an immunoassay for $HbA_{1c}$ which has valine as the amino terminal amino acid, and the invention provides antibodies that react specifically with glucitol-valine or mannitol-valine. A preferred method of preparing such antibodies and preferred immunoassay techniques which may be used to detect or quantitate HbAmc are described in the Examples below, but other immunogens, antibody production techniques and immunoassay methods could be used as described in general terms above.

Briefly, in a preferred embodiment described below, an antibody was prepared by immunizing animals with the immunogen glucitol-valine-glycine-glycine-BSA. The resulting antisera were high titered with half-maximal binding to immunogens bearing glucitol-valine epitopes occurring at a dilution of 1:40,000 to 1:100,000. The IgG fractions of the resulting antisera were prepared and affinity purified using either glucitol-valine-Sepharose or glucitol-valine-glycine-glycine-Sepharose. The resulting affinity purified antibody specifically detected the glucitol-valine epitope as shown by the results in Examples 10–12. In particular, the binding of the affinity purified antibody to reduced $HbA_{1c}$ was specifically inhibited by reductively glycated $HbA_{1c}$, by reduced RBC lysates and by glucitol-valine-glycine-glycine. The approximate association constant (functional affinity) of the antibodies for $HbA_{1c}$ is 1.5 to 3.4 nM. It has also been determined that affinity purification or adsorption is not necessary to obtain an antibody preparation that reacts specifically with glucitol-valine epitopes. See Examples 13–15. Finally, quantitative measurements of $HbA_{1c}$ in RBC lysates and whole blood lysates correlate well with the results obtained by standard techniques. See Examples 10, 11 and 13–15.

In another preferred embodiment described below, antibodies have been prepared by immunizing animals with the immunogens mannitol-valine-glycine-glycine-BSA (mannitol-VGG-BSA) and mannitol-valine-glycine-glycine-HSA (mannitol-VGG-HSA). Both polyclonal and monoclonal antibodies have been obtained, but one of the monoclonal antibodies (designated MML03) obtained using mannitol-VGG-HSA as the immunogen is preferred. Quantitative measurements of $HbA_{1c}$ in whole blood lysates using both the polyclonal and monoclonal antibodies correlate well with the results obtained by several standard techniques. See Examples 20–23.

EXAMPLES

Example 1

Preparation of Glucitol-Valine-Glycine-Glycine

A reaction solution was prepared by dissolving 10 mg valine-glycine-glycine (VGG) peptide (Sigma Chemical Co., St. Louis, Mo., U.S.A.) in 10 ml of an aqueous solution of 80 mM glucose (Fisher Scientific Co., Fair Lawn, N.J., U.S.A.) and 12.5 mg/ml of freshly dissolved $NaCNBH_3$ (Sigma Chemical Co., St. Louis, Mo., U.S.A.) prepared in distilled water. The freshly prepared reaction solution was filter sterilized using a 0.2 um acrodisc filter (Gelman Sciences, Ann Arbor, Mich., U.S.A.) into a sterile screw cap 15 ml polystyrene tube (Corning Glass Works, Corning, N.Y., U.S.A.). Mock reaction, consisting of all reactants with the exception of glucose, was performed for comparative purposes.

The sterilized reaction solution was incubated at room temperature for 7–20 days, at which time reductively glycated VGG peptide was isolated by gel filtration chromatography using a 1×50 cm low pressure econo-column (Bio-Rad Laboratories, Richmond, Calif., U.S.A.) containing a total volume of 40 ml of Bio-Gel P-2, 400 mesh (Bio-Rad Laboratories, Richmond, Calif., U.S.A.), previously equilibrated with de-gassed distilled water. Fractionation was accomplished at ambient temperature by loading 1–2 ml of the reaction solution on the column. The column was run at a flow rate of 4 ml/hr, and 1 ml fractions were collected using distilled water as an eluting solvent.

The fractions collected were subsequently analyzed for peptide using bicinchonimic acid (BCA) [Smith P. K. et al., *Anal. Biochem.*, 150, 76–85 (1985), Lane et al., *J. Immunol. Methods*, 92, 261–270 (1986)], or low U.V. absorption [Waddle, *J. Lab. Clin. Med.*, 48: 311–314 (1956)]. They were also analyzed for neutral hexoses using phenolsulfuric acid [Dische et al., *Arch. Biochem. Biophys.*, 22: 169 (1949)], and for free amino groups using 2,4,6-trinitrobenzene sulfonic acid (TNBS) [Fields, *Methods in Enzymology*, 25b: 464–468 (1972)]. Peptide-containing fractions (BCA reactive) which were free of amino groups (no reaction with TNBS and hexose no reaction with phenol-sulfuric acid) were pooled, lyophilized, reconstituted with 1 ml of distilled water and re-analyzed by the BCA, TNBS and phenolsulfuric acid methods.

The concentrated material remained BCA reactive, but failed to react with TNBS and phenol sulfuric acid, suggesting that the isolated material consisted of glucitol-N-terminal-blocked VGG peptide devoid of free glucose and $NaCNBH_3$. Amino acid analysis revealed the presence of glycine but not valine which is expected if all available valine residues were reductively glycated. The purified material was subsequently coupled to protein carriers and Sepharose 4B (see Examples 3–5).

Example 2

Preparation of Glucitol-Human Hemoglobin

Human hemoglobin (Sigma Chemical Co., St. Louis, Mo., U.S.A.) was reductively glycated with glucose in the same manner as described above for VGG. Reductively glycated hemoglobin was separated from $NaCNBH_3$, glucose reactants and low-molecular weight reaction products by exhaustive dialysis against water using Spectropore cellulose dialysis tubing (American Scientific Products, McGaw Park, Ill., U.S.A.) of an average molecular weight cut off of about 12–14K.

The extent of amino group modification was determined by the TNBS method of Fields, *Methods in Enzymology*, 25b, 464–468 (1972), using a control of human hemoglobin which had been reduced in the absence of glucose ("$CNBH_3$ control") as a measure of total available hemoglobin amino groups. Using this method, reductively glycated hemoglobin was determined to have 26% of available amino groups modified with glucitol. Glucitol-human hemoglobin so prepared was used in direct binding enzyme-linked fluorescence assay (ELFA) for antibody specificity characterization (see Example 10).

Example 3

Preparation of Glucitol-Valine-Glycine-Glycine-Bovine Serum Albumin .(Glucitol-VGG-BSA)

Glucitol-valine-glycine-glycine (glucitol-VGG) prepared as described in Example 1 was coupled to bovine serum albumin (BSA) (Sigma Chemical Co., St. Louis, Mo., U.S.A.) using 1-ethyl-3-(3-dimethylaminopropyl)carbodiimide hydrochloride (EDCI) (Sigma Chemical Co., St. Louis, Mo., U.S.A.) and the sodium salt of N-hydroxysulfosuccinimide (sulfo-NHS) (Pierce Chemical Co., Rockford, Ill., U.S.A.) by a modification of the method of Staros et al., *Anal. Biochem.*, 156, 220–222 (1986). Briefly, after pre-cooling all reactants on ice, 228 ul of a 10 mg/ml aqueous solution of sulfo-NHS was added to 500 ul of a 2.4 mg/ml aqueous solution of glucitol-VGG and mixed. Then, 1.5 ml of a freshly prepared 20 mg/ml solution of EDCI in distilled water was added, mixed immediately and allowed to react on ice for 15 minutes. BSA was subsequently added as 1160 ul of a 5 mg/ml aqueous solution. This reaction solution was mixed, and coupling was continued overnight at 4° C. The reaction mixture was then dialyzed exhaustively at 4° C. against distilled water using Spectropore cellulose dialysis tubing (American Scientific Products, McGraw Park, Ill., U.S.A.) of an average molecular weight cut-off of 12–14K. Controls in which distilled water was substituted for peptide, or for peptide and carbodiimide, or for peptide, carbodiimide and sulfo-NHS were included for assessment of both extent of conjugation and antibody specificity.

TNBS amino group determination, performed as described in Example 1, of glucitol-VGG-BSA conjugate and BSA conjugate control (without glucitol-VGG, EDCI or sulfo-NHS) revealed 42% of the 60 available BSA amino groups were substituted with glucitol-VGG after conjugation (i.e., there were 25 glucitol-VGG peptides/BSA carrier molecule).

Example 4

Preparation of Glucitol-Valine-Glycine-Glycine-Bovine Thyroglobulin (Glucitol-VGG-Thyro)

In a similar manner glucitol-VGG (prepared as described in Example 1) was coupled to bovine thyroglobulin (Sigma Chemical Company, St. Louis, Mo., U.S.A.). Molar ratios of reactants were identical to those used for the coupling of glucitol-VGG to BSA described above in Example 3, except that an equimolar amount of 1-cyclohexyl-3-(2-morpholinoethyl)-carbodiimide metho-p-toluenesulfonate (CMC) was substituted for the EDCI as the water soluble carbodiimide.

TNBS amino group determination, performed as described in Example 1, of glucitol-VGG-Thyro conjugate and thyroglobulin conjugate control (without glucitol-VGG, CMC or sulfo-NHS) revealed that 26% of the estimated 194 available thyroglobulin amino groups were substituted with glucitol-VGG after conjugation.

Example 5

Preparation Of Glucitol-Valine-Glycine-Glycine-Sepharose

Glucitol-VGG-Sepharose immunosorbant was prepared by the addition of 254 mg of CMC to 533 ul of glucitol-VGG (8.67 mg/ml in $H_2O$). After mixing and solubilizing the carbodiimide, the peptide-carbodiimide solution was added to 2 ml of AH-Sepharose 4B (Pharmacia Fine Chemicals AB, Uppsala, Sweden) (prewashed according to manufacturer's instructions), and the mixture was mixed by inversion overnight at room temperature in a 4 ml (15×45 mm) screw cap micro sample vial (American Scientific Products, McGaw Park, Ill., U.S.A.). The immunoabsorbent was stored at 4° C. in the presence of 0.02% $NaN_3$ prior to use. The immuno-absorbent was used in affinity purification as described in Example 7.

Example 5

Preparation of Glucitol-Valine-Sepharose

Glucitol-valine-Sepharose immunoabsorbent was prepared as described in Example 5, except that 595 ul of glucitol-valine (10 mg/ml in $H_2O$) were used in place of the glucitol-VGG. The glucitol-valine was prepared as described in Example 1 for VGG.

This immunoabsorbent was also stored at 4° C. in the presence of 0.02% $NaN_3$ prior to use. It was used in affinity purification as described in Example 7.

Example 7

Preparation of Glucitol-Valine Reactive Antibodies

New Zealand white female rabbits (Langshaw Farms, Augusta, Mich., U.S.A.) were initially immunized by the method of Vaitakaitis et al., *Clin. Endo. Metab.*, 33, 988 (1971) with 2 ml emulsion consisting of complete Freund's adjuvant (CFA) containing 500 ug of glucitol-VGG-BSA prepared as described in Example 3. Subsequent immunizations were with emulsions of Freund's incomplete adjuvant containing 200 ug of glucitol-VGG-BSA. These subsequent immunizations were performed 5 weeks after the initial injection and at 2–8 week intervals thereafter.

The animals were bled from the ear 7–10 days after each immunization by the method of Nerenberg et al., *J. Immol. Methods.*, 24, 19 (1978). Serum samples from each rabbit were examined for antibody reactivities by direct binding enzyme-linked immunofluorescence assay (ELFA) performed as described in Example 10 for all bleedings following the third immunization. Sera obtained were stored frozen at −20° C. until used.

Purification of the desired antibodies was achieved by IgG fractionation of the sera using batchwise ion-exchange chromatography on DE-52 cellulose (Whatman LTD, Springfield Mill Maidstone Kent, England) by the method of Reif, *Immunochemistry*, 6, 723 (1969). With selected antisera, the IgG fractions were subsequently further purified by affinity chromatography on either glucitol-valine-Sepharose (prepared as described in Example 6) or glucitol-VGG-Sepharose (prepared as described in Example 5), or were affinity adsorbed using glutaraldehyde cross-linked human hemoglobin.

Affinity purification of anti-glucitol-VGG-BSA was accomplished by placing 1 ml of either glucitol-VGG-Sepharose or glucitol-valine-Sepharose in a Bio-Rad disposable polypropylene econo-column (Bio-Rad Laboratories, Richmond, Calif., U.S.A.). The matrix was then washed with 50 ml of PBS (0.01M sodium phosphate in 0.15M NaCl), pH 7.3, followed by 3 ml of potassium iodide (KI) in PBS, pH 8.0, and then a 50 ml PBS, pH 7.3, wash. Subsequently, the washed matrix was incubated with rotation for 2 hours at 37° C. with 14 ml of a DE-52 IgG fraction of antisera. Unbound material was collected, after which the matrix was washed two times with 10 ml PBS, pH 7.3, and bound antibody was collected by elution with 3 ml of 2M KI in PBS, pH 8.0, followed immediately by dialysis of the eluate against 2 liters of PBS, pH 7.3, overnight at 4° C. The resultant dialyzed affinity purified antibody was used in direct binding and inhibition ELFA assays (see Examples 10–11).

Removal of antibodies in the anti-glucitol-VGG-BSA preparation which might react with unreduced human hemoglobin was accomplished by affinity adsorbing DE-52 IgG fractions of antisera with denatured, glutaraldehyde-insolubilized human hemoglobin prepared as follows. Two hundred mg human hemoglobin (Sigma Chemical Co., St. Louis, Mo., U.S.A.) dissolved in 10 ml of PBS, pH 7.3, containing 1M KI was cross-linked in water using a modification of the method of Avrameas and Terynck, *Immunochemistry* 6, 53 (1969) at a final glutaraldehyde concentration of 0.5%. After three days of reaction, insoluble hemoglobin was obtained by centrifugation, and was collected on a Whatman No. 1 paper (Whatman LTD, Springfield Mill Maidstone Kent, England) by vacuum filtration using a Coors-Buckner funnel (American Scientific Products, McGaw Park, Ill., U.S.A.). The cross-linked hemoglobin on the filter was washed with 1 liter of PBS, pH 7.3. It was then incubated for 15 min at room temperature with 500 ml of 0.05M $NH_4Cl$, which was removed by vacuum filtration. Next, the insolubilized hemoglobin was washed with 400 ml PBS, pH 7.3, which was also removed by vacuum filtration.

The washed cross-linked hemoglobin was used to remove any possible hemoglobin-reactive antibodies from anti-glucitol-VGG-BSA IgG fractions by incubating 10 mg of glutaraldehyde cross-linked human hemoglobin with 2 ml of a DE-52 fraction of antisera with mixing end over end on a rotator for 3.5 hours at 37° C. Hemoglobin-adsorbed, DE-52 IgG antibody not bound to the insolubilized hemoglobin was separated from insoluble hemoglobin and any material bound thereto using a pasteur pipette and employed in direct binding ELFA assays (see Example 10).

Example 8

Preparation of Human Hemoglobin $A_{1c}$ ($HbA_{1c}$) and Human Hemoglobin $A_o$ ($HbA_o$)

Human $HbA_{1c}$ and $HbA_o$ were purified from outdated blood from a local blood bank. The red blood cells (RBC's) obtained by centrifugation were washed with PBS, pH 7.3, and lysed with 20 parts of distilled water. The residual stroma and cells were removed by centrifugation, and the lysate obtained was subjected to either a modification of the ion exchange-gel filtration method of Lowrey and Soeldner, *Anal. Biochemistry*, 154, 424–430 (1986), or to the ion exchange method of McDonald et al., *J. Biol. Chem.*, 253, 2327–2332 (1987). The method of Lowrey and Soeldner was modified by increasing the column volume (2.5×42 cm), increasing the salt concentration in the lysate loaded (100 mM NaCl), decreasing the flow rate (15 ml/hr) and decreasing the volume of heme protein loaded (0.5 ml of lysate concentrated 10 fold). Although high purity $HbA_{1c}$ and $HbA_o$ were obtained by the mixed bed procedure, the method of McDonald et al. was preferred due to its reproducibility.

Hemoglobin-containing fractions obtained by either isolation technique were identified by inspection and by absorption at 415 nm. The purity of the various hemoglobin fractions was assessed by analytical cation exchange HPLC using a 4.6×30 mM microanalyzer MA7C cartridge (Bio-Rad Laboratories, Richmond, Calif., U.S.A.) in a Beckman 344 HPLC system (Beckman Instruments, Berkeley, Calif., U.S.A.). Hemoglobin fractionation was performed according to the manufacturer's suggested protocol (Bio-Rad Laboratories, Richmond, Calif., U.S.A.). Briefly, 20 ul of a hemoglobin-containing sample was injected on the microanalyzer MA7C cartridge previously equilibrated with 20mM Bis-Tris, pH 6.0, and hemoglobin fractionation was obtained by the use of a linear salt gradient (0 to 100 mM NaCl) in the same Bis-Tris buffer system over 6 minutes at a flow rate of 1.5 ml/min. Hemoglobin containing fractions were detected by heme absorption at 415 nm using a Beckman 163 variable wavelength detector (Beckman Instruments, Berkeley, Calif., U.S.A.). Hemoglobin fractions were detected by absorption at 415 nm and compared to standards containing known amounts of human hemoglobin $A_{1c}$ (Bio-Rad Clinical Division, Richmond, Calif., U.S.A.). Purified hemoglobin fractions were stored at 4° C. until used in direct binding or inhibition ELFA assays (see Examples 10–12).

Example 9

Reduction of Hemoglobin Antigens

To be able to detect and quantitate the $HbA_{1c}$, if any present in hemoglobin-containing samples (e.g., purified hemoglobin, hemoglobin components or RBC lysates from patients), the hemoglobin-containing sample must first be reduced with $NaBH_4$ to form a glucitol-valine on the N-terminal of the beta chains of any $HbA_{1c}$ present in the sample. Reduced $HbA_{1c}$ present in the sample can then react with anti-glucitol-VGG-BSA antibodies present in antisera, in DE-52 IgG fractions of antisera, and in affinity purified and affinity adsorbed materials (all prepared as described in Example 7). Reduction of solid-phase adsorbed hemoglobin is required for detection of glucitol-valine in direct binding ELFA, and reduction of both solid-phase and liquid-phase hemoglobin is required for inhibition ELFA assays (see Examples 10–14). The reduction of solid-phase adsorbed and liquid-phase hemoglobin will be described separately.

Hemoglobin previously adsorbed to polystyrene microtiter wells (see Examples 10–14) was reduced by the addition of 50 mM $NaBH_4$ in PBS, pH 7.3. The volume of reducing solution was equal to that used for hemoglobin coating. After reaction overnight at 4° C., the plates were washed 5 times by filling and decanting or aspirating the wells with PBSA (0.01M sodium phosphate buffer containing 0.15M NaCl, 1% BSA, 0.1% Tween 20, 0.02% $NAN_3$, pH 7.3) to remove residual borohydride. The plates were then processed in the manner described in Example 10 by back coating using 1% (wt/vol) ovalbumin in PBS, pH 7.3.

Reduction of liquid-phase hemoglobin samples was accomplished by adding 3 volumes of 50 mM $NaBH_4$ in PBS containing 0.01% BSA, pH 7.3 ("reducing solution"), to each volume of hemoglobin solution to be reduced. The suggested concentration of unreduced hemoglobin using this reduction method is 0.5–1.0 mg/ml as determined by heme adsorption at 415 nm. The hemoglobin was mixed with the reducing solution by vortexing gently, and was then reacted for 3 hours at 37° C., at which time the reduction mixture was diluted 1:10 using PBSA. This dilution lowers the $NaBH_4$ concentration to 3.75 mM $NaBH_4$, a level determined not to interfere with antibody reactivity, and the diluted, reduced material was ready to be employed as the inhibitor in inhibition ELFA (see Example 11).

$NaBH_4$ reduction of hemoglobin obtained from red blood cell (RBC) lysates was performed in a similar manner to that described above for purified $HbA_{1c}$ or $HbA_o$. RBC's washed with physiological saline were lysed by diluting them 1:20 in distilled water. Insoluble debris was removed by settling or centrifugation, and the hemoglobin concentration of collected soluble supernatant lysate was determined. Reduction of solid-phase adsorbed lysate was performed as described above for $HbA_{1c}$. Reduction of liquid-phase lysate differed from the method described above only in the use of an initial concentration of 2 mg/ml of unreduced hemoglobin instead of 0.5–1.0 mg/ml.

The use of whole blood lysates (Examples 13 and 14) required variations in the reduction protocol which are described in detail in those examples.

Example 10

Direct Binding Enzyme Linked Fluorescence Assay ("Direct Binding ELFA")

Two hundred microliters of antigen (e.g., glucitol-VGG-BSA, glucitol-VGG-Thyro, glucitol-human hemoglobin, $CNBH_3$ control, $HbA_{1c}$, $HbA_o$, or lysates of RBC's from diabetic patients prepared as described in Examples 1–6 and 8–9) were added to wells of Microfluor "B" black polystyrene microtiter plates (Dynatech Laboratories, Alexandria, Va., U.S.A.). The plates were incubated for 2 hours at 37° C. to allow the antigen to adsorb to the wells. The antigens were added at a coating concentration of 5 ug/ml protein in 0.1M $NaHCO_3$, pH 9.8.

Unbound antigen was removed by decanting or aspirating, and $NaBH_4$ reduction was performed as described in Example 9 on adsorbed antigens requiring preliminary reduction (i.e. $HbA_{1c}$, $HbA_o$ and RBC lysates). The plates were washed 5 times with PBSA by filling the wells with PBSA and decanting or aspirating to remove residual $NaBH_4$. The reduction and PBSA washing steps were omitted for antigens already bearing glucitol.

Remaining polystyrene protein binding sites were subsequently blocked by filling wells with PBS containing 1% ovalbumin (Sigma Chemical Co., St. Louis, Mo., U.S.A.) and 0.02% sodium azide, pH 7.3, and incubating for 1 hour at 37° C. After decanting or aspirating, 200 ul of anti-glucitol-VGG-BSA antibody preparation (e.g., antiserum, DE-52 IgG fraction, affinity purified antibody, or affinity adsorbed antibody, all prepared as described in Example 7) serially diluted in PBSA were added to wells and incubated overnight at 4° C. in a humidified chamber.

The microtiter wells were next washed 5 times with PBSA as described above, and 200 ul/well of biotin labeled goat anti-rabbit IgG (Vector Laboratories, Burlingame, Calif., U.S.A.) diluted 1:2000 in PBSA were added and allowed to incubate for 2 hours at 37° C. Following five PBSA washes, 200 ul/well of streptavidin-β-galactosidase (Bethesda Research Laboratories, Gaithersburg, Md., U.S.A.) diluted 1:2000 in PBSA were added and allowed to incubate 1.5 hour at 37° C. After a final five washes with PBSA, 200 ul of 0.1 mg/ml 4-methyl-umbelliferyl-β-D-galactopyranoside substrate in PBS, pH 7.5, were added to the wells of the microtiter plate, and methylumbelliferone fluorescence was measured as relative fluorescence units (RFU) using an excitation wavelength 365 nm and an emission wavelength of 450 nm in a MicroFLUOR reader (Dynatech Instruments, Torrance, Calif., U.S.A.).

Control wells which were treated in an identical manner as described above but lacked only antigen ("without antigen controls"), lacked only anti-glucitol-VGG-BSA antibody preparation ("without primary antibody controls") and those that received only a blocking step and substrate ("substrate blank") were included. Without antigen controls and without primary antibody controls served to correct readings for non-specific binding of antibody and labeling reagents, while substrate controls corrected for non-enzymatic substrate hydrolysis.

The above protocol was modified slightly for direct binding assay of RBC lysate preparations. The alterations for RBC lysates were: the use of a coating concentration of 10 ug/ml protein with no subsequent blocking step; the use of 3 PBS, pH 7.3, washes instead of 5 PBSA washes; incubation of all reagents at ambient temperature for 1 hour, except for a 0.5 hour incubation with streptavidin-β-galactosidase; and the use of anti-glucitol-VGG-BSA antibody preparation at a fixed saturating concentration (1:100 dilution).

Representative direct binding ELFA results are shown in FIGS. 1–3 and 5–7. The results may be summarized as follows.

Figure 2:
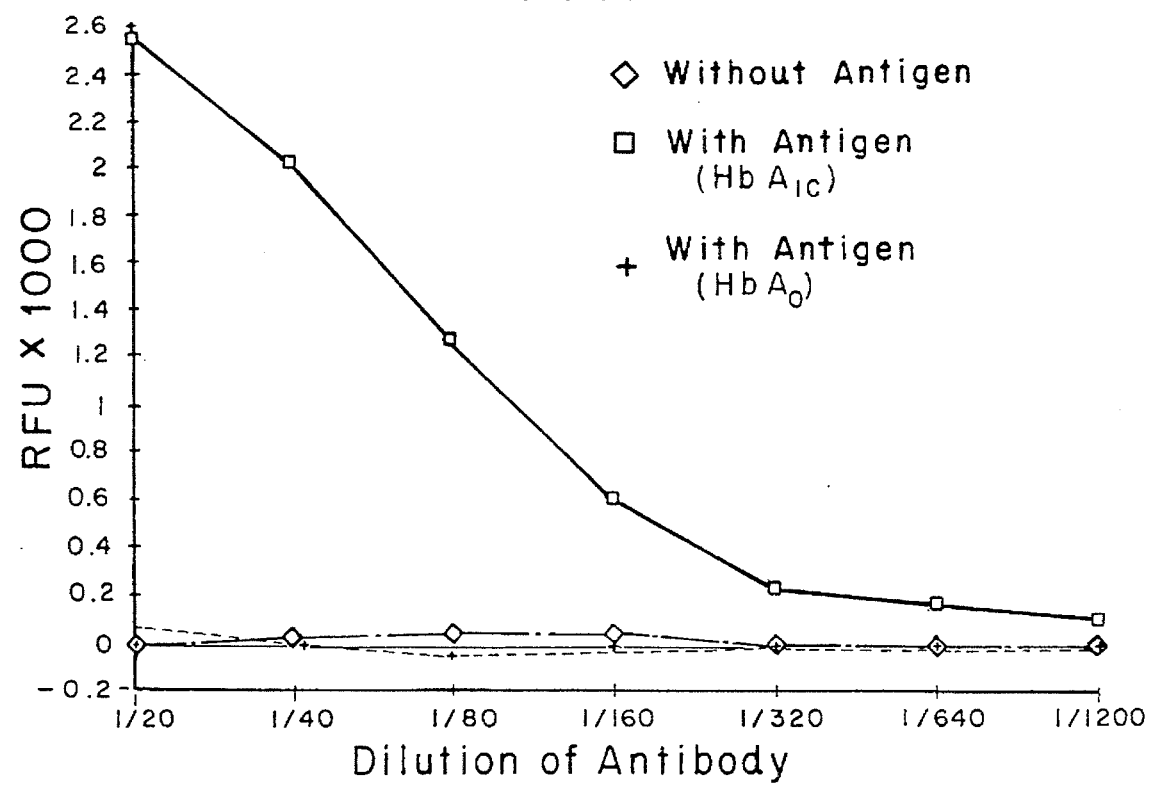
Figure 3:
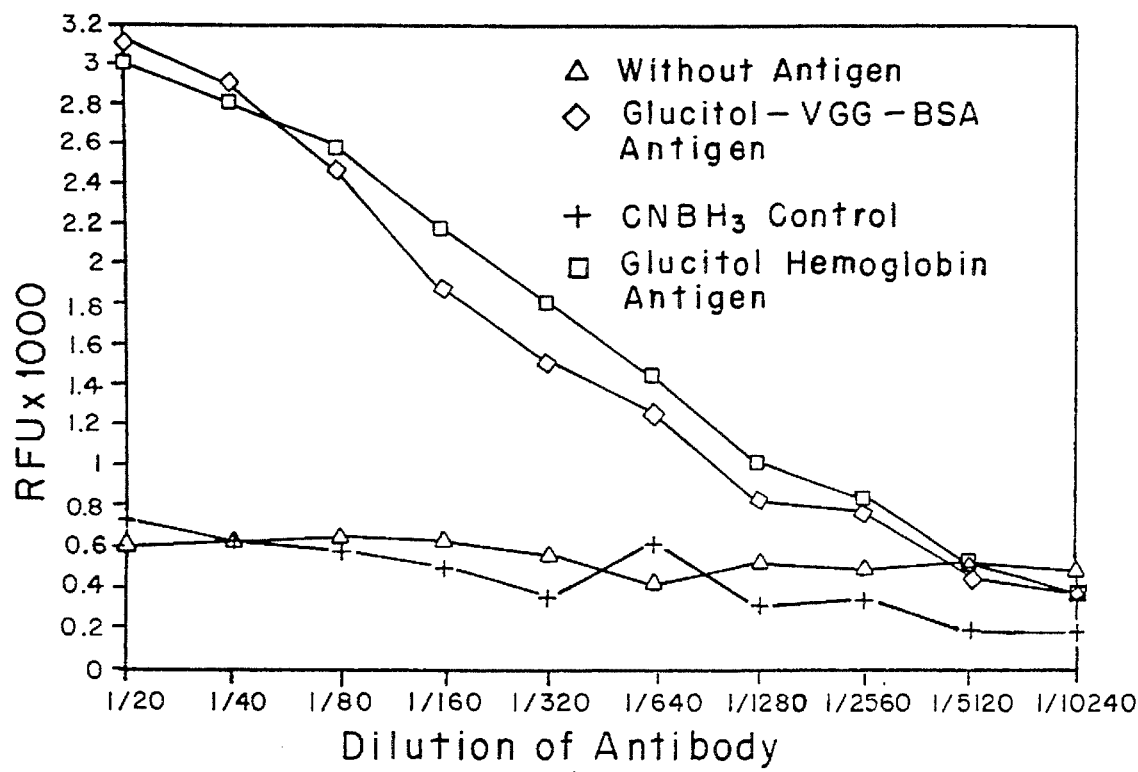

Antibodies prepared against glucitol-VGG-BSA and affinity purified using glucitol-VGG Sepharose recognized glucitol-VGG-BSA and glucitol-VGG-Thyro (FIGS. 1 and 3). These antibodies also reacted with reduced glycosylated native hemoglobin (FIG. 3) and reduced purified $HbA_{1c}$ (FIG. 2), but did not react with reduced $HbA_o$ (FIG. 2) or $CNBH_3$ control (hemoglobin reductively glycated in the absence of glucose in FIG. 3). The $HbA_o$ used was prepared by ion exchange chromatography and would be expected to contain molecules glycosylated on available epsilon amino groups which are reduced by the $NaBH_4$ treatment.

Figure 5:
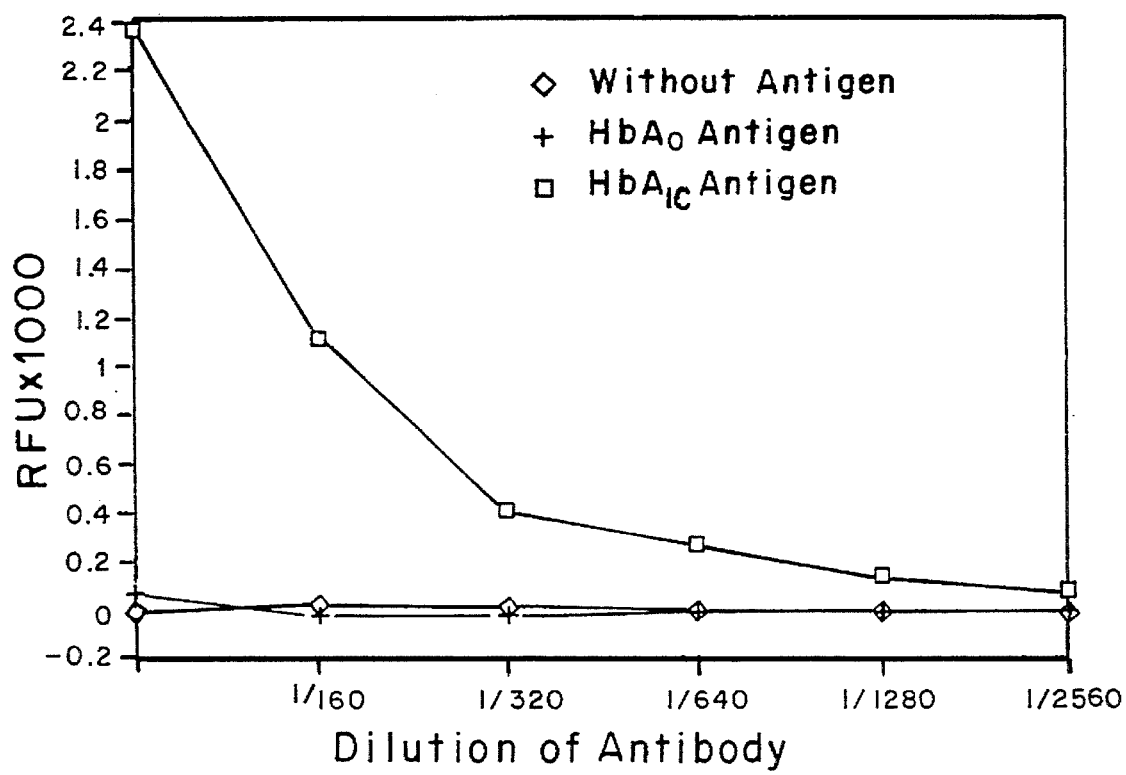
FIG. 5: A graph of RFU versus antibody dilution. The data on the graph were obtained by performing an ELFA utilizing anti-glucitol-VGG-BSA antibodies which had been affinity purified on a column of glucitol-valine Sepharose. The antigens are as indicated.
Figure 6:
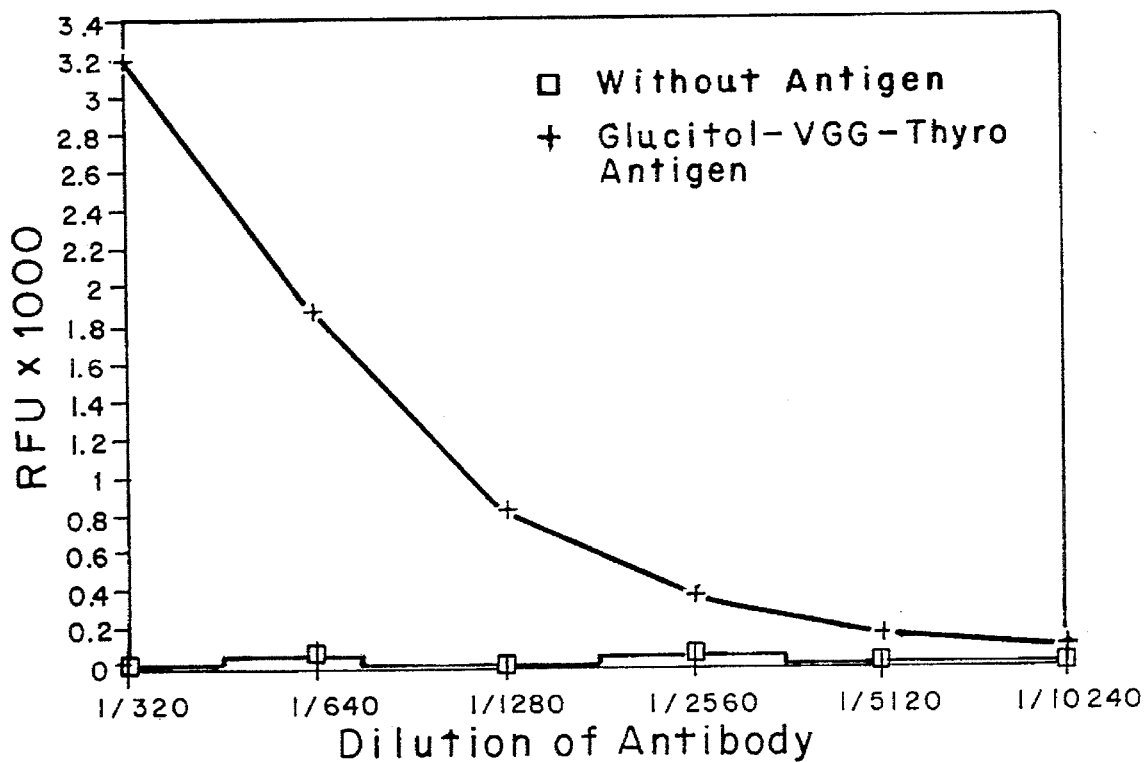
FIGS. 6–7: Graphs of RFU versus antibody dilution. The data on the graph were obtained by performing an ELFA utilizing anti-glucitol-VGG-BSA antibodies which had been affinity absorbed with crosslinked human hemoglobin. The antigens are as indicated.
Figure 7:
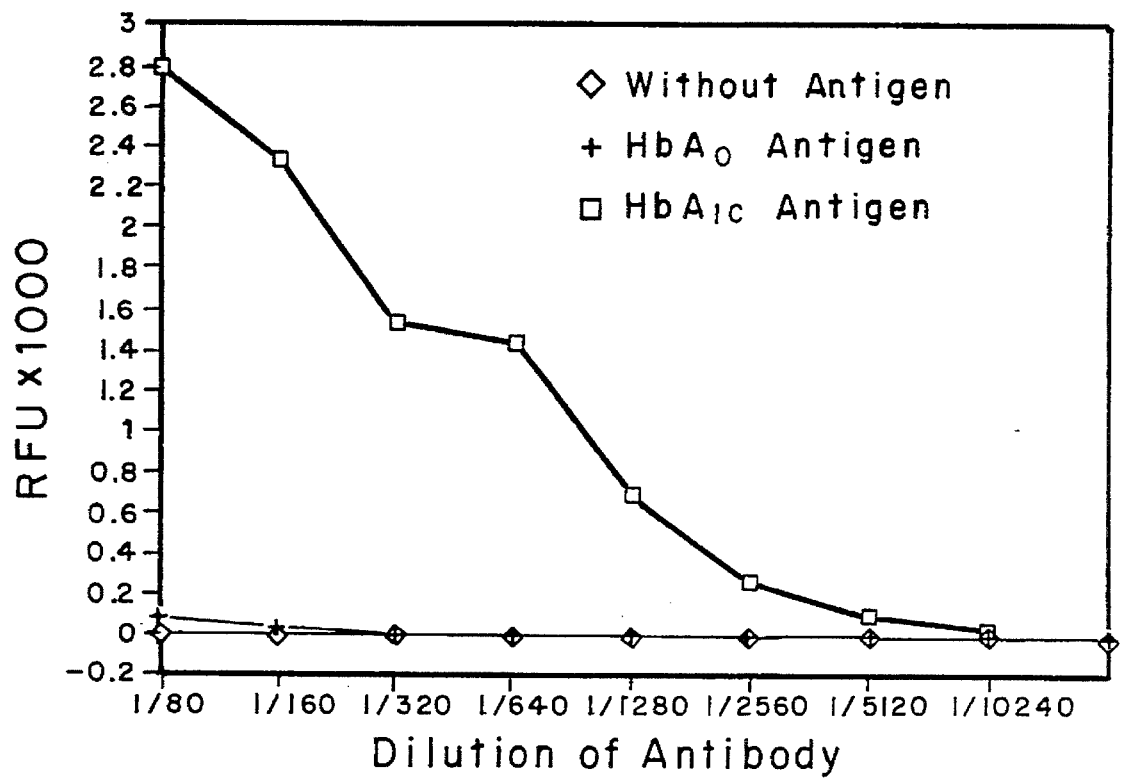

Antibodies prepared using glucitol-VGG-BSA and affinity purified with columns of glucitol-valine-Sepharose showed the same specificities as antibodies purified on glucitol-VGG Sepharose (compare FIG. 2 with FIG. 5). Similarly, antibodies prepared against glucitol-VGG-BSA and affinity adsorbed using cross-linked human hemoglobin (which could be expected to contain unreduced glycosylated valine and lysine residues) showed the same specificities as antibodies that had been affinity purified with either glucitol-VGG Sepharose or glucitol-valine Sepharose. See FIGS. 1–3 and 5–7.

Figure 4:
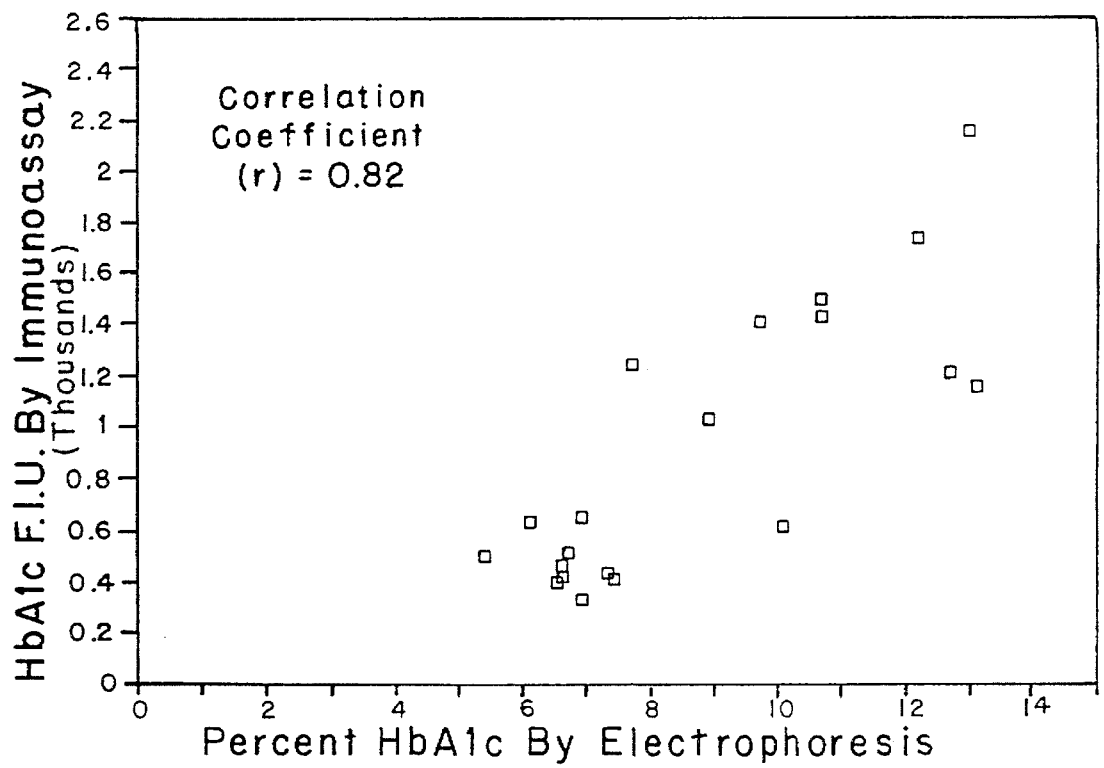
FIG. 4: A typical graph of regression analysis results. The amount of $HbA_{1c}$ detected by electrophoresis in lysates of red blood cells (RBC) from diabetics is on one axis, and the amount detected by direct binding ELFA utilizing anti-glucitol-VGG-BSA antibodies which had been affinity purified on a column of glucitol-VGG Sepharose is on the other axis.

Finally, direct binding ELFA results using RBC lysates from diabetic patients correlated well with the measurement of $HbA_{1c}$ obtained independently using a standard electrophoresis assay. See FIG. 4 which is a typical regression analysis curve.

The electrophoresis assay was performed using a Ciba-Corning electrophoresis kit for the measurement of glycosylated hemoglobin (Ciba-Corning, Palo Alto, Calif., U.S.A., catalog no. 470055). The electrophoresis assay was performed according to the manufacturer's instructions.

Example 11

Inhibition Enzyme Linked Fluorescence Assay ("Inhibition ELFA")

Inhibition ELFA was performed in the same manner as direct binding ELFA of Example 10 using solid-phase adsorbed reduced $HbA_{1c}$ antigen with two alterations. First, a constant concentration was employed of anti-glucitol-VGG-BSA antibody affinity purified on glucitol-VGG Sepharose. The concentration used was the concentration of antibody required to obtain 50% or less of maximal binding in direct binding ELFA with solid phase adsorbed, NaBH4-reduced $HbA_{1c}$ antigen.

Second, antibody of fixed concentration was mixed with varying concentrations of inhibitor consisting of $HbA_{1c}$ antigen or lysates of RBC's from diabetic patients, both of which had previously been reduced as described in Example 9 and then serially diluted in PBSA prior to the addition of antibody. After a 2 hour incubation at 37° C., 200 ul of the antibody-inhibitor mixture were added to wells that had been coated with $HbA_{1c}$, reduced with NaBH4, washed with PBSA and blocked with ovalbumin as described in Examples 9 and 10. The addition of the antibody-inhibitor mixture in inhibition binding ELFA corresponds to the addition of anti-glucitol-VGG-BSA antibody preparation in direct binding ELFA.

Controls for inhibition ELFA were without antigen controls, without primary antibody controls, substrate blank and controls for the effect of $NaBH_4$ reduction consisting of antibody and diluted reducing mixture which had been treated identically to liquid-phase reduced $HbA_{1c}$ inhibitor, but which lacked inhibitor.

Figure 8:
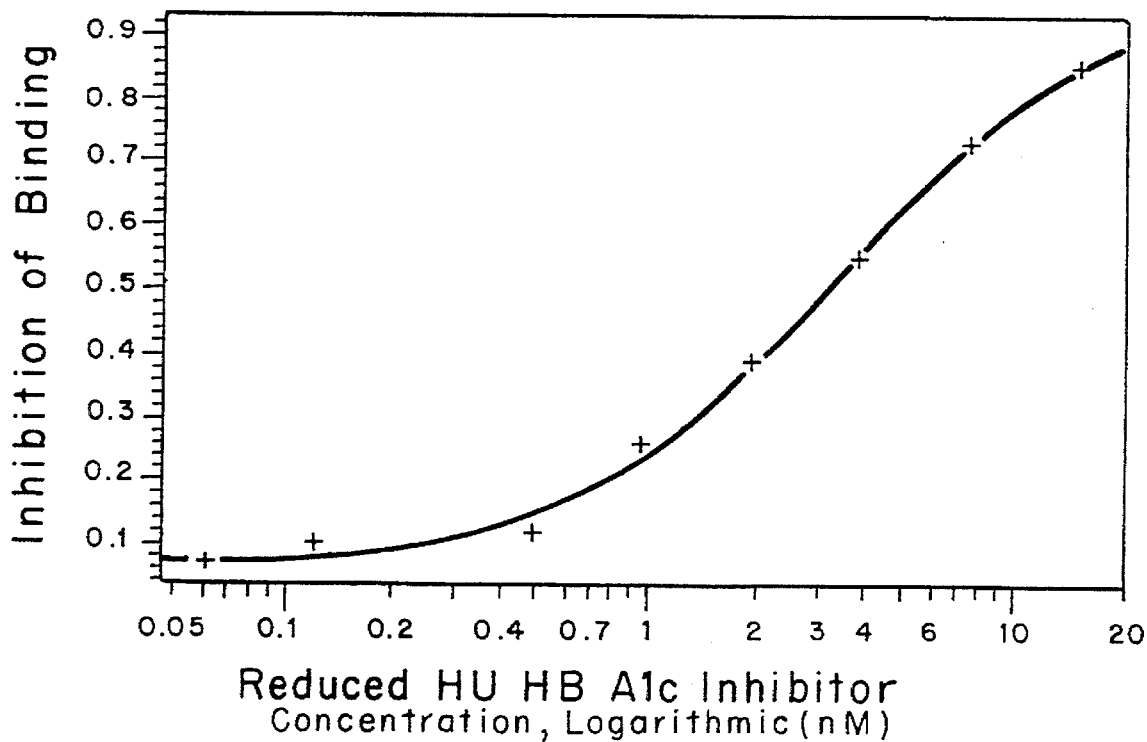
FIG. 8: A graph showing the inhibition by reduced $HbA_{1c}$ of the binding of affinity-purified antiglucitol-VGG-BSA antibodies to reduced $HbA_{1c}$. The antibodies had been affinity purified on a column of glucitol-VGG Sepharose.
Figure 9:
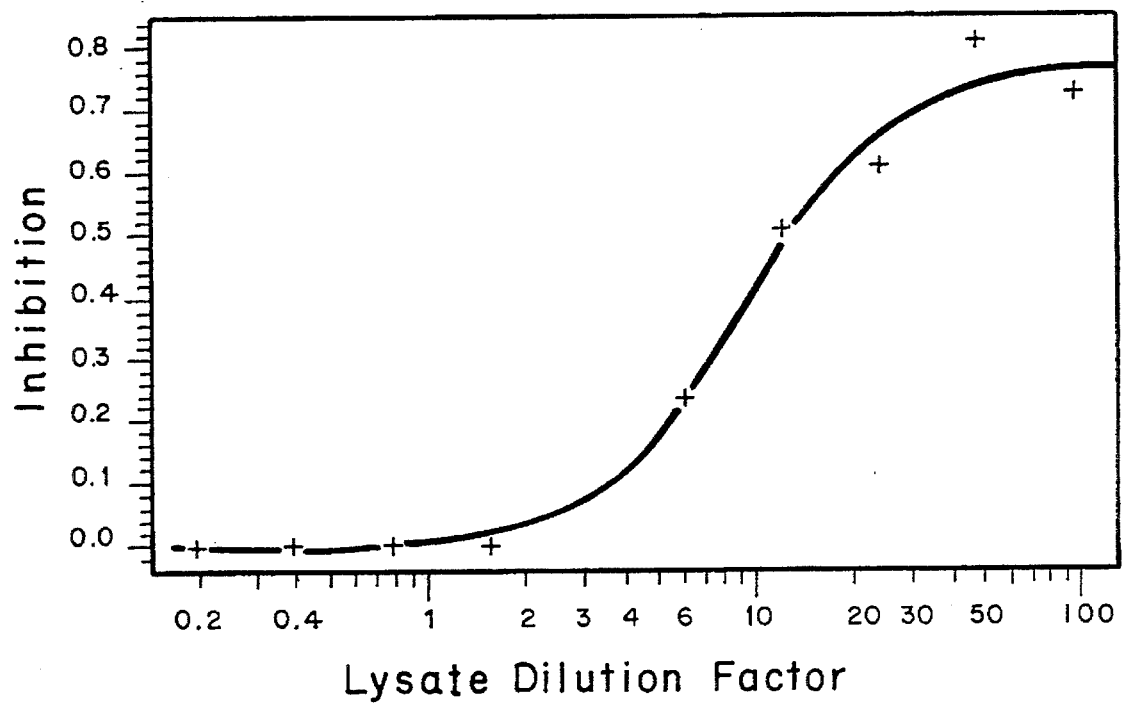
FIG. 9: A graph showing the inhibition, by a reduced lysate of RBC's from a diabetic patient, of the binding of affinity-purified anti-glucitol-VGG-BSA antibodies to reduced $HbA_{1c}$. The antibodies had been affinity purified on a column of glucitol-VGG Sepharose.
Figure 10:
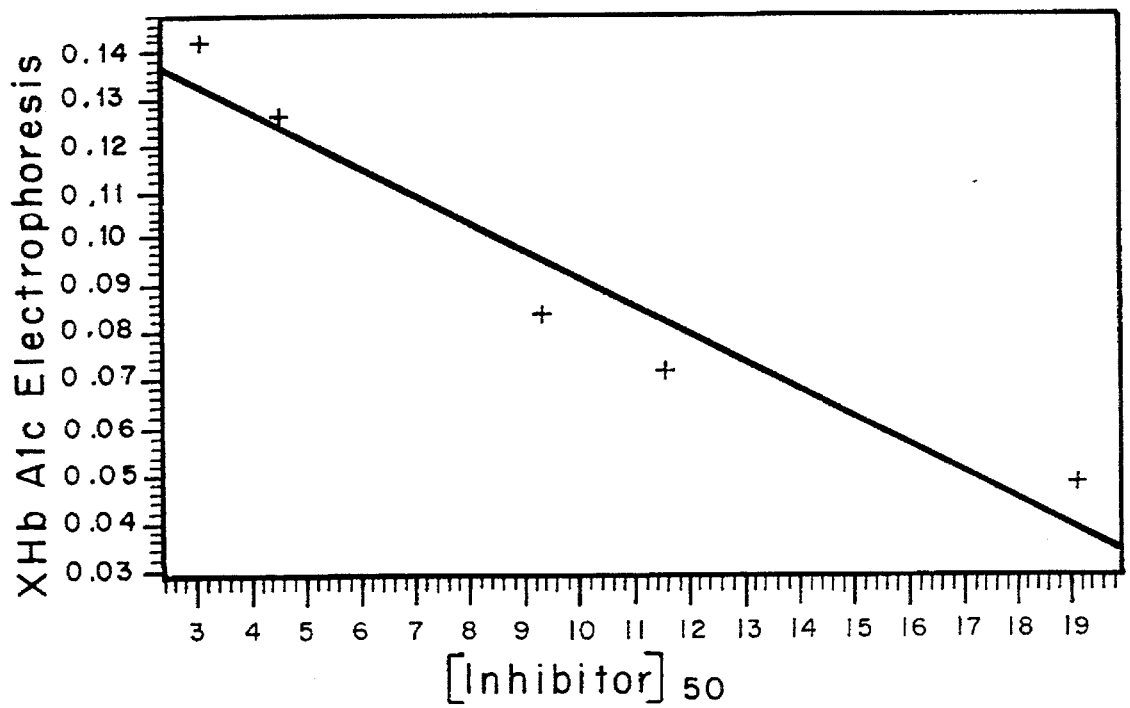
FIG. 10: A graph of regression analysis results. The amount of $HbA_{1c}$ detected in lysates of RBC's from diabetics by electrophoresis is on the one axis, and the concentration of inhibitor necessary to cause a 50% inhibition of the binding of affinity-purified anti-glucitol-VGG-BSA to reduced $HbA_{1c}$ in an inhibition ELFA assay is on the other axis. The inhibitor was reduced RBC lysates. The antibodies had been affinity purified on a column of glucitol-VGG Sepharose.

Representative inhibition of antibody binding is shown in FIG. 8 for reduced liquid phase $HbA_{1c}$ and in FIG. 9 for a reduced RBC lysate sample from a diabetic patient. The RBC lysate had previously been shown by electrophoresis to contain 8.4% $HbA_{1c}$. Regression analysis demonstrates a linear correlation between the amounts of RBC lysate required to obtain 50% inhibition in inhibition ELFA and the amount of $HbA_{1c}$ determined by electrophoresis to be present in that sample for the five samples studied (see FIG. 10).

Example 12

Inhibition Enzyme Linked Fluorescence Assay ("Inhibition ELFA")

Figure 11:
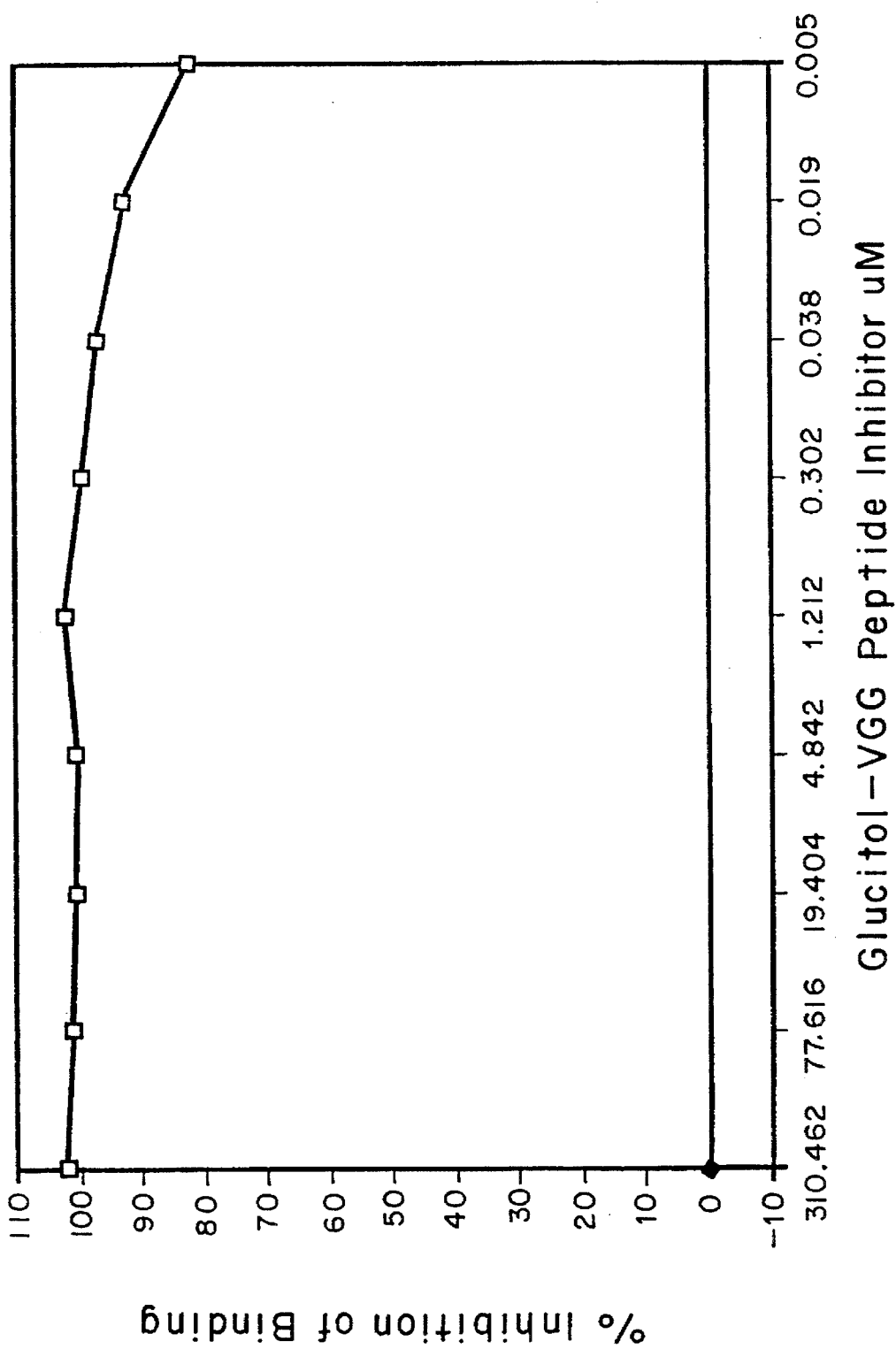
FIG. 11: A graph showing the inhibition by glucitol-VGG of the binding of affinity-absorbed anti-glucitol-VGG-BSA antibodies to reduced $HbA_{1c}$. The antibodies had been affinity absorbed with cross-linked human hemoglobin.

Example 11 was repeated, except that anti-glucitol-VGG-BSA antibody absorbed with cross-linked human hemoglobin was used as the antibody and glucitol-VGG was used as the inhibitor. The results are shown in FIG. 11. As can be seen there, glucitol-VGG inhibited 100% of the binding of the antibody to reduced $HbA_{1c}$ at the higher concentrations of glucitol-VGG tested.

The data from Examples 10–12 taken together demonstrate that anti-glucitol-VGG-BSA antibody which has been affinity purified with glucitol-VGG Sepharose or glucitol-valine Sepharose or affinity absorbed with cross-linked human hemoglobin specifically detects glucitol-valine. The affinity purified or affinity absorbed antibody still has a high titer. Thus, the method of the invention provides an easy way to obtain highly specific, high-titered antisera and antibody preparations useful in immunoassays to detect proteins glycosylated on their N-terminal amino acid without the preparation of monoclonal antibodies. Of course, monoclonal antibodies may be used, if desired.

Example 13

Direct Binding Enzyme Linked Immunosorbent Assay (ELISA) Using Whole Blood Lysates This example describes a direct binding assay which is an adaptation of the method described in Example 10. Whole blood is used as a source of $HbA_{1c}$, and a readily visualized colorimetric endpoint is employed. The complete assay can be performed in a total of about 3–4 hours.

One drop of blood previously collected in EDTA coated vacutainer tubes (Becton Dickinson, Rutherford, N.J. 07070) was added to 1 ml of distilled water in a 12×75 mm polystyrene tube (Scientific Products, McGaw Park, Ill., U.S.A.) with a 5.75 inch Pasteur-type Dispo Pipet (Scientific Products, McGaw Park, Ill., U.S.A.). After mixing, the tube was coated with the resulting whole blood lysate by incubating for 15 minutes at room temperature. The coating solution was removed by aspiration, and one ml of 50 mM $NaBH_4$ in PBS was added, and reduction was allowed to proceed for 10 min. at room temperature.

The tube was then washed three times with PBS. Washing consisted of filling the tube with PBS and then aspirating the wash buffer.

Anti-glucitol-valine reactive antibody (prepared as described in Example 7, except that it was not affinity purified or affinity absorbed, i.e., a DE-52 purified IgG fraction), diluted 1:100 in PBSA was added (1 ml per tube) and allowed to incubate for 45 min. at room temperature.

Following three washes with PBS, one ml of biotin-labeled goat anti-rabbit IgG (Vector Laboratories, Burlingame, Calif., U.S.A.) diluted 1:2000 in PBSA was added and allowed to incubate for 0.5 hours at room temperature. After three PBS washes, one ml of streptavidin-beta-galactosidase (Bethesda Research Laboratories, Gaithersburg, Md., U.S.A.) diluted 1:2000 in PBSA was added and allowed to incubate for 15 min. at room temperature. Following four PBS washes, 1 ml of a 4 mg/ml solution of o-nitrophenyl-beta-D-galactopyranoside (ONPG) substrate (Sigma Chemical Co., St. Louis, Mo., U.S.A.) in 0.1M sodium phosphate buffer, pH 7.3, containing 0.1M 2-mercaptoethanol and 5 mM $MgCl_2$ was added and allowed to incubate 40 minutes at room temperature. Using standards containing known amounts of $HbA_{1c}$ (Bio-Rad Hemoglobin $A_{1c}$ Mini and/or Micro Column Test Calibrators, Bio-Rad Clinical Division, Hercules, Calif., U.S.A.), the relative amounts of $HbA_{1c}$ in whole blood lysates could be determined by a comparison between standards and whole blood lysates of yellow nitrophenol product obtained.

Figure 12:
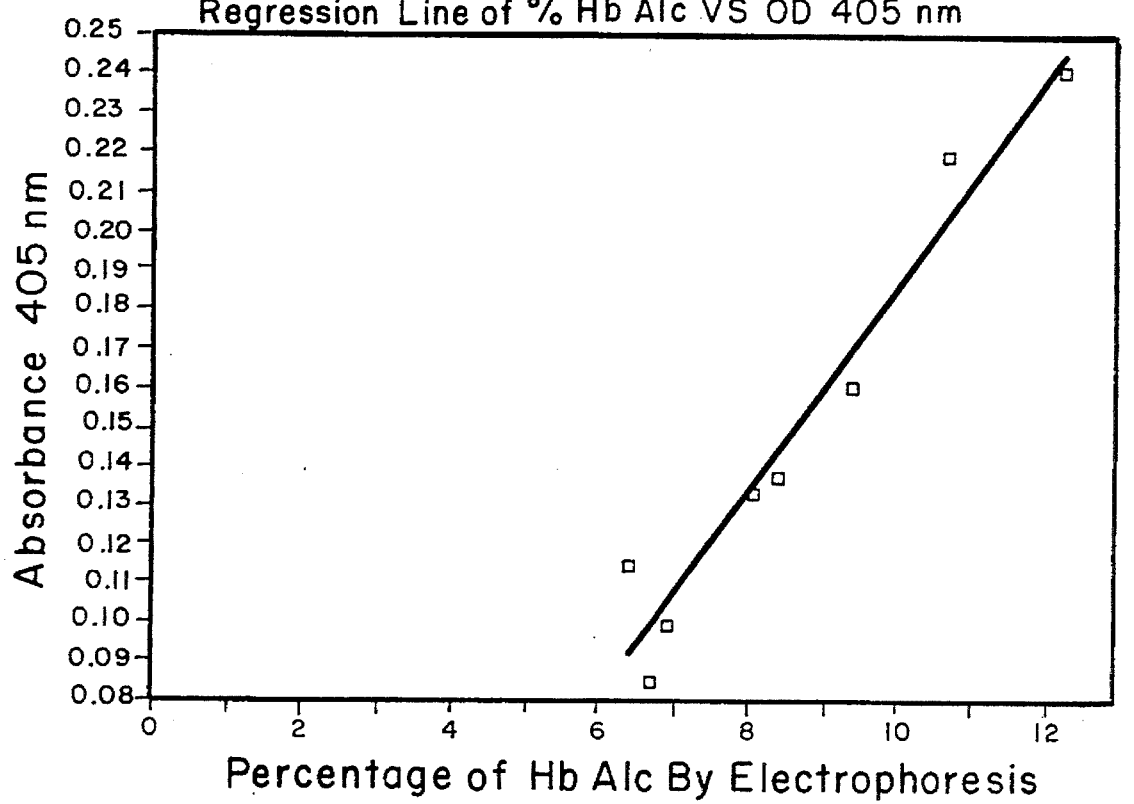
FIG. 12: A graph of regression analysis results. The amount of $HbA_{1c}$ detected by electrophoresis in RBC lysates from diabetics is on one axis and the absorbance detected by direct binding ELFA utilizing DE-52 purified anti-glucitol-VGG-BSA and reduced whole blood lysates from the same diabetics is on the other axis.

Results obtained using this method to measure the amount of $HbA_{1c}$ in whole blood lysates from diabetic patients correlated well with the percentage of $HbA_{1c}$ obtained by electrophoresis of RBC lysates from the same patients as shown in FIG. 12 (correlation coefficient=0.9724). The electrophoresis assay was performed as described in Example 10.

Example 14

Inhibition Enzyme Linked Fluorescence Assay Using Whole Blood Lysates as Inhibitors This example describes an adaptation of the inhibition assay format described in Example 11. Whole blood lysates were used as the source of $HbA_{1c}$.

Two hundred microliters of antigen (Bio-Rad Hemoglobin $A_{1c}$ Micro Column Test Standard assayed to contain 11.4% $HbA_{1c}$) was added to Microfluor "B" microtiter wells at a concentration of 10 µg/ml of total hemoglobin in 0.1M $NaHCO_3$, pH 9.8, and allowed to coat the wells for 2 hours at 37° C. Unbound antigen was removed by decanting or aspirating, and adsorbed antigen was reduced by filling the wells with 50 mM $NaBH_4$ in PBS and incubating for 1 hour at 37° C. Wells were subsequently washed 5 times with PBS containing 0.1% Tween 20 (Sigma Chemical Co., St. Louis, Mo., U.S.A.) and filled with PBS containing 1% ovalbumin (Sigma Chemical Co., St. Louis, Mo., U.S.A.) and 0.02% sodium azide, pH 7.3, and allowed to incubate for 1 hour at 37° C. to block any remaining polystyrene protein binding sites.

During the coating, reducing and backcoating steps, anti-glucitol-valine reactive antibody, prepared as described in Example 13, was incubated with $NaBH_4$-reduced inhibitors (either whole blood lysates or standards consisting of Bio-Rad Hemoglobin $A_{1c}$ calibrators, Bio-Rad Clinical Division, Hercules, Calif., U.S.A.). Reduction of these inhibitors was performed as described in Example 9 for RBC lysates, except that the concentration of $NaBH_4$ in the reducing solution was 500 mM and the reduction period was 1 hour at 37° C.

Subsequent assay steps of the inhibition assay were identical to those previously described in Example 11 with the following exceptions:

(1) Washes were done with PBS containing 0.1% Tween 20; and (2) The incubation period with biotin-labeled goat anti-rabbit IgG was overnight at 4° C.

Figure 13:
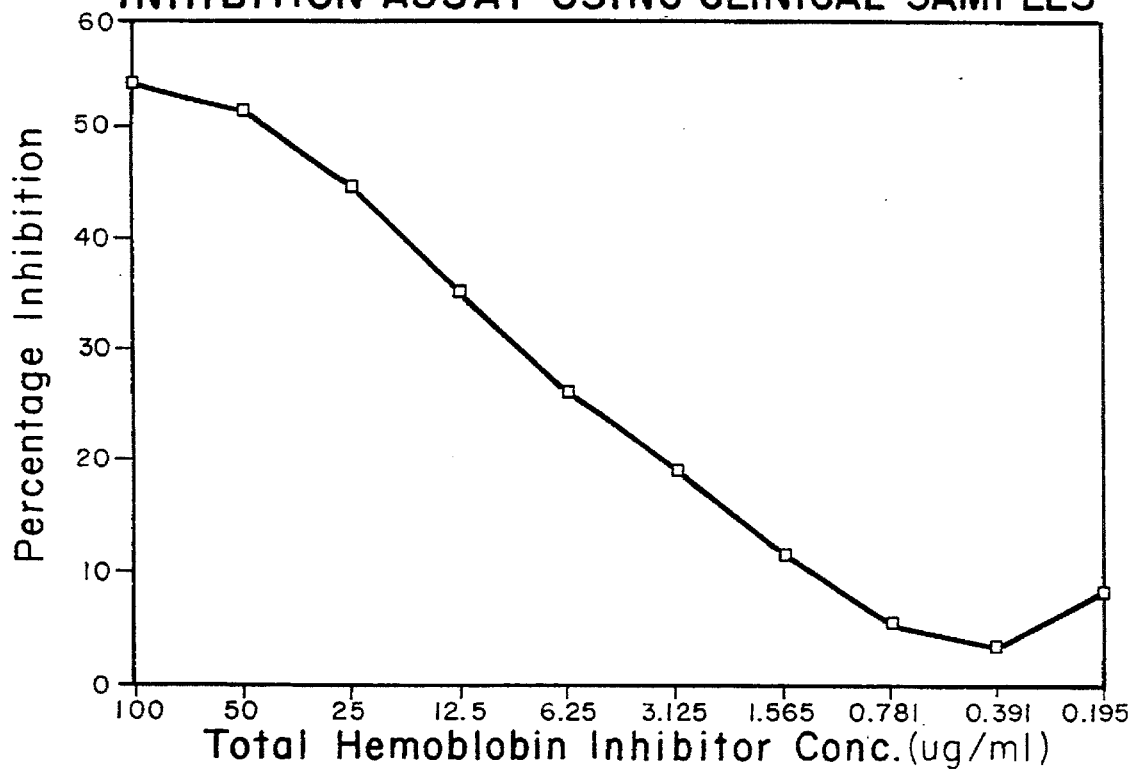
FIG. 13: A typical graph showing the inhibition by reduced whole blood lysates of the binding of DE-52 purified anti-glucitol-VGG-BSA antibodies to reduced $HbA_{1c}$.
Figure 14:
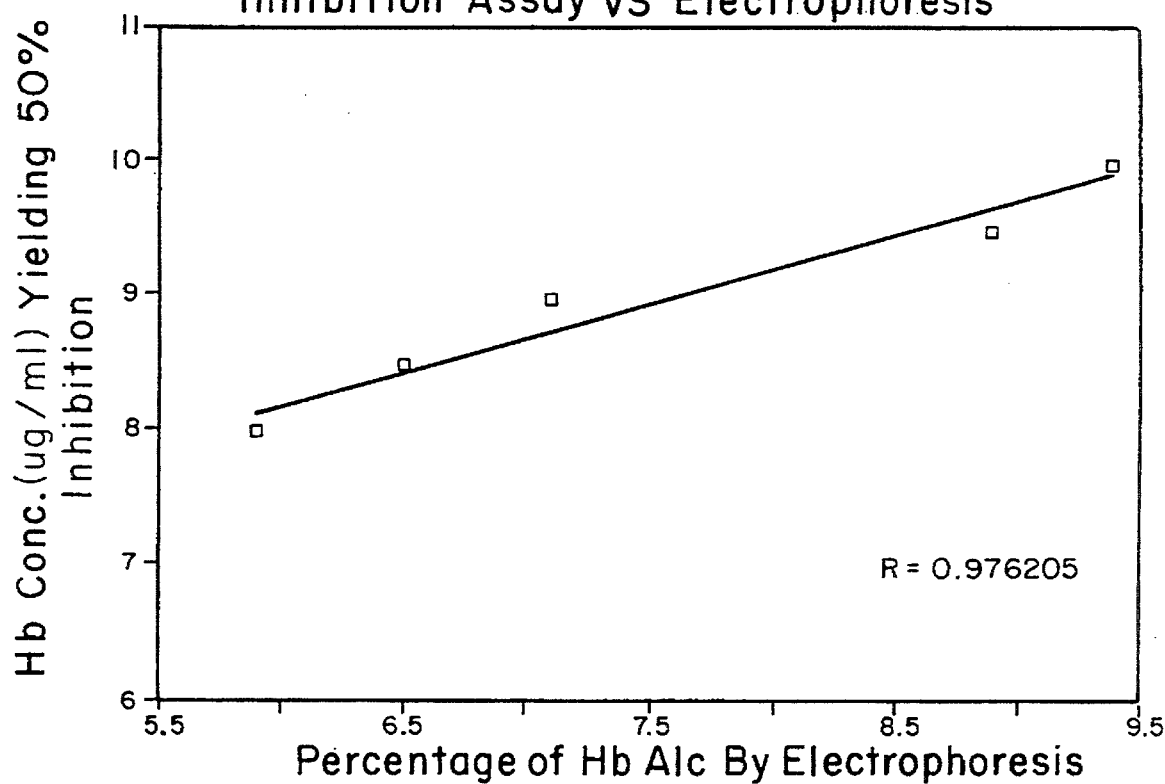
FIG. 14: A graph of regression analysis results. The amount of $HbA_{1c}$ detected by electrophoresis in RBC lysates from diabetics is shown on one axis, and the amount of reduced whole blood lysate (expressed as total hemoglobin concentration in the lysate) from the same diabetics required to give 50% inhibition of the binding of DE-S2 purified anti-glucitol-VGG-BSA antibodies to reduced $HbA_{1c}$ is on the other axis.

A representative dose response curve showing inhibition of antibody binding using a diabetic whole blood lysate as inhibitor is shown in FIG. 13. Regression analysis was performed comparing the results of measuring the amount of $HBA_{1c}$ in whole blood lysates from diabetics by the described inhibition method with the results obtained by electrophoresis of RBC lysates from the same patients (electrophoresis was done as described in Example 10). A graph of the regression analysis results comparing the two techniques for 5 of the 8 diabetic samples tested are shown in FIG. 14. The correlation coefficient for these five samples was 0.9762. Regression analysis of 6 of the 8, 7 of the 8, and 8 of the 8 samples gave, respectively, correlation coefficients of 0.7098, 0.4899 and 0.0774. It is not yet known why these three samples gave such divergent results.

In FIGS. 13 and 14, the hemoglobin concentration of the whole blood lysates was determined by comparison of the absorbance of the lysates at 414 nm with the absorbance of a serially diluted hemoglobin standard (Sigma Chemical Co., St.Louis, Mo., U.S.A.) dissolved and diluted in distilled water.

Example 15

Direct Binding Enzyme Linked Immunosorbent Assay (ELISA) Using Whole Blood Lysates Direct binding ELISA using whole blood lysates as a source of $HBA_{1c}$ was performed using microtiter plates. The complete assay can be performed in a total of about 3–4 hours.

Blood samples were lysed by dilution to 1:200 in distilled water, and the hemoglobin concentration was subsequently adjusted to 10 µg/ml in 0.1M $NaHCO_3$, pH 9.6 ("coating buffer"). Hemoglobin concentrations were determined by comparison of the absorbance of the lysates at 414 nm with the absorbance of a serially diluted hemoglobin standard (Sigma Chemical Co., St. Louis, Mo., U.S.A.) dissolved and diluted in distilled water. Standards containing known amounts of hemoglobin $A_{1c}$ (Bio-Rad Hemoglobin $A_{1c}$ Mini and/or Micro Column Test Calibrators, Bio-Rad Clinical Division, Hercules, Calif., U.S.A.) were diluted to 10 µg/ml in coating buffer.

Two hundred microliters of antigen (i..e., diluted diabetic whole blood lysates or diluted standards containing known amounts of hemoglobin $A_{1c}$) were added to wells of Immulon 2 plates (Dynatech Laboratories, Inc., Chantilly, Va., U.S.A.). The plates were incubated for 1 hour at 37° C. to allow the antigen to adsorb to the solid surfaces of the wells. The antigens were added at a coating concentration of 10 µg/ml in coating buffer.

Subsequent steps were identical to those used in the direct binding ELFA described in Example 10, with the following exceptions:

1. Reduction with 50 mM $NaBH_4$ in PBS, pH 7.3, was for 0.5 hours at room temperature;
2. Incubation with anti-glucitol-valine antibody (prepared as described in Example 13) was for 45 minutes at 37° C. using a 1/20 dilution of antibody;
3. Incubation with biotin-labeled goat anti-rabbit IgG was for 45 minutes at 37° C. using a 1/2000 dilution of antibody;
4. Incubation with streptavidin-β-galactosidase was for 20 minutes at room temperature;
5. All washes between addition of reagents were performed in triplicate using PBS containing 0.1% Tween 20, pH 7.3;
6. Substrate was either: a) o-nitrophenyl-β-D-galactopyranoside ("ONPG") (Sigma Chemical Co., St. Louis, Mo., U.S.A.) at a concentration of 1 mg/ml in 0.1M sodium phosphate buffer, pH 7.3, containing 0.1M 2-mercaptoethanol and 5 mM $MgCl_2$ ("colorimetric substrate buffer"); or b) chlorophenol red-β-D-galactopyranoside ("CPRG") (Boehringer Mannheim Biochemicals, Indianapolis, Ind., U.S.A.) at a concentration of 0.6 mg/ml in colorimetric substrate buffer; and
7. After 40 minutes reaction with ONPG substrate, absorbance at 405 nm was measured. For CPRG, the reaction time was 9 minutes, and absorbance at 570 nm was measured.

Figure 15:
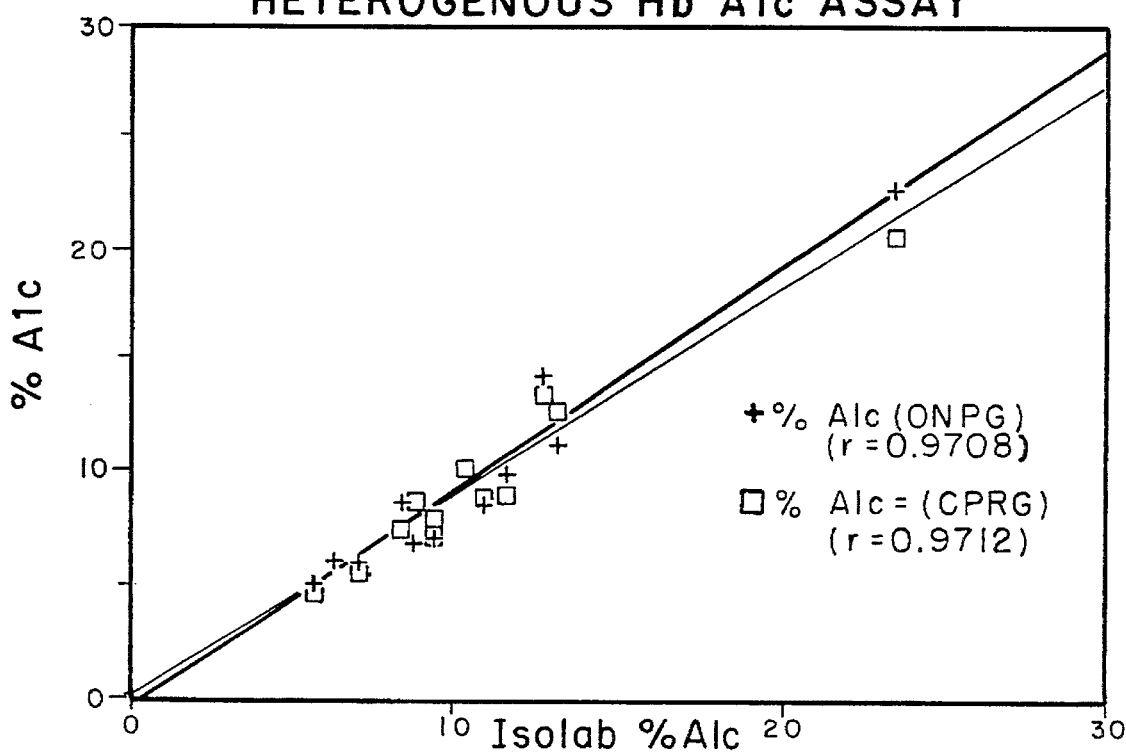
FIG. 15: A graph of regression analysis results. The amount of $HbA_{1c}$ detected by the aminophenylboronate column method in RBC lysates from diabetics is on one axis, and the amount of $HbA_{1c}$ detected in whole blood lysates from the same patients by direct binding ELISA utilizing DE-52 purified antiglucitol-VGG-BSA antibody is on the other axis.

FIG. 15 shows a comparison of the results obtained by measuring $HbA_{1c}$ in whole blood lysates from diabetics using the direct binding ELISA with those obtained using an aminophenyl boronate system (Glyc-Aff-Ghb, Isolab Inc., Akron, Ohio, U.S.A.), performed according to the manufacturer's instructions, to measure $HbA_{1c}$ in RBC lysates from the same patients. The percentages of $HbA_{1c}$ obtained using the direct binding ELISA and those obtained using the Isolab aminophenyl boronate column system were similar for both ONPG (correlation coefficient=0.9708) and CPRG (correlation coefficient=0.9712) substrates. See FIG. 15.

Example 16

Preparation of Mannitol-Valine-Glycine-Glycine (Mannitol-VGG)

Mannitol-valine-glycine-glycine (mannitol-VGG) was prepared, isolated and analyzed as described in Example 1 for glucitol-VGG, except that mannose (Sigma Chemical Co., St. Louis, Mo. or Wako Pure Chemical Industries Ltd.) was used instead of glucose. The analyses indicated that the final purified material was mannitol-VGG.

Example 17

Preparation of Mannitol-Valine-Glycine-Glycine-Human Serum Albumin (Mannitol-VGG-HSA) and Mannitol-Valine-Glycine-Glycine-Bovine Serum Albumin (Mannitol-VGG-BSA)

Mannitol-VGG (prepared as described in Example 16) was coupled to human serum albumin (HSA, Sigma Chemical Co., St. Louis, Mo.) as described in Example 3, except that HSA was substituted for the BSA. TNBS amino group determination, performed as described in Example 1, of the mannitol-VGG-HSA conjugate and HSA conjugate control (without mannitol-VGG, EDCI or sulfo-NHS) revealed that 50–60% of the HSA amino groups were substituted with mannitol-VGG after conjugation.

Mannitol-VGG (prepared as described in Example 16) was also coupled to BSA as described in Example 3, except that an increased molar amount of the mannitol-VGG reactant and increased reaction volumes were employed. In particular, after pre-cooling all reactants on ice, 937 µl of a 10 mg/ml aqueous solution of sulfo-NHS was added to 500 µl of a 56 mg/ml aqueous solution of mannitol-VGG and mixed. Then, 6.163 ml of a freshly prepared 20 mg/ml solution of EDCI in distilled water were added, mixed immediately and allowed to react on ice for 15 minutes. Subsequently, 4.766 ml of a 5 mg/ml aqueous solution of BSA were added. This reaction solution was mixed, and coupling was continued overnight at 4° C. The reaction mixture was then dialyzed exhaustively at 4° C. against distilled water using Spectropore cellulose dialysis tubing of an average molecular weight cut-off of 12–14K daltons. Coupling controls were identical to those employed in Example 3. Amino acid analysis of the mannitol-VGG-BSA conjugate indicated that 6–9 (10–15%) of the 60 BSA amino groups were substituted with mannitol-VGG after conjugation.

Example 18

Preparation of Polyclonal Anti-Mannitol-VGG-BSA Antibodies

New Zealand white female rabbits (Duncroft Inc., Lovettsville, Va.) were immunized with mannitol-VGG-BSA by the method of Vaitakaitis et al., *Clin. Endo. Metab.*, 33, 988 (1971), with immunogen-adjuvant mixtures being administered both subcutaneously and intradermally at 20 to 40 sites per rabbit. The mannitol-VGG-BSA immunogen was prepared as described in Example 17, and it was employed at a concentration of 1.93 mg/ml in sterile distilled water for all immunizations. The primary immunization consisted of 2 ml of an emulsion of 0.5 ml of mannitol-VGG-BSA immunogen and 0.5 ml of sterile water mixed with 1 ml of complete Freund's adjuvant. Secondary immunizations consisted of 0.1 ml of mannitol-VGG-BSA immunogen and 0.9 ml of sterile water mixed with 1.0 ml of incomplete Freund's adjuvant. The immunizations were spaced 14 days apart, and the desired antibody was generally obtained after four (one primary and three secondary) immunizations. Bleedings for antisera were performed 7 days after each immunization by the method of Nerenberg et al., *J. Immunol. Methods*, 24, 19 (1978). Sera obtained were tested for antibody reactivities to hemoglobin $A_{1c}$ by the assay described below in Examples 20 and 21 following IgG fractionation of the sera using batchwise ion-exchange chromatography on DE-52 cellulose (Whatman LTD, Springfield Mill Maidstone Kent, England) by the method of Reif, *Immunochemistry*, 6, 723 (1969). All antisera and IgG fractions of antisera were stored frozen at −20° C. between uses.

Example 19

Preparation of Mannitol-Valine Reactive Monoclonal Antibodies

A. Immunization Of Mice

BALB/cAnN female mice, six weeks old (Charles River Japan Inc., Yokohama, Japan), were initially immunized by subcutaneous injection of 100 µg of mannitol-VGG-HSA (prepared as described in Example 17) emulsified in CFA. The mice were injected subcutaneously four more times at two-week intervals with 100 µg of mannitol-VGG-HSA in CFA. Four days prior to fusion, the mice were injected intraperitoneally with 100 µg of mannitol-VGG-HSA in saline.

B. Cell Fusion And Cloning

Four days after the final immunization, the spleens were removed from the immunized mice, and a suspension of spleen cells was prepared. The spleen cells were washed in RPMI 1640 (GIBCO) and then centrifuged at 1200 rpm for 5 minutes. The supernatant was discarded, and the cells were incubated with 2 ml of red blood cell lysing buffer (Sigma Chemical Co., St. Louis, Mo., No. R7757) for 2 minutes. Then, 15 ml RPMI 1640 were added, and the cells were centrifuged at 1200 rpm for 5 minutes. The supernatant was discarded, and the cells were mixed with the hypoxanthine-quanine phosphoribosyl-transferase-deficient myeloma P3-X63-Ag8.653 (American Type Culture Collection, Rockville, Md.) at a ratio of 10:1 and centrifuged at 1200 rpm for 5 minutes. The supernatant was discarded, and 1 ml of 50% (w/v) polyethylene glycol 4000 (Merck, Rahway, N.J., No. 9727) in RPMI 1640 was added to the cell pellet. Two minutes later, 25 ml of RPMI 1640 were added, and the mixture was centrifuged at 800 rpm for 5 minutes. The cells were resuspended in HAT medium (RPMI 1640 containing 10% fetal calf serum (Hyclone) and hypoxanthine, aminopterin and thymidine (HAT Supplement, GIBCO)) at a ratio of 25 ml per $10^8$ spleen cells, and 100 µl of this cell suspension were added to each well of 96-well Nunc plates (Nunc product no. 1-67008, Trident House, Paisley, United Kingdom). After two weeks of incubation at 37° C., 5% $CO_2$, the supernatants were screened by the ELISA described in section D below. A total of five fusions were performed, and twenty-four positive clones were obtained. Positive clones were those whose absorbance at 490 nm in the ELISA assay was over about 0.4.

The twenty-four positive clones were transferred into a 24-well culture plate (NUNC, catalog no. 1-43982) and incubated at 37° C., 5% $CO_2$, for four days. The supernatants were then screened by the inhibition assay described in section F below using 10 µl of a 1 mg/ml solution of mannitol-VGG as inhibitor and 10 µl of a 1 mg/ml solution of HSA as control. Six positive clones were obtained. In this assay, positive clones were those whose reaction with $HbA_{1c}$ was inhibited by mannitol-VGG.

The six positive clones were further cloned twice by the soft agar method as described in *Antibodies* (Cold Spring Harbor Laboratory 1988). The supernatants were screened by the ELISA assay described in section D below, and three positive clones were obtained. All three of these positive clones were produced by the same fusion.

The three positive clones have been given designations MML01, MML03, and MML05. MML03 was found to produce antibody having the highest titer in the ELISA assay and is, therefore, the preferred hybridoma. Hybridoma MML03 is currently deposited with Berkeley Antibody Co., 4131 Lakeside Drive, Suite B, Richmond, Calif. 94806-1965.

C. Preparation Of Monoclonal Antibodies

Antibodies were produced by culturing a clone (e.g., MML03) in RPMI 1640 complete medium (RPMI 1640 plus 10% fetal calf serum). Alternatively, ascites fluid was prepared by administering 0.5 ml pristane (2,6,10,14-tetramethylpentadecane; Tokyo Kasei Kogyo Co., Ltd., Tokyo, Japan) intraperitoneally to 8-week-old female BALB/cAnN mice 1 to 2 weeks before injecting the mice with $10^7$ hybridoma (e.g., MML03) cells/mouse. Two weeks after injection of the hybridoma cells, ascites fluid was collected from the mice.

In some cases, monoclonal antibody was isolated from the mouse ascites fluid by affinity purification on Protein G Sepharose 4 Fast Flow (Pharmacia Biotech Inc., Piscataway, N.J.). Briefly, 2 ml of Protein G Sepharose 4 Fast Flow slurry was packed into a BioRad polyprep chromatography column (BioRad Laboratories, Richmond, Calif., catalog no. 731-1550) to give a total bed volume of 1.2 ml. The column was first washed with 10 ml distilled water and then with 28 ml of PBS (0.01M sodium phosphate, 0.15M NaCl), pH 7.3. The column was then washed with 5 column volumes of elution buffer (0.1M glycine-HCl, pH 3.0) and immediately equilibrated with 8 column volumes of PBS, pH 6.0. Then, 0.9 ml of mouse ascites fluid was mixed with an equal volume of PBS, pH 6.0, and loaded onto the column at a flow rate of 1 ml per minute. The flow-through material was collected and re-loaded at the same flow rate to insure IgG binding. The column was then washed with 8 column volumes of PBS, pH 6.0, and the IgG-containing fraction was eluted with 4 ml of elution buffer. The eluted material was immediately neutralized by the addition of 4 ml of neutralization buffer (0.1M dibasic sodium phosphate containing 0.15M NaCl, pH 9.2). The eluted, neutralized fraction was subsequently exhaustively dialyzed against 10 liters of PBS, pH 7.3, and was then aliquoted and stored frozen (–20° C.) prior to use.

D. ELISA For Screening Of Antibodies

Ten microliters of whole blood containing 10–12% $HbA_{1c}$ (as measured by the standard HPLC method described below in section G) were added to 90 µl of 50 mM $NaBH_4$ and incubated for 20 minutes at room temperature. Then, 50 ml of 0.1M $NaHCO_3$ were mixed with the hemolysate, and 100 µl/well of the diluted hemolysate were added to the wells of 96-well Nunc-Immuno plates. The plates were incubated for 30 minutes at room temperature, after which the wells were washed 2 times with PBS (3.222 g $Na_2HPO_4(12H_2O)$, 0.156 g $NaH_2PO_4(2H_2O)$, 9 g NaCl, 1 liter distilled water) containing 0.1% Tween 20 (PBS-Tween). Next, 100 µl of sample (hybridoma culture supernatant or ascites fluid diluted with PBSA (1% BSA in PBS)) were added, and the plates were incubated for 30 minutes at room temperature. After 3 washes with PBS-Tween, 100 µl of peroxidase-labelled, affinity-purified goat anti-mouse IgG antibody (Organon Teknika N.V., Cappel Products, U.S.A.) diluted 1000-fold with PBSA were added per well, and the plates were incubated for 30 minutes at room temperature. After 5 washes with PBS-Tween, 100 µl of OPD (o-phenylenediamine dihydrochloride) substrate solution (preparation described below) were added per well, and the plates were incubated for 30 minutes at room temperature. Finally, 200 µl of 2N $H_2SO_4$ were added, and the absorbance at 490 nm was measured on a Dynatech MR700 microplate reader (Dynatech Laboratories, Inc., Chantilly, Va.). OPD substrate solution contains 2 mg/ml OPD in the following diluent: 22.8 g $Na_2HPO_4(12H_2O)$, 1.0 g salicylic acid, 3.8 g citrate, 0.5 ml of 30% $H_2O_2$ per liter of distilled water, adjust pH to 6.0. The solution of OPD in this diluent is prepared just prior to use.

E. Isotyping

The monoclonal antibodies were isotyped using a mouse monoclonal isotyping kit from American Qualex. MML01, MML03 and MML05 were found to be of class IgG1.

F. Inhibition Assay

MML03 was further characterized by testing for inhibition of binding of MML03 antibody to $HbA_{1c}$ by various compounds. The compounds tested as potential inhibitors were: glucitol, mannitol, glucitol-VGG and mannitol-VGG. Glucitol was obtained from Merck, and mannitol was obtained from Junsei Chemical Co. Glucitol-VGG was prepared as described in Example 1 (glucose from Kokusan Chemical Works Ltd. was used as starting material), and mannitol-VGG was prepared as described in Example 16.

The inhibition assay was performed as described above for the ELISA screening assay, except that 10 µl of various concentrations of a potential inhibitor were added to the wells of the microtiter plate after the wells had been coated with the hemoglobin but before the addition of antibody. MML03 ascites fluid diluted 1:7000 with PBSA was used as the antibody. The results are presented in FIG. 16 for MML03 antibody.

Figure 16:
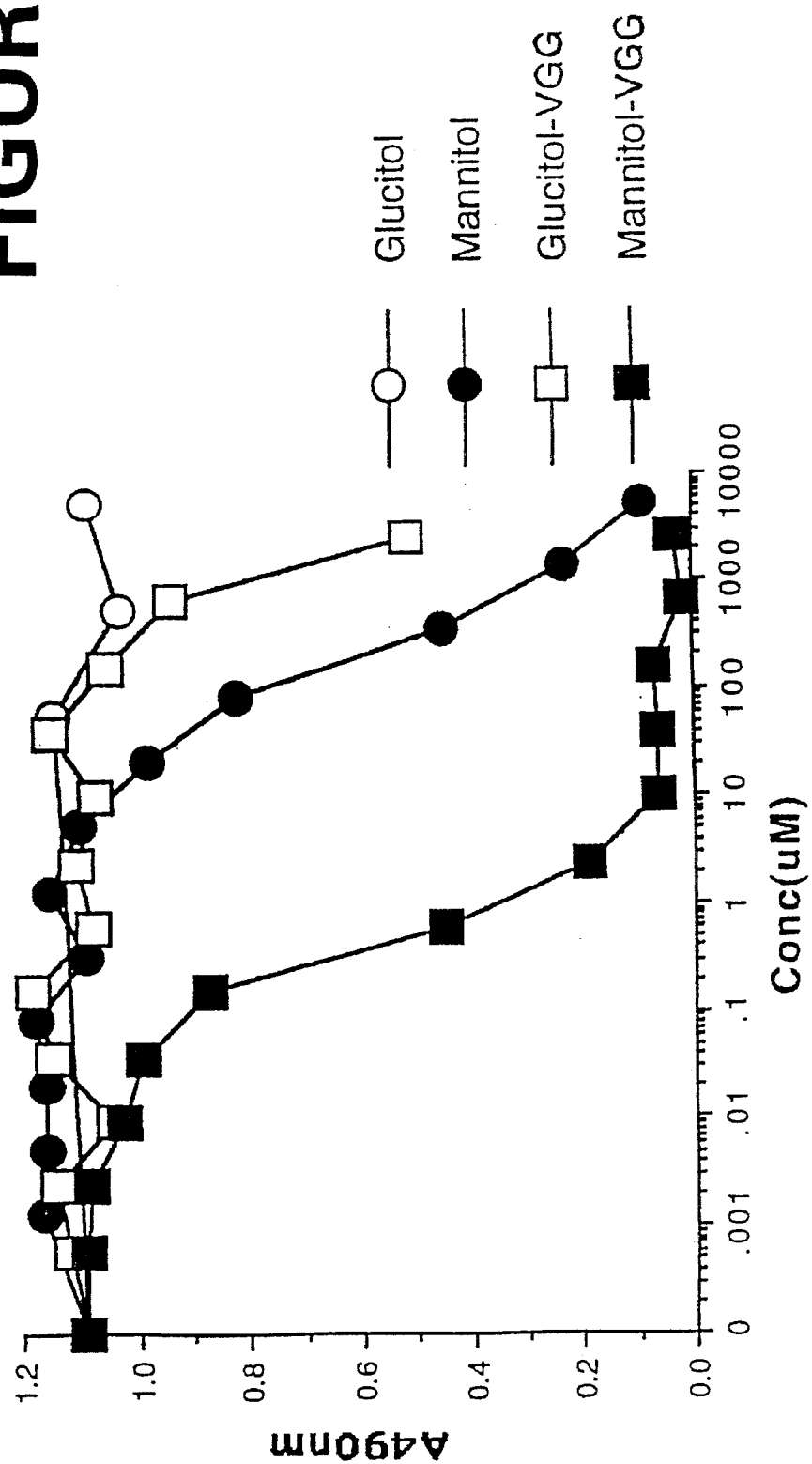
FIG. 16: A graph of absorbance at 490 nm versus concentration of inhibitor. Glucitol, mannitol, glucitol-VGG and mannitol-VGG were used as potential inhibitors of the reaction of monoclonal anti-mannitol-VGG-HSA antibody MML03 with reduced $HbA_{1c}$ in whole blood lysates.

In FIG. 16, the relative inhibitory capabilities of the various inhibitors can be determined by comparing the concentration of inhibitor required to reduce the absorbance at 490 nm to 0.5 absorbance units (about 50% inhibition). Using this criterion, mannitol-VGG is about 1000-fold better an inhibitor than mannitol and is about 4000-fold better an inhibitor than glucitol-VGG. Glucitol fails to inhibit the reaction at the concentrations examined. The results demonstrate that monoclonal antibody MML03 reacts preferentially with mannitol-VGG. The results also indicate that the structure recognized by MML03 on reduced $HbA_{1c}$ is mannitol-valine.

G. Standard HPLC Method

Ion exchange high pressure liquid chromatography (HPLC) is a standard method employed in many clinical laboratories for determining the concentration of $HbA_{1c}$ in patient samples. It was performed as described in Muruyama et al., *JJCLA*, 12 71–75 (1987) and Sugiura et al., *Medical Technology*, 18, 467–7 (1990).

Example 20

Direct Binding Immunoassay for $HbA_{1c}$ Employing Simultaneous Coating, Lysis and Reduction (CLR Format)

A direct binding immunoassay for $HbA_{1c}$ was performed in which $HbA_{1c}$ antigen sources were treated so that red blood cells (when present) were lysed, and the released hemoglobin $A_{1c}$ reduced and coated onto (adsorbed to) microtiter wells for subsequent detection in one step. Since coating, lysis and reduction occur simultaneously in this approach, we have designated this format the "CLR" format. The CLR assay was performed as follows.

First, 10 µl of $HbA_{1c}$ antigen source were added to 2.0 ml of 50 mM $NaBH_4$ (sample dilution factor of 1:200). After mixing, 80 µl of the mixture were transferred to 2.0 ml of 50 mM $NaBH_4$ and mixed (sample dilution factor 1:26, for a final sample dilution of 1:5200). While final sample dilutions can be varied from 1:100 to 1:5200, a final sample dilution of 1:5200 is preferred. Following mixing, 200 µl of the 1:5200 diluted sample were transferred to each well of Nunc F96Maxisorp Immunoplates (Nunc Inc., Naperville, Ill.), and the plates were shaken gently for 30 minutes at 37° C. to allow the antigen to adsorb to the wells. Unbound antigen was removed by aspiration, and the plates were washed 3 times with PBSA [0.01M sodium phosphate buffer containing 0.15M NaCl, 1% BSA, 0.1% Tween 20 (Sigma Chemical Co.), 0.02% $NaN_3$ (Sigma Chemical Co.), pH 7.3]. Washing was performed by filling the microtiter wells and subsequently aspirating the filled wells. The remaining polystyrene protein binding sites were blocked by allowing the third wash with PBSA to remain in the wells for 5 minutes at ambient temperature before aspirating it. After removing the final PBSA wash, 200 µl of anti-glucitol-VGG-BSA antibody (antiserum or DE-52 IgG fraction of antiserum prepared as described in Example 7) diluted in PBSA were added to the wells, and the plates were incubated for 30 minutes at 37° C. with shaking. The microtiter wells were next washed 3 times with PBS-Tween [0.01M sodium phosphate buffer containing 0.15M NaCl and 0.1% Tween 20], and 200 µl of alkaline phosphatase-conjugated, affinity-purified, $F(ab')_2$ fragments of goat anti-rabbit IgG (heavy and light chain specific; Organon Teknika Corp., Cappel Division, Durham, N.C.) diluted 1:7000 in PBSA were added to the wells, and the plates were incubated for 30 minutes at 37° C. with shaking. Then, the plates were washed with PBS-Tween 5 times, and 200 µl of substrate were added to the wells. Substrate consisted of 5 mg % of methyl-umbelliferyl phosphate (Sigma Chemical Co.) in 0.03M diethanolamine (Sigma Chemical Co.) containing 0.1 mM $MgCl_2 \cdot 6H_2O$, pH 9.8. Methylumbelliferone fluorescence was measured as relative fluorescence units (RFU) using a MicroFLUOR plate reader (Dynatech Instruments, Torrance, Calif.). The $HbA_{1c}$ antigen sources assayed were:

1) Whole blood clinical samples (containing disodium EDTA anticoagulant because of the use of the Becton Dickinson Vacutainer system (Baxter Diagnostics Scientific Products Division, McGaw Park, Ill.) to collect the blood.

2) Whole blood samples containing disodium EDTA anticoagulant which had been lyophilized and reconstituted to the original volume with distilled water. These whole blood samples were assayed independently for $HbA_{1c}$ by agarose electrophoresis using a commercially-available kit according to the manufacturer's (Ciba-Corning, Palo Alto, Calif., catalog no. 470055) instructions and were used as standards. The samples were found to contain 4.4%, 5.9%, 7.9% and 10.3% $HbA_{1c}$ by agarose electrophoresis.

3) BioRad Hemoglobin $A_{1c}$ Mini Column Test Calibrators (BioRad Clinical Division, Hercules, Calif.) which had been assayed by the manufacturer by HPLC and were reported by the manufacturer to contain 3.5%, 6.4% and 11.7% $HbA_{1c}$. These Calibrators were also used as standards.

The controls were identical to those described in Example 10.

The percentage $HbA_{1c}$ in the clinical samples could be determined directly by comparison of the RFU response for these samples with the RFU response obtained with the standards of known percentage $HbA_{1c}$ (either the BioRad Hemoglobin $A_{1c}$ Calibrators or the lyophilized whole blood samples assayed by agarose electrophoresis). The percentage of $HbA_{1c}$ in the clinical samples was determined by linear regression analysis of the standard curves in which the response (RFU) of the standards was taken as the dependent variable and the percentage $HbA_{1c}$ of each standard was the independent variable. At least three standards of different percentage $HbA_{1c}$ were employed in duplicate for generating each standard curve.

Figure 17:
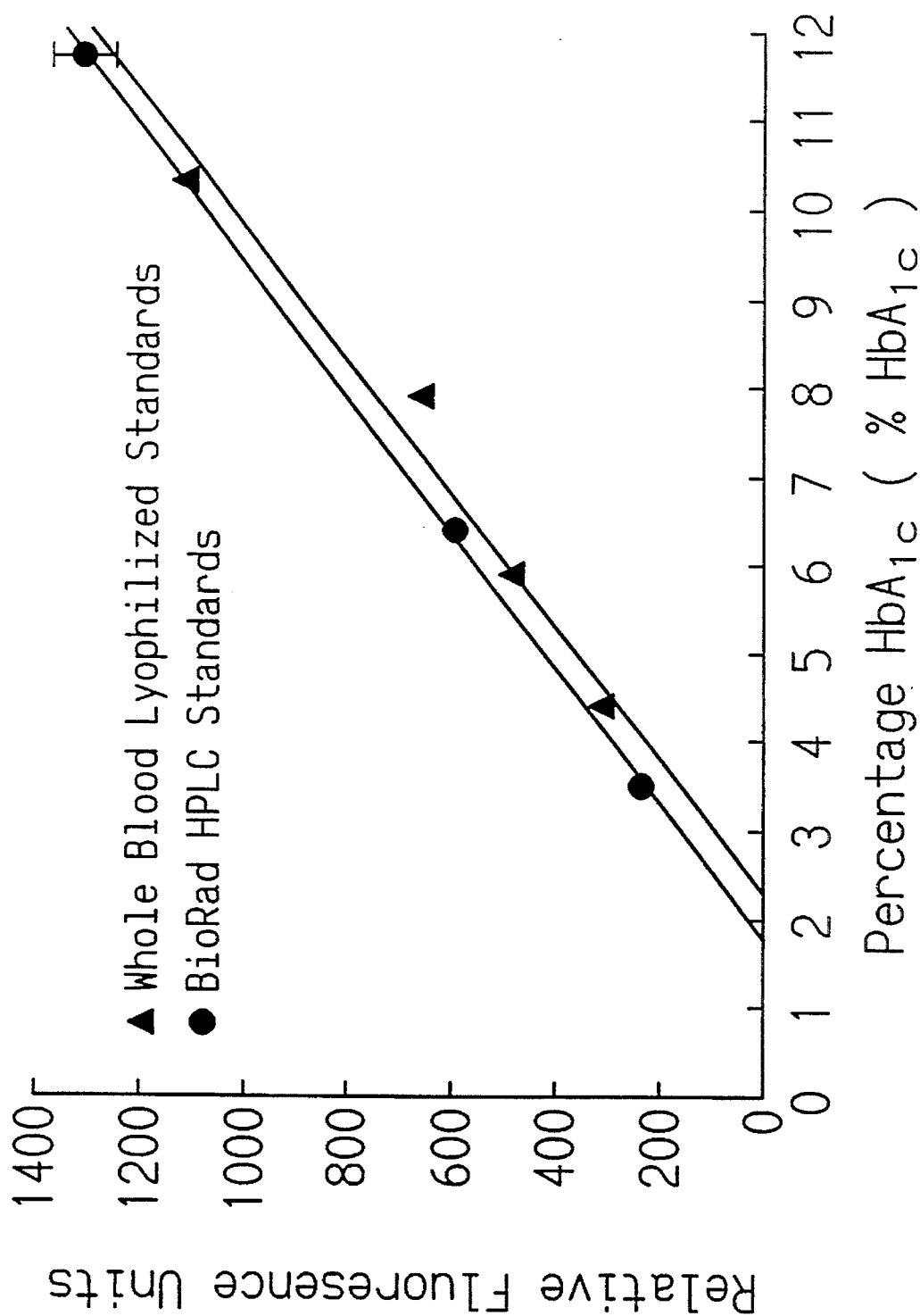
FIG. 17: Graph showing representative standard curves for direct binding immunoassay for $HbA_{1c}$ in the CLR format using polyclonal anti-glucitol-VGG-BSA antiserum, DE-52 IgG fraction. In the CLR format, red blood cells, when present in samples, are lysed, and the released hemoglobin is reduced and coated onto the wells of microtiter plates all in one step (i.e., lysis, reduction and coating occur simultaneously). The standards were BioRad Hemoglobin $A_{1c}$ Mini Column Test Calibrators (BioRad HPLC Standards) or lyophilized and reconstituted whole blood samples.
Figure 18:
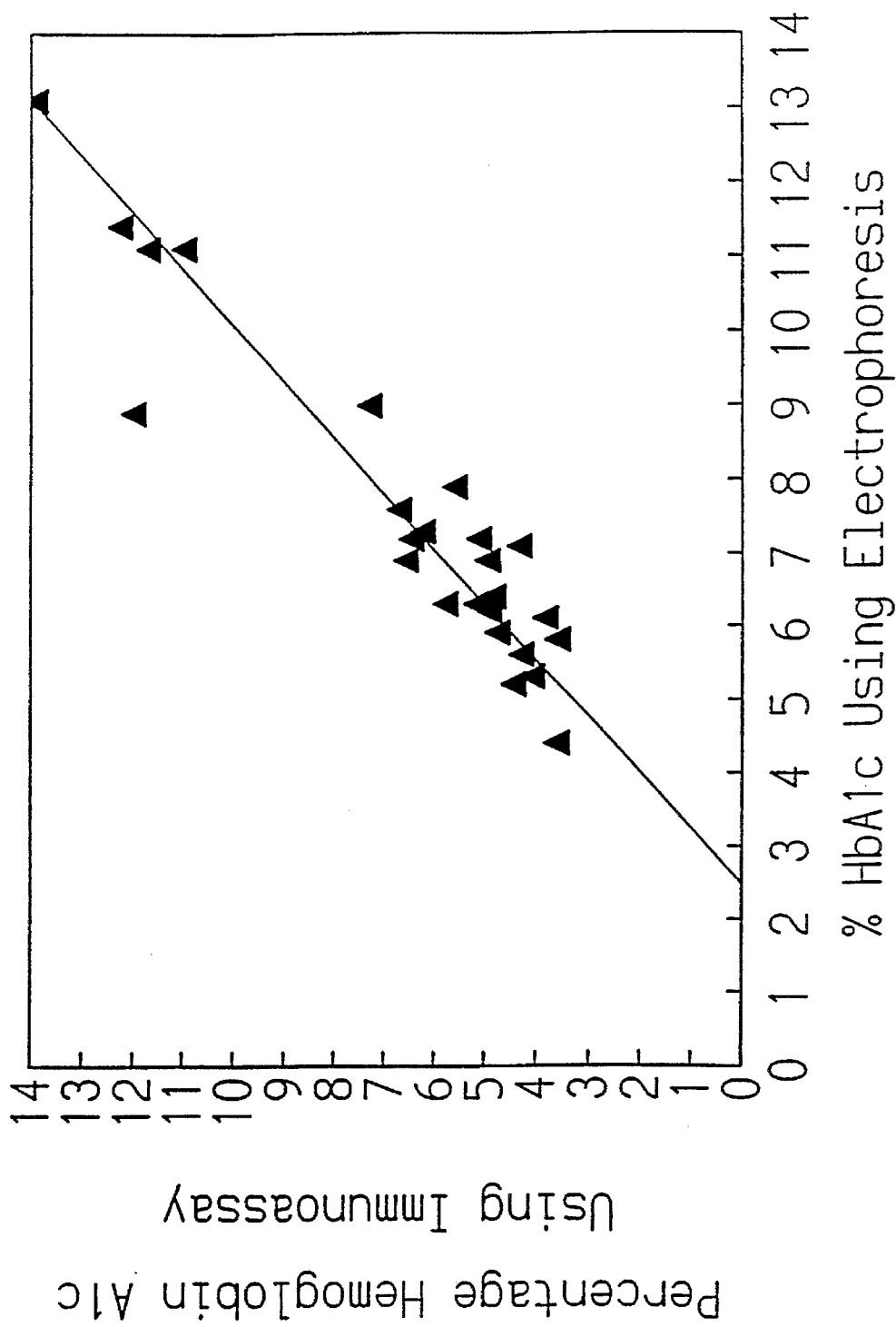
FIG. 18: Graph of percentage $HbA_{1c}$ measured by agarose electrophoresis versus percentage $HbA_{1c}$ measured by a direct binding immunoassay using polyclonal anti-glucitol-VGG-BSA antiserum, DE-52 IgG fraction, in the CLR format. BioRad Hemoglobin $A_{1c}$ Mini Column Test Calibrators were used as standards.
Figure 19:
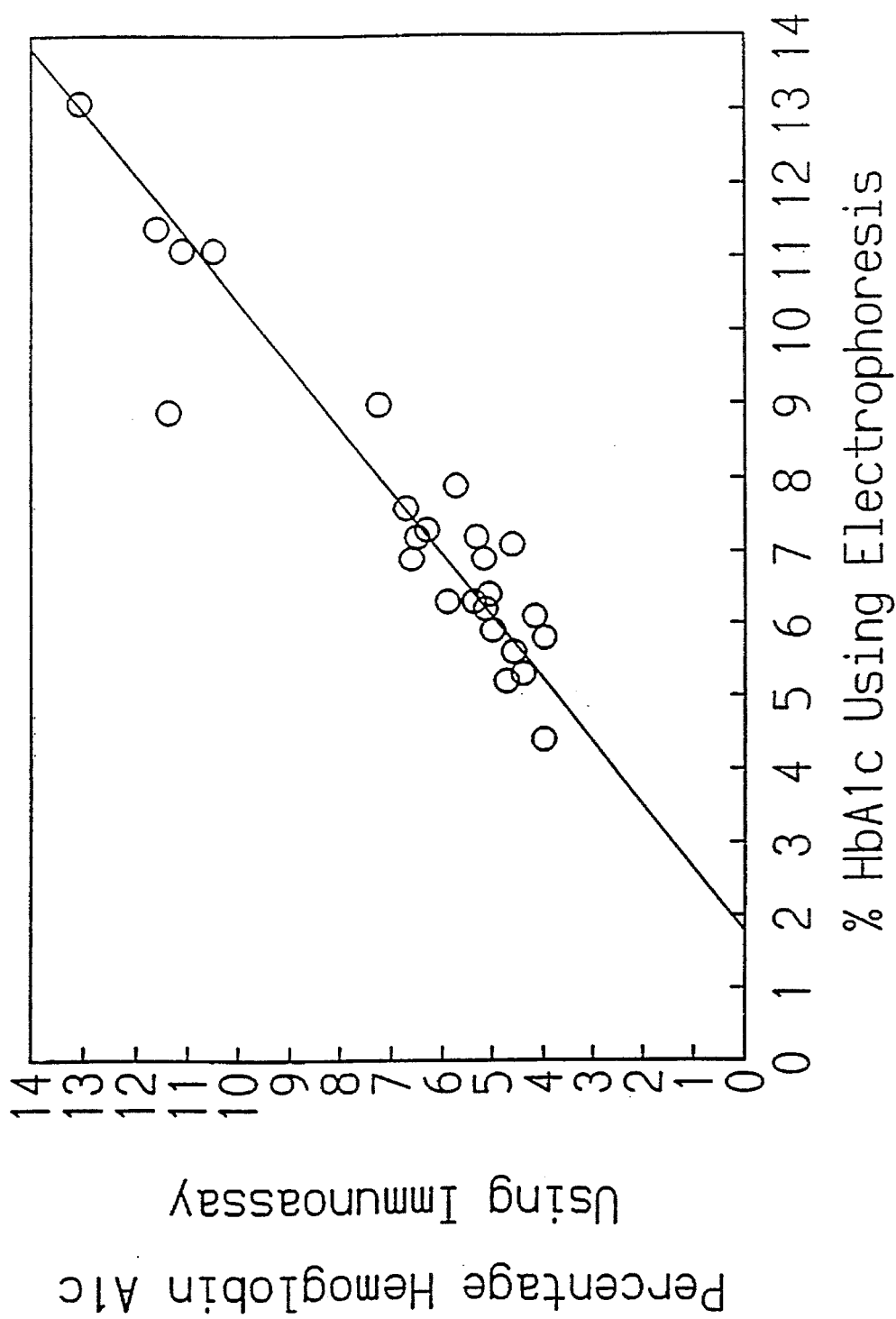
FIG. 19: Graph of percentage $HbA_{1c}$ measured by agarose electrophoresis versus percentage $HbA_{1c}$ measured by a direct binding immunoassay using polyclonal anti-glucitol-VGG-BSA antiserum, DE-52 IgG fraction, in the CLR format. Lyophilized and reconsituted whole blood samples were used as standards.

The results obtained using the polyclonal anti-glucitol-VGG-BSA antiserum DE-52 IgG fraction are presented in FIGS. 17–19. All points represent the average of duplicate measurements. Error bars (as standard deviation) are included, but the error bars are visible only when they are larger than the graphic symbol.

FIG. 17 shows representative standard curves for the BioRad Hemoglobin $A_{1c}$ Calibrators and for the lyophilized, reconstituted whole blood samples. Lines represent least squares "best fit" lines obtained by linear regression of the response (RFU) obtained for standards of different percentage $HbA_{1c}$. The linear least squares regression equation describing either standard curve is $$\% \ HbA_{1c} = (\text{mean relative fluoresence units} - b)/a,$$

where a is the slope of the line, and b is the y-intercept. Regression parameters obtained for the curve using BioRad Hemoglobin $A_{1c}$ Calibrators as standards were a=131, b=−234, correlation coefficent, r=0.9997, and x-intercept of 1.78. Regression parameters obtained for the standard curve using the lyophilized, reconstituted whole blood samples as standards were a=133 and b=−306, with a correlation coefficent, r=0.9846 and an x-intercept of 2.30. As can be seen from FIG. 17, similar standard curves were obtained with the lyophilized whole blood samples and the BioRad Hemoglobin $A_{1c}$ Calibrators. The standard curves have nearly identical slopes, and both demonstrate a lower limit of detection of about 2% $HbA_{1c}$ based on the extrapolated x-intercept values obtained.

FIG. 18 shows a comparison of the percentage $HbA_{1c}$ values measured by agarose electrophoresis with those measured by the CLR direct binding immunoassay for the 25 whole blood clinical samples. The BioRad Hemoglobin $A_{1c}$ Calibrators were used as standards. The percentage $HbA_{1c}$ measured by agarose electrophoresis demonstrates good correlation with the percentage $HbA_{1c}$ obtained by the CLR immunoassay (correlation coefficent, r=0.9380).

FIG. 19 shows a comparison of percentage $HbA_{1c}$ values measured by agarose electrophoresis with those obtained by the CLR direct binding immunoassay for the 25 clinical whole blood samples. The lyophilized whole blood samples were used as standards. The percentage $HbA_{1c}$ measured by agarose electrophoresis demonstrates good correlation with the percentage $HbA_{1c}$ obtained with the CLR assay (correlation coefficient, r=0.94).

Example 21

Direct Binding Immunoassay for $HbA_{1c}$ In The CLR Format Using Monoclonal Anti-Mannitol-VGG-HSA A direct binding immunoassay in the CLR format using monoclonal anti-mannitol-VGG-HSA antibody was performed in a manner similar to that described in Example 20. First, 20 μl of $HbA_{1c}$ antigen source were added to 2.0 ml of 50 mM NaBH4 (final sample dilution factor of 1:100). Following mixing, 100 μl of the diluted sample containing $HbA_{1c}$ were transferred to each well of Nunc F96Maxisorp Immunoplates, and the plates were shaken gently for 45 minutes at ambient temperature to allow the antigen to adsorb to the wells. Unbound antigen was removed by aspiration, and the plates were washed 3 times with PBSA. The remaining polystyrene protein binding sites were blocked by allowing the third Cash with PBSA to remain in the wells for 5 minutes at ambient temperature before aspirating the final PBSA wash. After removing the final PBSA wash, 100 μl of monoclonal anti-mannitol-VGG-HSA antibody MML03 (Protein-G purified fraction of mouse ascites; prepared as described in Example 19) diluted in PBSA were added to the wells, and the plates were incubated for 60 minutes at room temperature. The microtiter wells were next washed 3 times with PBS-Tween, and 100 μl of horseradish peroxidase-conjugated rabbit anti-mouse immunoglobulin (Dako A/S, Glostrup, Denmark) diluted 1:1500 in PBSA were added to the wells. The plates were incubated for 40 minutes at room temperature, after which time the plates were washed with PBS-Tween 5 times. Then, substrate was added to the wells (100 μl/well), and the plates were allowed to incubate at room temperature until ample colorimetric signal was obtained (generally for a period of 15 to 30 minutes). The substrate consisted of 0.03% $H_2O_2$ and 2 mg/ml of o-phenylenediamine dihydrochloride (Sigma Chemical Co.) in 0.05M citrate-0.1M phosphate buffer, pH 5.0. The reaction was terminated by the addition of 200 μl of 2N $H_2SO_4$, and the absorbance at 490 nm was measured using a V max kinetics microplate reader (Molecular Devices, Menlo Park, Calif.). The controls and the $HbA_{1c}$ antigen sources used were the same as those described in Example 20, except that only 12 clinical whole blood samples were assayed.

The percentage $HbA_{1c}$ could be determined directly by comparison of the absorbance at 490 nm obtained for a given sample with that obtained for the standards. The percentage of $HbA_{1c}$ in the clinical samples was determined by linear regression analysis of the standard curves in which the response (absorbance at 490 nm) of the standards was taken as the dependent variable and the percentage $HbA_{1c}$ of each standard was the independent variable. At least three standards of different percentage $HbA_{1c}$ values were employed in duplicate for generating each standard curve.

Figure 20:
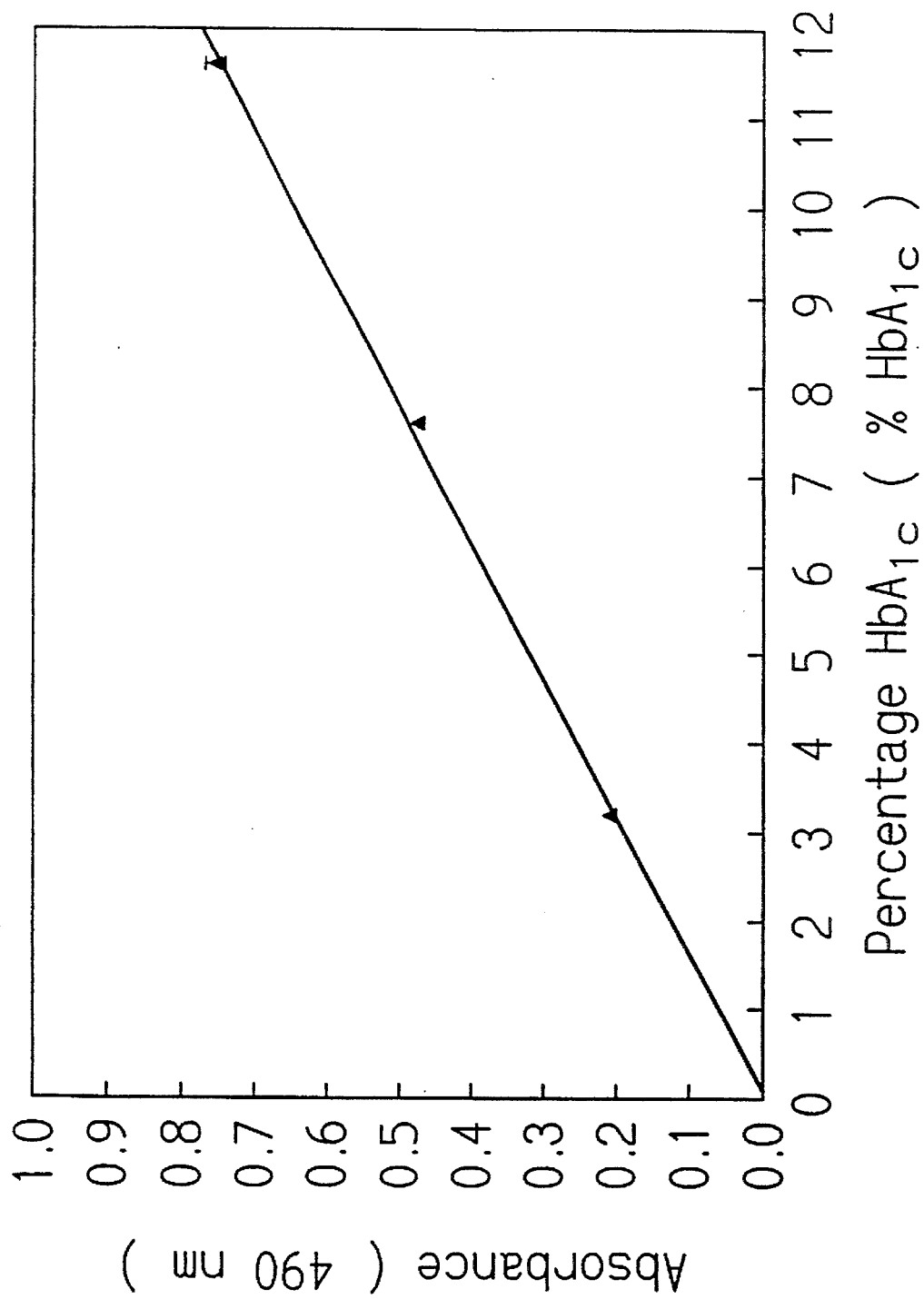
FIG. 20: Graph showing a representative standard curve obtained using monoclonal anti-mannitol-VGG-HSA antibody MML03 (Protein G-purified fraction of ascites) in a direct binding $HbA_{1c}$ immunoassay in the CLR format. BioRad Hemoglobin $A_{1c}$ Mini Column Test Calibrators were used as standards.
Figure 21:
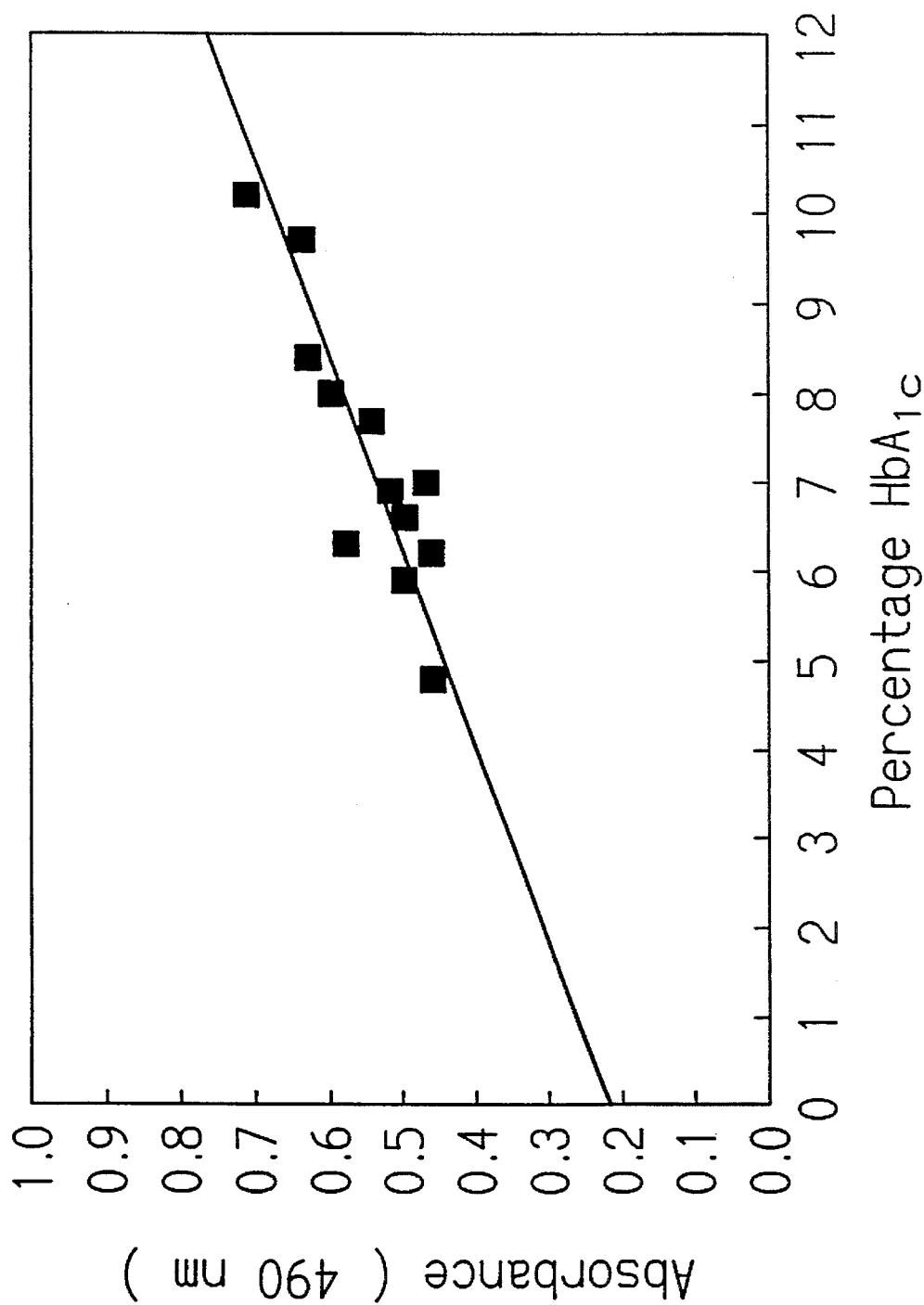
FIG. 21: Graph of absorbance at 490 nm for 12 whole blood clinical samples obtained in a direct binding immunoassay for $HbA_{1c}$ in the CLR format using monoclonal anti-mannitol-VGG-HSA antibody MML03 (Protein G-purified fraction of ascites) versus percentage $HbA_{1c}$ measured by a standard HPLC method for the same 12 samples.

The results are shown in FIGS. 20 and 21. All points represent the average of duplicate measurements. Error bars (as standard deviation) are included, but the error bars are visible only when they are larger than the graphic symbol.

FIG. 20 shows a typical standard curve obtained using the BioRad Hemoglobin $A_{1c}$ Mini Column Test Calibrators as standards. The linear least squares regression equation describing the standard curve is $$\% \ HbA_{1c} = (\text{mean absorbance at 490 nm} - b)/a,$$

where a is the slope of the line, and b is the y-intercept. Regression parameters obtained for the curve using the BioRad Hemoglobin $A_{1c}$ Calibrators as standards were a=0.065, b=−0.006, a correlation coefficent, r=0.9986, and an x-intercept of 0.0897.

FIG. 21 shows the absorbance at 490 nm obtained for the 12 clinical whole blood samples in the direct binding CLR immunoassay graphed against the percentage $HbA_{1c}$ of the clinical samples measured by a standard HPLC method (see section G, Example 19). The percentage $HbA_{1c}$ values obtained using the direct binding CLR immunoassay compares favorably with the values obtained using HPLC (correlation coefficient r=0.8736).

Example 22

Direct Binding Immunoassay for $HbA_{1c}$ Employing Simultaneous Lysis and Reduction, With Subsequent Coating (The LR-C Format), Using Labeled Secondary Antibody A direct binding immunoassay for $HbA_{1c}$ was performed in which the $HbA_{1c}$ antigen source was treated so that red blood cells (when present) were lysed, and the released hemoglobin $A_{1c}$ was reduced in one step. Then, the reduced hemoglobin $A_{1c}$ was further diluted in a buffer to promote adsorption (coating) of the reduced protein to microtiter wells for subsequent detection and allowed to adsorb to the wells. Since lysis and reduction in this format occur simultaneously, and antigen coating occurs in a subsequent separate step, we have designated this format the "LR-C" format. The LR-C format was performed as follows.

First, 10 μl of $HbA_{1c}$ antigen source were added to 90 μl of 50 mM $NaBH_4$ (sample dilution factor of 1:10) with mixing, and sample lysis and reduction were allowed to occur by incubating the mixture at ambient temperature for 20 minutes. After the incubation, 900 μl coating buffer (0.1M NaHCO₃, pH 9.8), were added to the lysed, reduced sample (additional dilution of 1:10; total sample dilution of 1:100), and (when desired) a further dilution of 1:500 was made by transferring 20 μl of this sample into a tube containing 980 μl of coating buffer (final dilution of 1:5000). Final sample dilutions in the LRC format could be varied from 1:100 to 1:5000, but a final sample dilution of 1:5000 is preferred when polyclonal primary antibody is employed. Equally good results are obtained when monoclonal primary antibody is reacted with either 1:100 diluted samples or 1:5000 diluted samples (see below). Following mixing, 100 μl of the diluted sample were transferred to the wells of Nunc F96 Maxisorp Immunoplates. The plates were incubated for 30 minutes at ambient temperature to allow adsorption (coating) of the reduced hemoglobin antigen to the microtiter wells. Unbound antigen was removed by aspiration, and the plates were washed 3 times with PBSA lacking NaN₃. The remaining polystyrene protein binding sites were then blocked by allowing the third wash with PBSA to remain in the wells for 5 minutes at ambient temperature before aspirating the final PBSA wash. After removing the final PBSA wash, 100 μl of primary antibody [mouse monoclonal anti-mannitol-VGG-HSA antibody MML03 (Protein G-purified fraction of ascites; prepared as described in Example 19), polyclonal anti-glucitol-VGG-BSA antibody (DE-52 IgG fraction; prepared as described in Example 7), or polyclonal anti-mannitol-VGG-BSA antibody (DE-52 IgG fraction; prepared as described in Example 18)] diluted in PBSA lacking NaN₃ were added. Incubation with primary antibody was for 30 minutes at room temperature. Then, the antibody was removed from the wells by aspiration, and the wells were washed 3 times with PBS-Tween. Enzyme-labeled secondary antibody was added (100 μl/well), and the plates were incubated for 30 minutes at room temperature. When mouse monoclonal antibody was used as the primary antibody, the secondary antibody was horseradish peroxidase labeled F(ab')₂ fragment of rabbit anti-mouse IgG (Southern Biotechnology Associates, Birmingham, Ala., catalog #6120–05) diluted 1:1000 in PBSA lacking NaN₃. When rabbit polyclonal antibody was employed as the primary antibody, the secondary antibody was horseradish peroxidase labeled F(ab')'₂ fragment of goat anti-rabbit IgG (Cappel division of Organon Teknika Corporation, Westchester, Pa., catalog #3312–0081) diluted 1:15,000 in PBSA lacking NAN₃. After the incubation with secondary antibody, the wells were aspirated and washed 5 times with PBS-Tween. Substrate (0.03% $H_2O_2$ and 2 mg/ml of o-phenylenediamine dihydrochloride in 0.0M citrate-0.1M phosphate buffer, pH 5.0) was added to the wells (100 μl/well) and allowed to incubate at room temperature until ample colorimetric signal was obtained (generally for a period of 15 to 30 minutes). The reaction was terminated by the addition of 200 μl of 2N $H_2SO_4$, and the absorbance at 492 nm was measured using a Titertek Multiscan Plus MKII coloimetric microtiter plate reader. The controls and the $HbA_{1c}$ antigen sources were those described in Example 20, except that 37 whole blood clinical samples were used.

Representative results are shown in FIGS. 22–27. All points represent the average of duplicate measurements. Error bars are included (as standard deviation), but they are visible only when they are larger than the graphic symbol.

Figure 22:
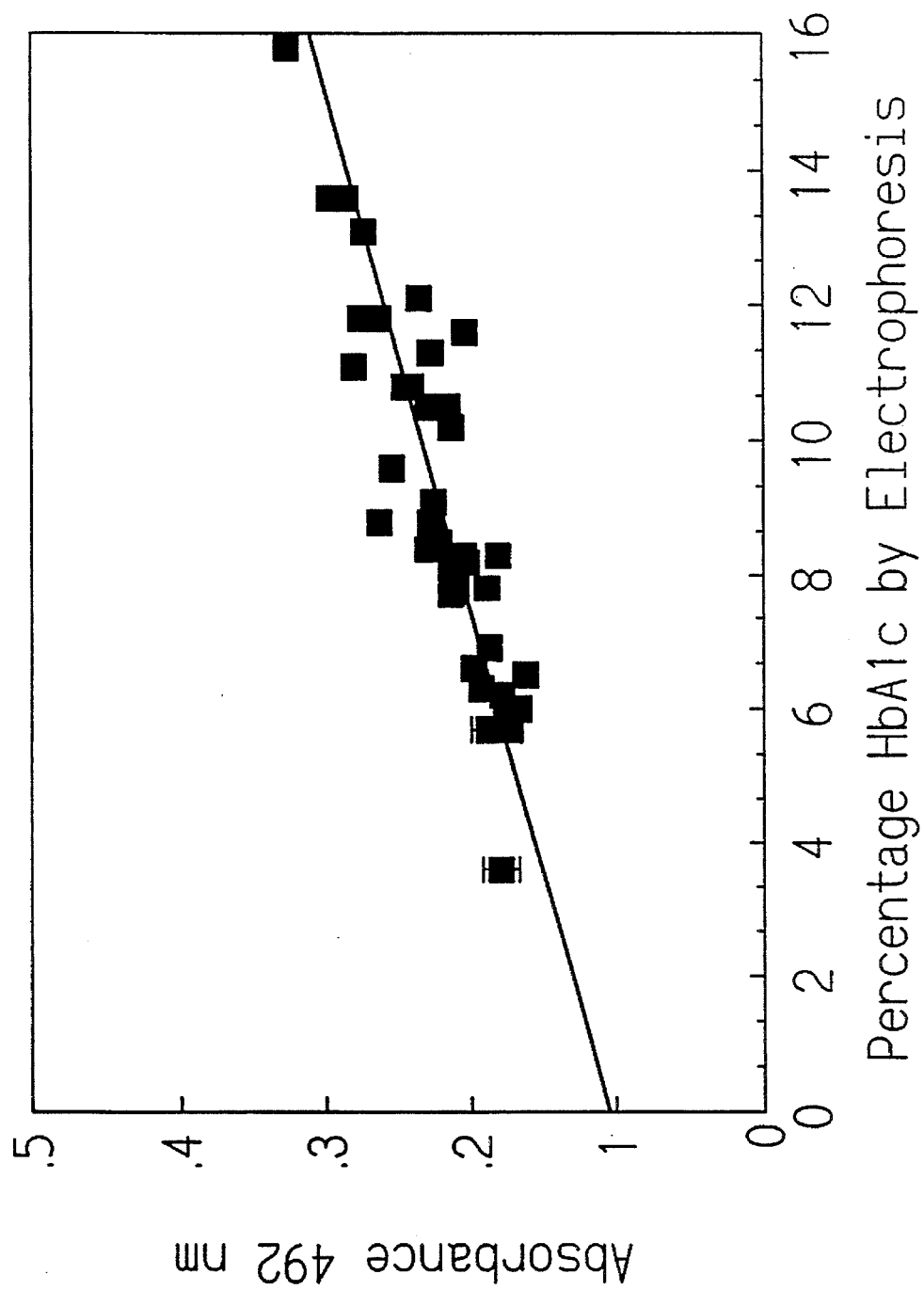
FIG. 22: Graph of the absorbance at 492 nm for 37 whole blood clinical samples measured in a direct binding immunoassay for $HbA_{1c}$ in the LR-C format using polyclonal anti-glucitol-VGG-BSA antibody (DE-52 IgG fraction) versus percentage $HbA_{1c}$ measured by agarose electrophoresis for the same 37 samples. In the LR-C format, red blood cells, when present in samples, are lysed, and the released hemoglobin is reduced in one step. Subsequently, the reduced hemoglobin is coated onto the wells of microtiter plates.

FIG. 22 shows absorbance at 492 nm obtained in the direct binding immunoassay LR-C format for the 37 whole blood clinical samples using polyclonal anti-glucitol-VGG-BSA antibody (DE-52 IgG fraction) graphed versus percentage $HbA_{1c}$ measured by agarose electrophoresis. Good correlation between absorbance at 492 nm (LR-C immunoassay) and percentage $HbA_{1c}$ (agarose electrophoresis) was obtained (correlation coefficient, r=0.8736).

Figure 23:
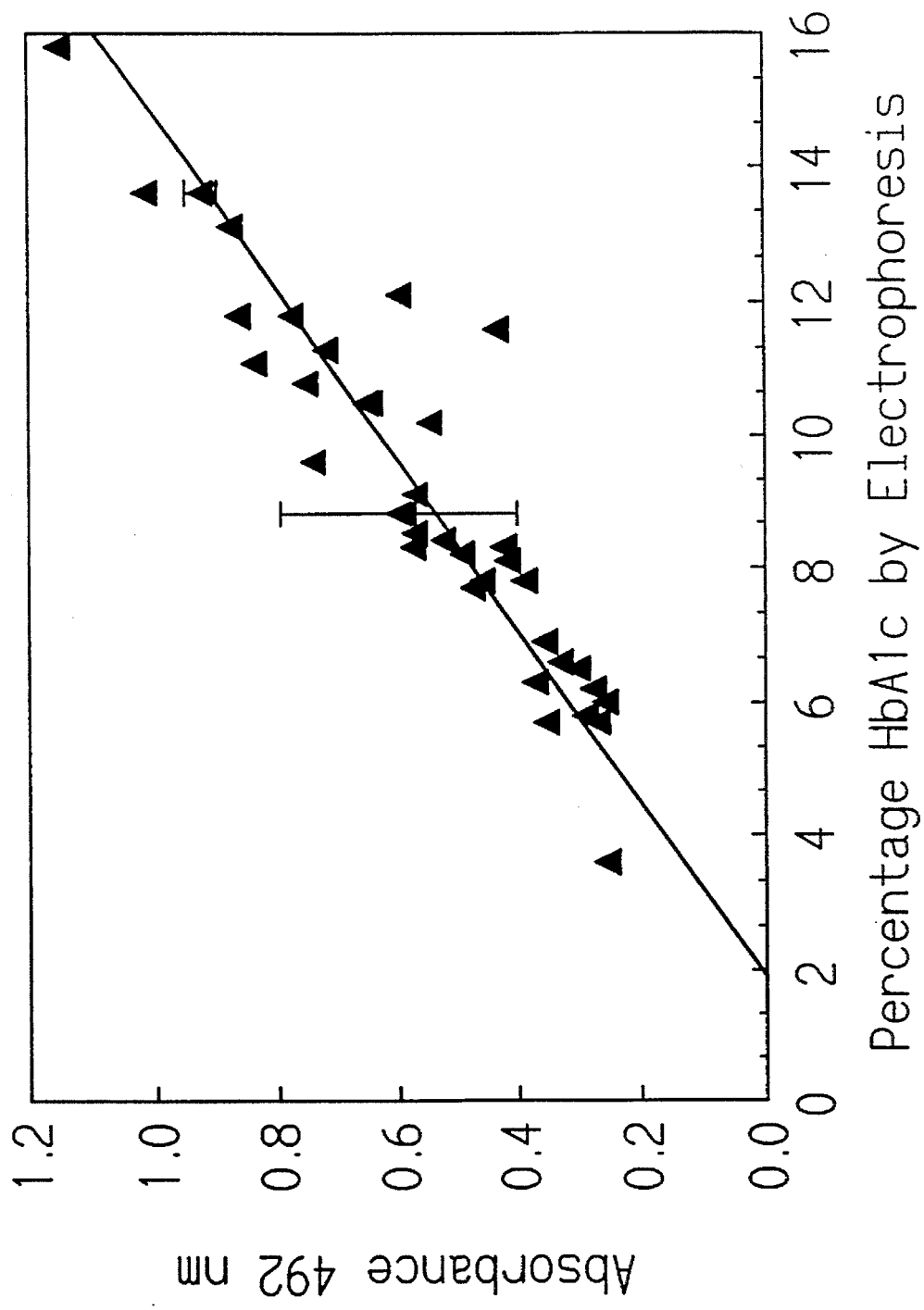
FIG. 23: Graph of the absorbance at 492 nm for 37 whole blood clinical samples measured in a direct binding immunoassay for $HbA_{1c}$ in the LR-C format using polyclonal anti-mannitol-VGG-BSA antibody (DE-52 IgG fraction) versus percentage $HbA_{1c}$ measured by agarose electrophoresis for the same 37 samples.

FIG. 23 shows absorbance at 492 nm in the direct binding immunoassay LR-C format for the 37 whole blood clinical samples using polyclonal anti-mannitol-VGG-BSA antibody (DE-52 IgG fraction) graphed versus percentage $HbA_{1c}$ measured by agarose electrophoresis. Good correlation between absorbance at 492 nm (LR-C immunoassay) and percentage $HbA_{1c}$ (agarose electrophoresis) was obtained (correlation coefficient, r=0.9227).

Figure 24:
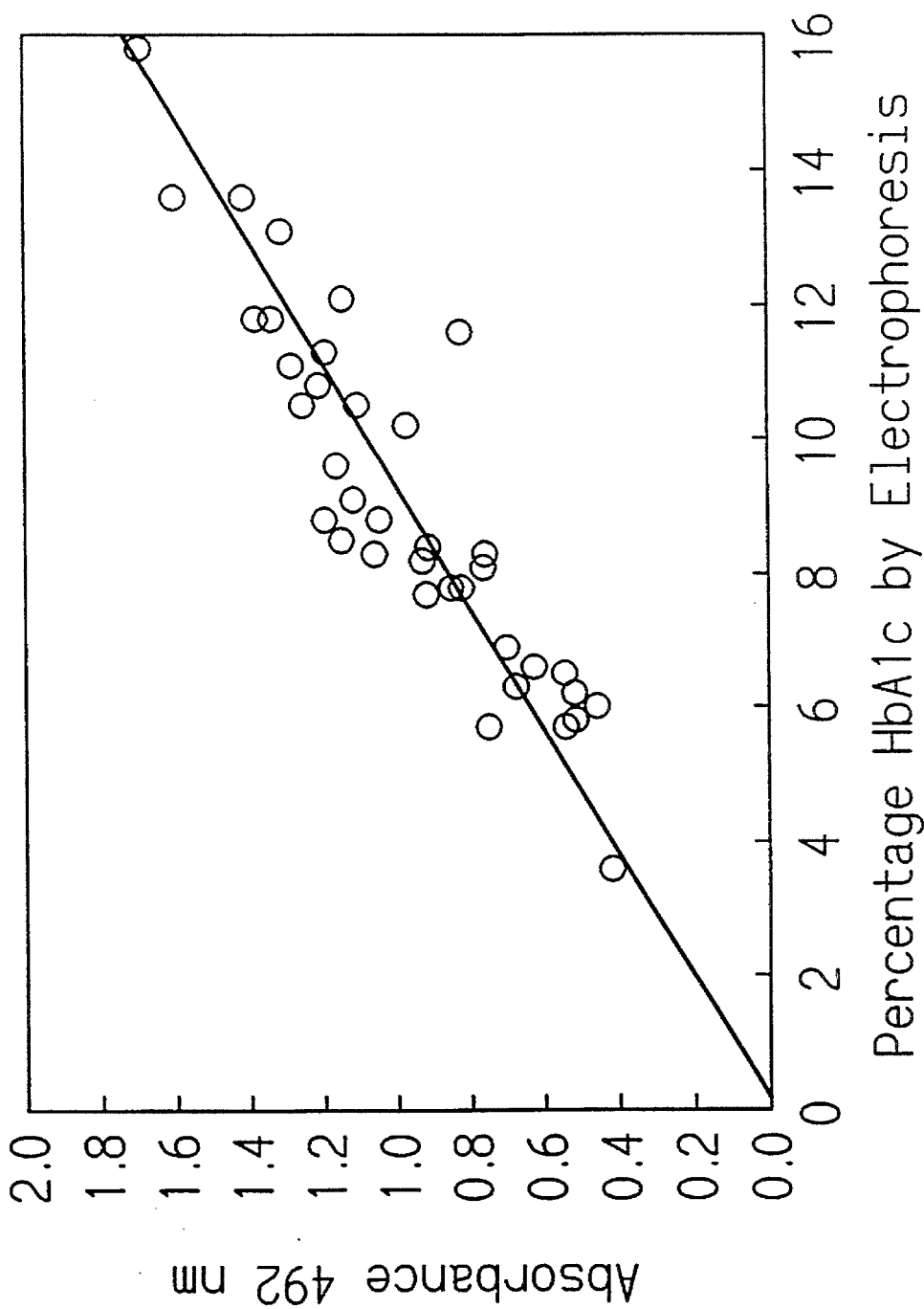
FIG. 24: Graph of the absorbance at 492 nm for 37 whole blood clinical samples measured in a direct binding immunoassay for $HbA_{1c}$ in the LR-C format using monoclonal anti-mannitol-VGG-BSA antibody MML03 (Protein G-purified fraction of ascites) versus percentage $HbA_{1c}$ measured by agarose electrophoresis for the same 37 samples.

FIG. 24 shows absorbance at 492 nm in the direct binding immunoassay LR-C format for the 37 whole blood clinical samples using monoclonal anti-mannitol-VGG-HSA antibody (Protein G-purified fraction of ascites) graphed versus percentage $HbA_{1c}$ measured by agarose electrophoresis. Good correlation between absorbance at 492 nm (LR-C immunoassay) and percentage $HbA_{1c}$ (agarose electrophoresis) was obtained (correlation coefficient, r=0.9112).

A comparison of FIG. 22 with FIG. 23 reveals that mannitol-VGG-BSA immunogen (FIG. 23) produces antibody responsiveness superior to that obtained using glucitol-VGG-BSA immunogen (FIG. 22). Also, when the results obtained with polyclonal antibodies (FIGS. 22 and 23) are compared with those obtained using monoclonal antibody (FIG. 24), it can be seen that the monoclonal antibody is superior. These results taken together indicate that the mannitol-VGG-BSA and mannitol-VGG-HSA immunogens produce antibodies with superior $HbA_{1c}$ reactivities as compare to antibody produced by immunizing with glucitol-VGG-BSA.

Figure 25:
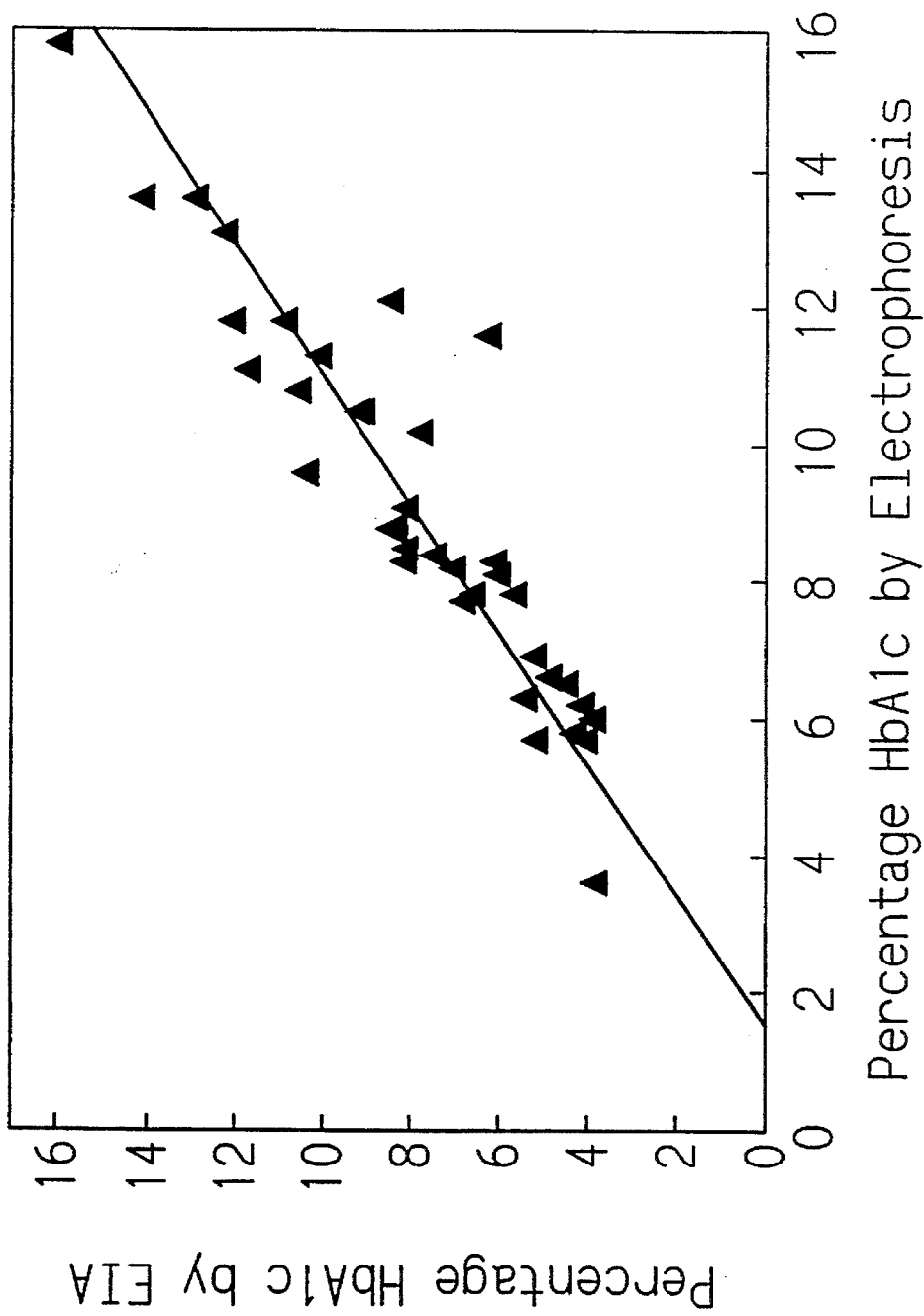
FIG. 25: Graph of percentage $HbA_{1c}$ measured by agarose electrophoresis versus percentage $HbA_{1c}$ obtained with a direct binding immunoassay in the LR-C format using polyclonal anti-glucitol-VGG-BSA antiserum (DE-52 IgG fraction) for 37 whole blood samples.
Figure 26:
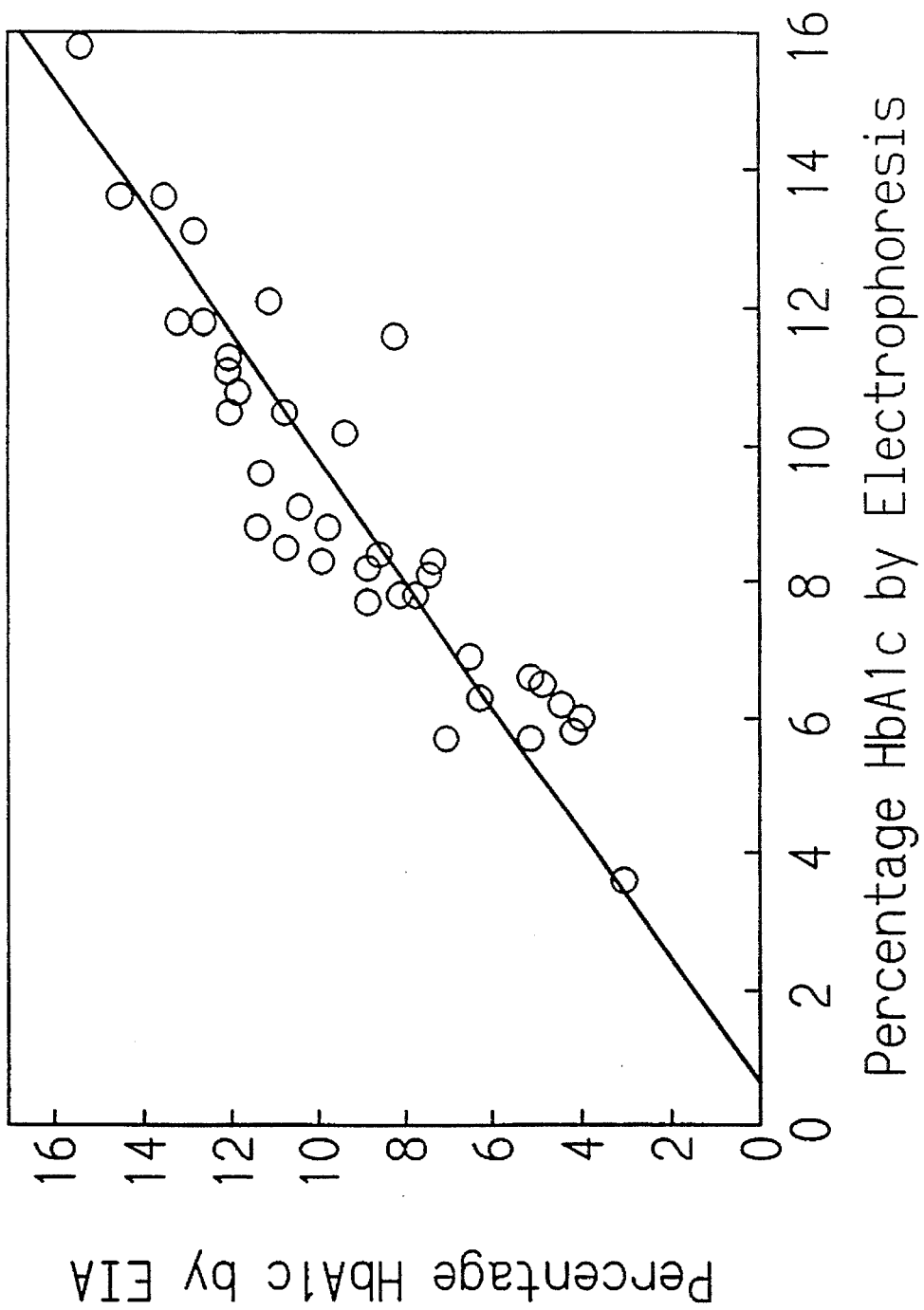
FIG. 26: Graph of percentage $HbA_{1c}$ measured by agarose electrophoresis versus percentage $HbA_{1c}$ obtained with a direct binding immunoassay in the LR-C format using polyclonal anti-mannitol-VGG-HSA antibody MML03 (DE-52 IgG fraction) for 37 whole blood samples.
Figure 27:
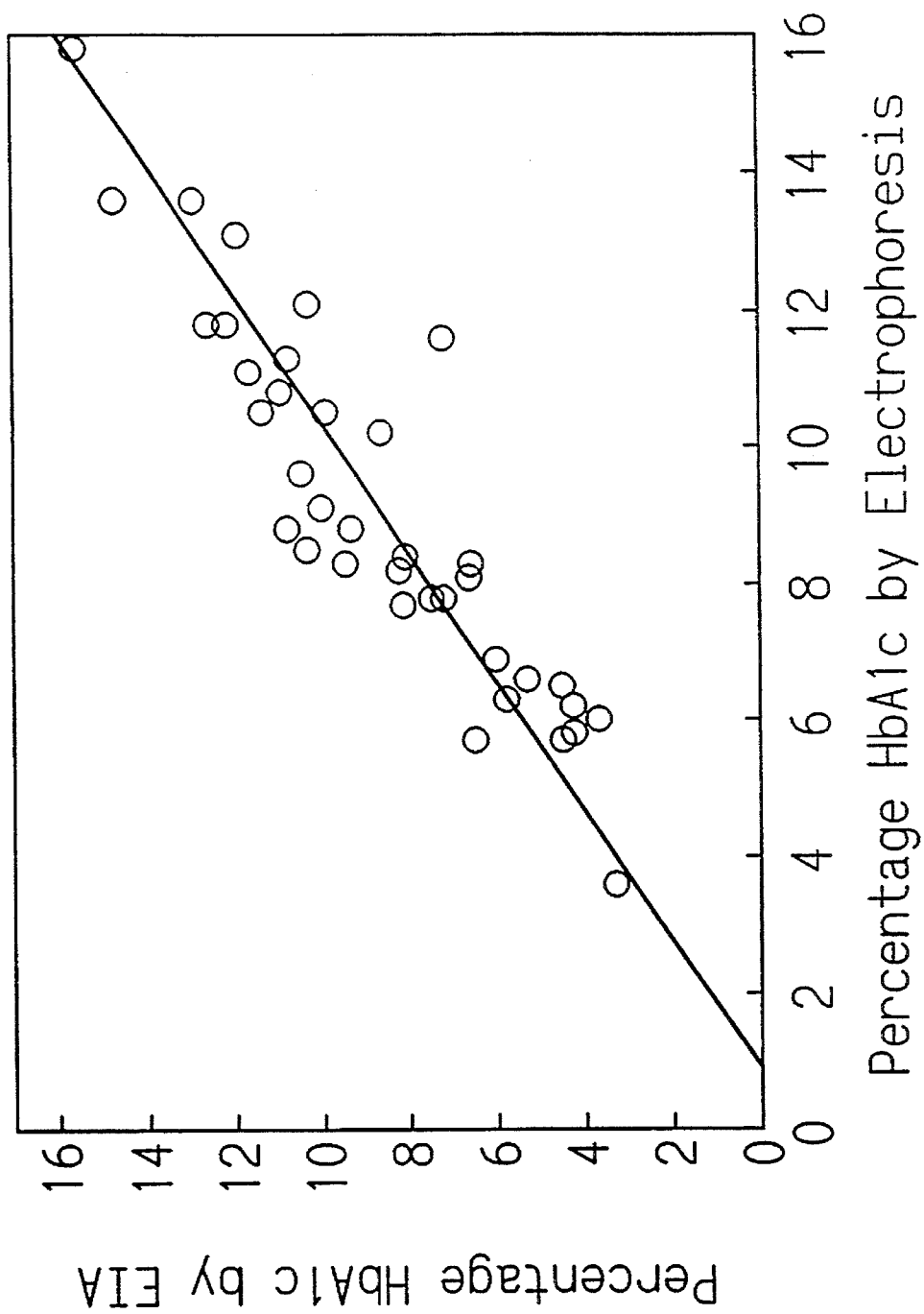
FIG. 27: Graph of percentage $HbA_{1c}$ measured by agarose electrophoresis versus percentage $HbA_{1c}$ obtained with a direct binding immunoassay in the LR-C format using monoclonal anti-mannitol-VGG-HSA antibody MML03 (Protein G-purified fraction of ascites) for 37 whole blood samples.
Figure 28:
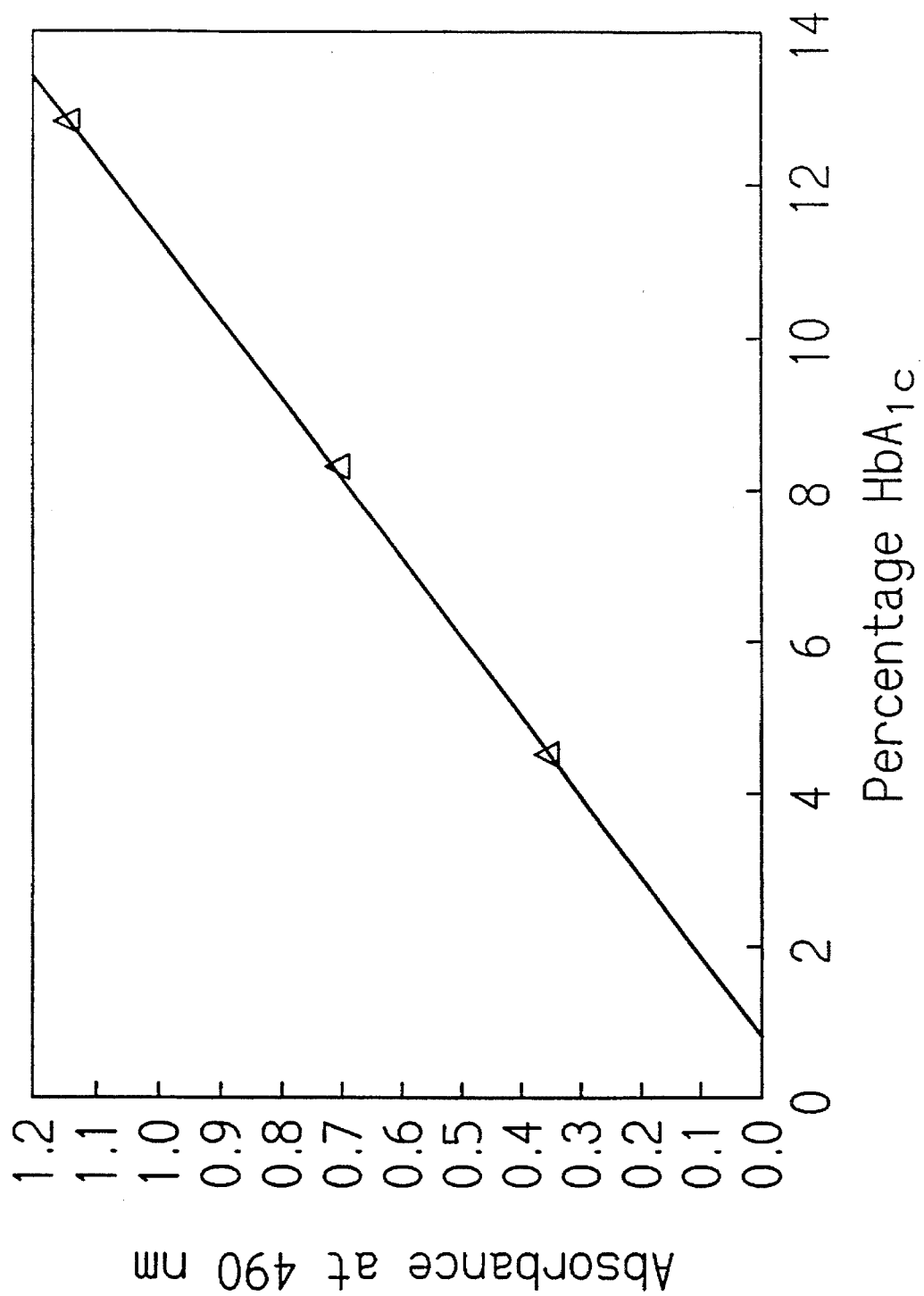
FIG. 28: Graph showing a representative standard curve obtained using lyophilized and reconstituted whole blood samples as standards in a direct binding immunoassay in the LR-C format using enzyme-labeled monoclonal anti-mannitol-VGG-HSA antibody MML03.

Comparisons of the results obtained by measuring percentage $HbA_{1c}$ by the direct binding immunoassay LR-C format with the percentage $HbA_{1c}$ values obtained using agarose electrophoresis are presented in FIGS. 25–27. All points represent the average of duplicate measurements. Error bars are included (as standard deviation), but they are visible only when they are larger than the graphic symbol. The percentage $HbA_{1c}$ values obtained using the LR-C format immunoassay with either monoclonal or polyclonal antibody corresponded well with the percentage $HbA_{1c}$ values obtained independently for the same samples by agarose electrophoresis (correlation coefficients, r=0.9227, 0.9169 and 0.9112 for FIGS. 25, 26, and 27, respectively). The use of monoclonal anti-mannitol-VGG-HSA antibody in the LR-C format possessed the added advantage that sample dilutions of only 1:100 needed to be used.

Example 23

Direct Binding Immunoassay For $HbA_{1c}$ Employing The LR-C Format And Enzyme-Labeled Primary Antibody A direct binding immunoassay for $HbA_{1c}$ was performed in the LR-C format using enzyme-labeled monoclonal anti-mannitol-VGG-HSA antibody Fab' fragments. To perform the assay, 10 μl of whole blood were added to 90 μl of 50 mM NaBH₄ and incubated for 20 minutes at room temperature. The reduced sample was diluted 1:500 with coating buffer. Coating buffer contains 21.01 g citric acid monohydrate and 1 ml KathonCG (Rohm & Haas) per liter, with the pH adjusted to 4.2 with 1N NaOH. Kathon CG contains 1.15% 5 -chloro-2-methyl-4-isothiazoline-3-one, 0.35% 2-methyl-4-isothiazoline-3-one, 23% magnesium salt and 75.5% water.

One hundred microliters per well of the diluted hemolysate were added to the wells of 96-well Nunc Immunoplates.

The plates were incubated for 30 minutes at room temperature, after which the wells were washed 2 times with washing buffer (PBS containing 0.5 ml Tween 20, 50 mg p-methoxyphenol and 1 ml KathonCG per liter PBS, pH adjusted to 8.0).

Then, 100 μl of peroxidase-labeled MML03 antibody Fab' (preparation described below) diluted with conjugate diluent (PBS containing 1% BSA and 1 ml/liter KathonCG) were added, and the plates were incubated for 30 minutes at room temperature. After 5 washes with washing buffer, 100 μl of OPD substrate solution (prepared as described in Example 19) were added per well, and the plates were incubated for 30 minutes at room temperature. Finally, 200 μl of 2N $H_2SO_4$ was added, and the absorbance at 490 nm was measured on a Dynatech MR700 microplate reader. Peroxidase-labelled MML03 Fab' were prepared by a modification of the method described in Ishikawa et al., *J. Immunoassay*, 4, 209–327 (1983). Briefly, IgG was precipitated from MML03 ascites fluid (prepared as described in Example 19) by slowly adding saturated $(NH_4)_2SO_4$ to the ascites fluid until a final concentration of 50% saturation was reached and then stirring at 4° C. for 4 hours. The mixture was centrifuged at 3000 rpm for 10 minutes, and the precipitate (IgG) was dissolved in PBS and this solution dialzyed against PBS. Then, 30 mg of the IgG was dialyzed against 0.1M $CH_3COONa$, 0.1M NaCl, pH 4.2, at 4° C. Pepsin (0.2 mg per 10 mg IgG) was dissolved in the dialyzed IgG, and the mixture was incubated for 15–18 hours at 37° C. The pH of the digested IgG solution was adjusted to 7.0 using 1N NaOH, and the digested IgG solution was applied to an Ultrogel AcA44 column (2×45 cm; IBF-Biotechnics) and was eluted using 0.1M sodium phosphate buffer, pH 7.0. Three-milliliter fractions were collected, and the first peak showing absorbance at 280 nm contained $F(ab')_2$ fragments. The fractions comprising this peak were pooled and concentrated. To prepare Fab' from the $F(ab')_2$, 1/9 volume of 0.1M aminoethanethiol hydrochloride (Tokyo Kasei Kogyo) in 0.1M sodium phosphate buffer, pH 6.0, containing 5 mM EDTA, was added to the pooled, concentrated $F(ab')_2$ fractions, and the mixture was incubated for 1.5 hours at 37° C. The reaction mixture was then applied to a Sephadex G-25 column (1×45 cm) (Pharmacia Biotech Inc.), and THE Fab' eluted with 0.1M sodium phosphate buffer, pH 6.0. Fractions demonstrating absorption at 280 nm were pooled and concentrated. Maleimide groups were added to the peroxidase enzyme using EMCS (epsilon-maleimido caproic acid; Dojindo Laboratories) as follows. First, 15 mg of peroxidase (Toyobo) was dissolved in 0.45 ml of 0.1M sodium phosphate buffer, pH 7.0. Next, 1.8 mg of EMCS was dissolved in 0.1 ml of N,N-dimethylformamide (Wako Pure Chemical Industries, Ltd.), and 50 μl of this solution were added to the peroxidase solution. The mixture was incubated at 30° C. for 30 minutes and then applied to a Sephadex G-25 column (1×45 cm) and eluted with 0.1M sodium phosphate buffer, pH 6.0. Fractions which turned brown in color were pooled and concentrated. An equimolar (100 μM) amount of the pooled, concentrated maleimide-derivatized peroxidase was added to the Fab' fragments, and this mixture was incubated for 15–20 hours at 4° C. to conjugate the peroxidase to the Fab' fragments. The reaction mixture was subsequently loaded onto an Ultrogel AcA44 column (2×45 cm), and the conjugate was eluted using 0.1M sodium phosphate buffer, pH 8.5. The fractions of the first main peak of absorbance at 280 and 402 nm contained the peroxidase-labeled Fab'.

The $HbA_{1c}$ content of the red blood cell lysates from patients (normal and diabetic) was assayed by the above procedure, by standard HPLC methods (see section G, Example 19), and by the Tina-quant method. The Tina-quant method was performed according to the manufacturer's (Boehringer Mannheim) instructions. Tina-quant is a turbidimetric immunoassay which utilizes a polyhapten and antibody to $HbA_{1c}$. The polyhapten consists of a dextran carrier with several N-terminus glycosylated peptides of hemoglobin beta-chain (an $HbA_{1c}$-specific epitope). In the absence of $HbA_{1c}$, the antibody reacts with and aggregates the polyhapten, and the turbidity is measured at 340 nm. If $HbA_{1c}$ is present in a patient sample, aggregation is inhibited in proportion to the amount of $HbA_{1c}$ present in the sample. The standards used were the lyophilized, reconstituted whole blood samples described in Example 20.

The results are presented in FIGS. 28–31. All points represent duplicate measurements. Error bars (standard deviation) are included, but are visible only when they are larger than the graphic symbols.

A typical standard curve for the direct binding LR-C immunoassay described above is shown in FIG. 28. The linear least squares regression equation describing the standard curve is $$\% \ HbA_{1c} = (\text{mean absorbance at 490 nm} - b)/a,$$

where a is the slope of the line, and b is the y-intercept. Regression parameters obtained for the curve were a=0.095, b=−0.076, correlation coefficent, r=0.9999, and an x-intercept of 0.7966. Thus, over the range of percentage $HbA_{1c}$ tested (4.5% to 12.8%), the standard curve demonstrates good correlation between absorbance at 490 nm and percentage $HbA_{1c}$.

Figure 29:
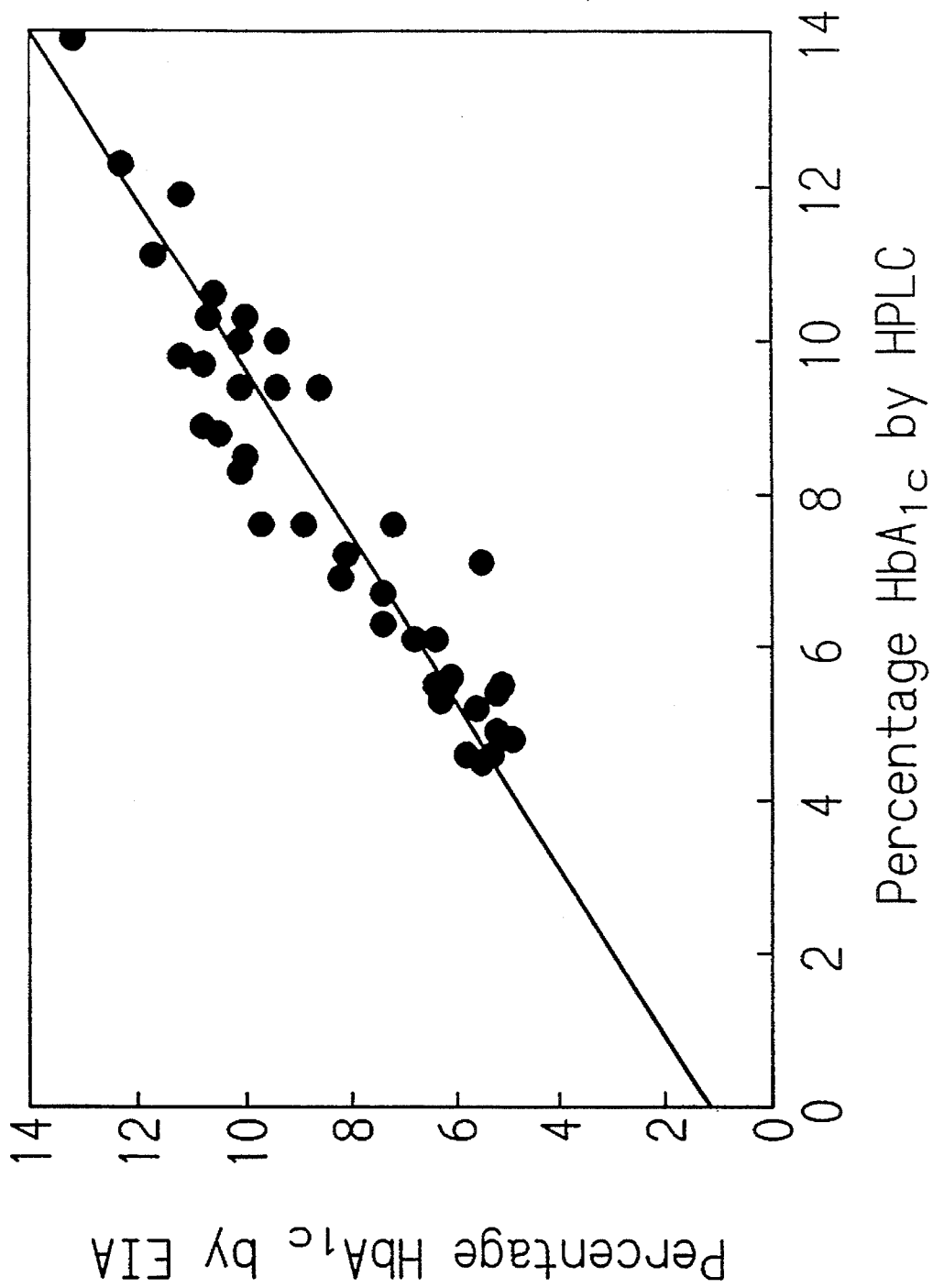
FIG. 29: Graph of percentage $HbA_{1c}$ for 40 whole blood clinical samples measured by HPLC versus percentage $HbA_{1c}$ for these same samples obtained by direct binding immunoassay in the LR-C format using enzyme-labeled monoclonal anti-mannitol-VGG-HSA antibody MML03.

FIG. 29 shows a comparison of percentage $HbA_{1c}$ measured by HPLC with percentage $HbA_{1c}$ obtained with the direct binding LR-C immunoassay described above for 40 whole blood clinical samples. The percentage $HbA_{1c}$ of the 40 patient samples measured by the direct binding immunoassay of the present invention correlated in a statistically significant manner with the percentage $HbA_{1c}$ of those same samples measured by the standard HPLC method (coefficient of correlation, r= 0.9407).

Figure 30:
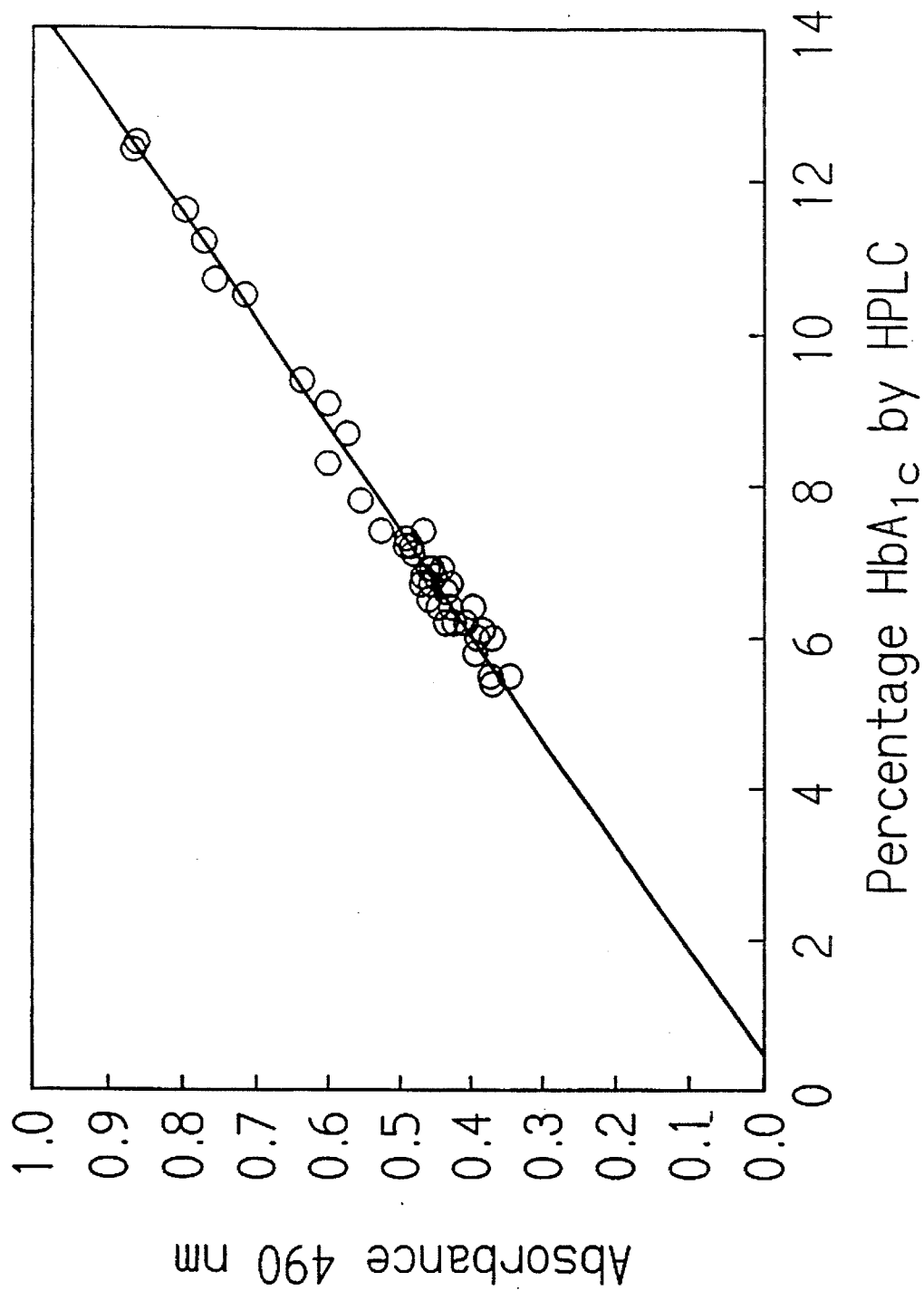
FIG. 30: Graph of absorbance at 490 nm for 42 whole blood clinical samples as measured in a direct binding immunoassay for $HbA_{1c}$ in the LR-C format using enzyme-labeled monoclonal anti-mannitol-VGG-HSA antibody MML03 versus percentage $HbA_{1c}$ of these same samples measured by HPLC.

FIG. 30 is a graph of absorbance at 490 nm obtained in the direct binding LR-C immunoassay described above for 42 whole blood clinical samples versus percentage $HbA_{1c}$ measured in those samples by HPLC. Good correlation between absorbance at 490 nm (direct binding immunoassay) and percentage $HbA_{1c}$ (HPLC) was obtained (correlation coefficent, r=0.9923).

Figure 31:
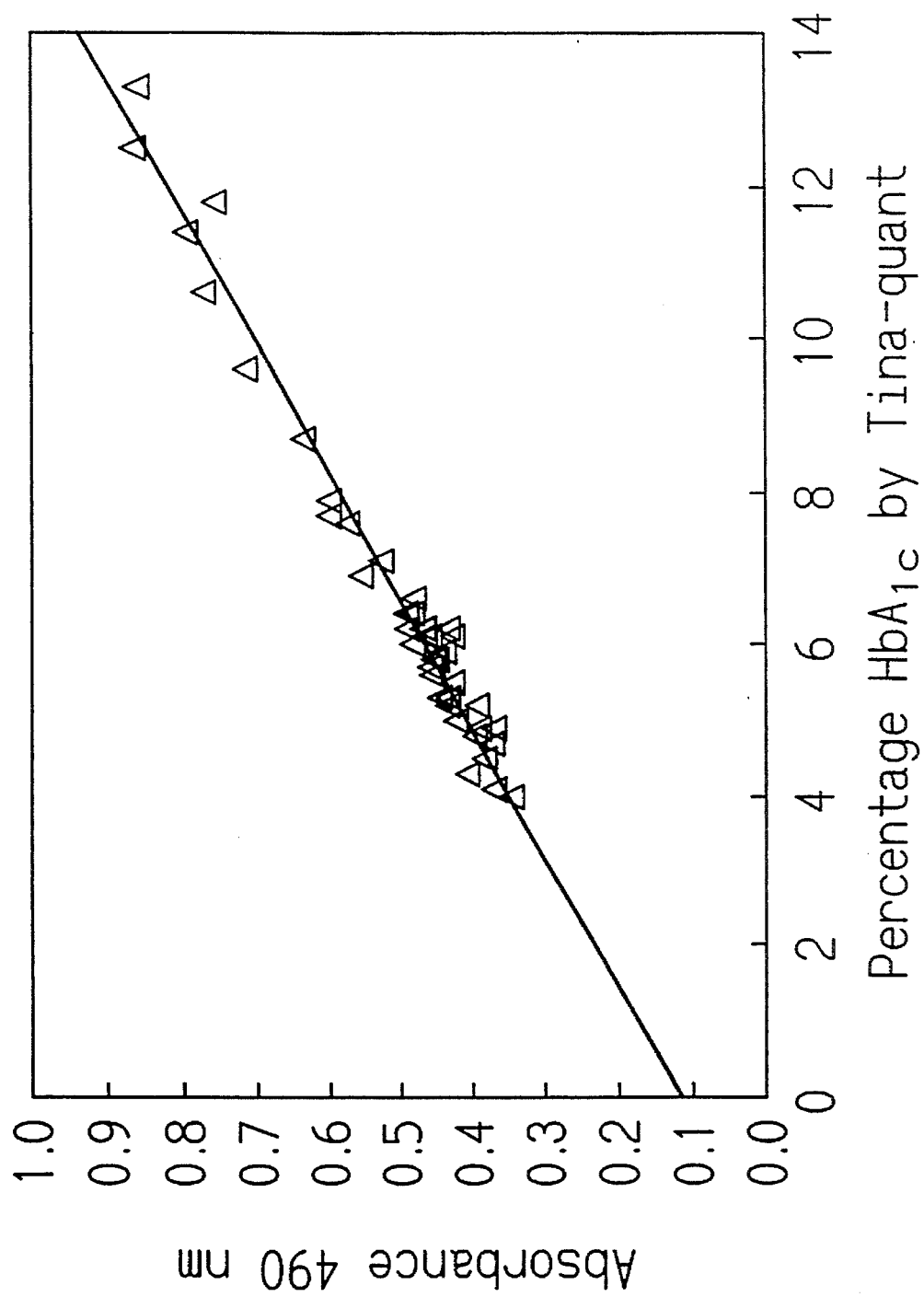
FIG. 31: Graph of absorbance at 490 nm for 42 whole blood clinical samples as measured in a direct binding immunoassay for $HbA_{1c}$ in the LR-C format using enzyme-labeled monoclonal anti-mannitol-VGG-HSA antibody MML03 versus percentage $HbA_{1c}$ for these same samples measured by the Tina-quant $HbA_{1c}$ immunoassay.

FIG. 31 is a graph of absorbance at 490 nm obtained in the direct binding LR-C immunoassay described above for 42 whole blood clinical samples versus percentage $HbA_{1c}$ measured in the same samples by the Tina-quant method. Good correlation between absorbance at 490 nm (direct binding immunoassay) and percentage $HbA_{1c}$ (Tina-quant) was obtained (correlation coefficent, r=0.9862).

Example 24

Effect of Carbamylation on the Measurement of $HbA_{1c}$

In addition to glycosylation, the amino groups of proteins can be modified in other ways. In particular, in uremic patients, the amino groups of proteins (including the alpha amino group of the N-terminal amino acid) may be carbamylated. Accordingly, an experiment was performed to determine if carbamylation interferes with the detection of $HbA_{1c}$.

Hemoglobin was carbamylated by a modification of the method described in Engbaek et al., *Clin. Chem.*, 35, 93–97 (1989). Briefly, 1.5 ml of blood (EDTA anticoagulated) was mixed with 15 ml of isotonic saline. The red blood cells (RBC) were collected as a pellet by centrifugation at 3000 rpm at 4° C. for 10 min. The supernatant was aspirated, and the RBC were resuspended in 15 ml of isotonic saline. The RBC were pelleted again by centrifugation at 3000 rpm at 4° C. for 10 min. The supernatant was aspirated, and the RBC were resuspended in 7.5 ml of suspension buffer (5.14 mmol $Na_2HPO_4$ $2H_2O$, 1.53 mmol $KH_2PO_4$, and 145 mmol of NaCl, pH 7.2). One-milliliter aliquots of the cell suspension were pipetted into six tubes. Sodium cyanate (NaOCN; Wako Pure Chemical Industries, Ltd.) was prepared at concentrations of 0, 20, 40, 60, 80 and 100 mM, and 50 μl of each concentration was pipetted into one of the six tubes containing RBC. The tubes were incubated at 37° C. for 2 hours to allow for the carbamylation of the hemoglobin. The final concentration of NaOCN in the reaction tubes was 0, 1, 2, 3, 4, and 5 mM. The carbamylation reaction was terminated by the addition of 1 ml of isotonic saline to each tube, centrifuging at 3000 rpm for 10 min. at 4° C. to pellet the RBC and aspirating the supernatant. The RBC were resuspended in 1 ml isotonic saline and stored at 4° C. prior to use.

The carbamylated RBC were assayed in the direct binding immunoassay described in Example 23 with the RBC suspensions being lysed and diluted to a final dilution of 1:100 to determine the percentage $HbA_{1c}$. The percentage $HbA_{1c}$ was also determined by a standard HPLC method (see section G, Example 19).

Figure 32:
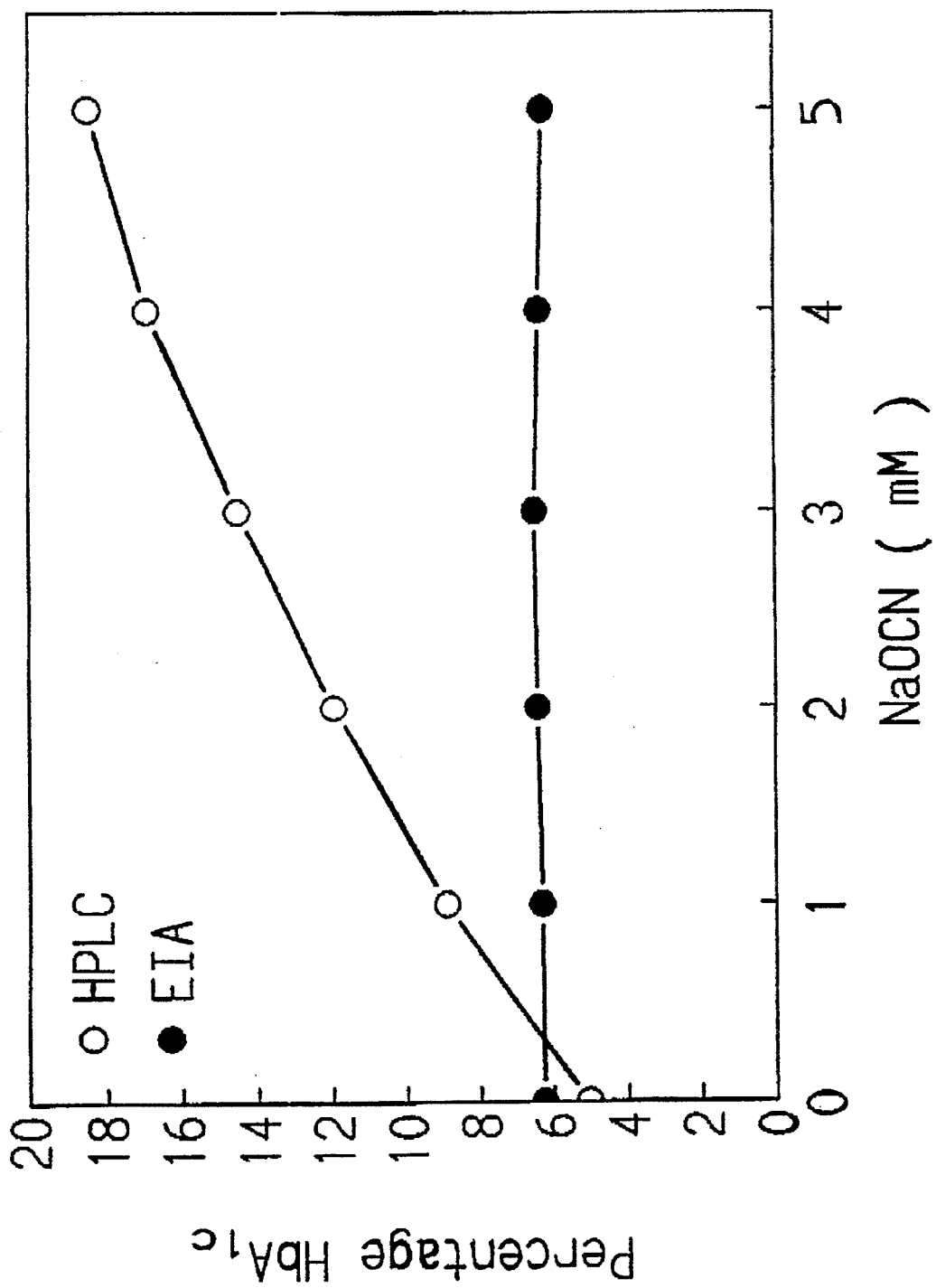
FIG. 32: Graph of percentage $HbA_{1c}$ versus concentration of sodium cyanate used to carbamylate hemoglobin. The percentage of $HbA_{1c}$ was determined by HPLC and by a direct binding immunoassay for $HbA_{1c}$ in the LR-C format using enzyme-labeled monoclonal anti-mannitol-VGG-HSA antibody MML03.

The results are shown in FIG. 32 which is a graph of percentage $HbA_{1c}$ determined by the direct binding immunoassay and by the standard HPLC method as a function of sodium cyanate concentration. As can be seen in FIG. 32, hemoglobin carbamylation caused little change in the percentage $HbA_{1c}$ measured by the direct binding immunoassay of the present invention, whereas percentage $HbA_{1c}$ measured by HPLC increased from 5.04% to 18.47 (a 3.66-fold increase). Thus, carbamylation does not interfere with the accurate measurement of $HbA_{1c}$ concentration by the immunoassay of the invention, and the immunoassay of the invention is clearly superior to HPLC in this regard.

We claim:

1. A method of preparing an antibody which specifically binds a protein which is non-enzymatically glycosylated on the alpha amino group of its N-terminal amino acid after the sugar on the N-terminal amino acid of the protein has been reduced, the method comprising immunizing an animal with a compound having the formula:

(Glc-ol-X-L)$_n$-carrier wherein,

X is the N-terminal amino acid of the non-enzymatically glycosylated protein, except that X cannot be lysine;

L is a bond or a linker group, provided that if L is an amino acid or peptide, the combination of X and L does not correspond to the N-terminal sequence of the glycosylated protein to which it is desired to form an antibody;

Glc-ol is the reduced form of the sugar that is attached to the alpha amino group of X on the glycosylated protein;

the carrier is an immunogenic compound other than the glycosylated protein; and n is from 1 to the number of available coupling sites on the carrier.

2. The method of claim 1 wherein the protein is glycosylated with glucose or a derivative.

3. The method of claim 2 wherein the glycosylated protein is hemoglobin.

4. The method of claim 3 wherein the glycosylated protein is $HbA_{1c}$, Glc-ol is glucitol and X is valine.

5. The method of claim 4 wherein L is glycine-glycine.

6. The method of claim 3 wherein the glycosylated protein is $HbA_{1c}$, Glc-ol is mannitol and X is valine.

7. The method of claim 6 wherein L is glycine-glycine.

8. An immunoassay for a protein that is non-enzymatically glycosylated on the alpha amino group of its N-terminal amino acid, the immunoassay comprising:

providing a sample containing the glycosylated protein;

reacting the glycosylated protein with a reducing agent so that the sugar residue on the N-terminal amino acid is reduced;

contacting the reduced glycosylated protein with an antibody which specifically binds Glc-ol-X wherein X is the N-terminal amino acid of the glycosylated protein, except that X cannot be lysine, and Glc-ol is the reduced form of the sugar attached to X on the glycosylated protein; and detecting or quantitating the reduced glycosylated protein bound to the antibody.

9. The method of claim 8 wherein the protein is glycosylated with glucose or a derivative.

10. The method of claim 9 wherein the glycosylated protein is hemoglobin.

11. The method of claim 10 wherein the glycosylated protein is $HbA_{1c}$, Glc-ol is glucitol and X is valine.

12. The method of claim 10 wherein the glycosylated protein is $HbA_{1c}$, Glc-ol is mannitol and X is valine.

13. The method of claim 10 wherein the sample is whole blood, and the blood is treated so as to lyse the red blood cells therein so as to release $HbA_{1c}$ from the cells.

14. The method of claim 13 further comprising the step of coating a solid surface with the released $HbA_{1c}$.

15. The method of claim 14 wherein the lysing and reducing steps are performed simultaneously.

16. The method of claim 14 wherein the lysing, reducing and coating steps are performed simultaneously.

17. The method of claim 13 wherein the $HbA_{1c}$ is detected or quantitated colorimetrically.

18. A kit for detecting or quantitating a protein that is non-enzymatically glycosylated on the alpha amino group of its N-terminal amino acid comprising:

a container of a first antibody which specifically binds Glc-ol-X, wherein X is the N-terminal amino acid of the glycosylated protein, except that X cannot be lysine, and Glc-ol is the reduced form of the sugar attached to X on the glycosylated protein.

19. The kit of claim 18 wherein the first antibody is labeled to allow for the detection or quantitation of the protein.

20. The kit of claim 18 further comprising a container of reducing agent for reducing the sugar residue on the alpha amino group of the N-terminal amino acid of the glycosylated protein.

21. The kit of claim 18 further comprising a container of a labeled component useful for detecting or quantitating reduced glycosylated protein bound to the first antibody.

22. The kit of claim 21 wherein the labeled component is a second antibody reactive with the first antibody.

23. The kit of claim 18 further comprising a container of a substance capable of lysing the red blood cells in a sample of whole blood so as to release the $HbA_{1c}$ contained therein.

24. Antibody which specifically binds Glc-ol-X, wherein X is the N-terminal amino acid of a non-enzymatically glycosylated protein, except that X cannot be lysine, and Glc-ol is the reduced form of the sugar residue attached to the alpha amino group of X on the glycosylated protein.

25. The antibody of claim 24 which is directed to glucitol-valine.

26. The antibody of claim 24 which is directed to mannitol-valine.

27. The antibody of claim 26 which is a monoclonal antibody.

28. The antibody of claim 27 which is an IgG1 antibody.

29. A hybridoma which produces monoclonal antibody which specifically binds mannitol-valine.

30. The hybridoma of claim 29 which produces antibody of the IgG1 class.

* * * * *

UNITED STATES PATENT AND TRADEMARK OFFICE
CERTIFICATE OF CORRECTION

PATENT NO. : 5,484,735
DATED : January 16, 1996
INVENTOR(S) : Lyman E. Davis et al.

It is certified that error appears in the above-indentified patent and that said Letters Patent is hereby corrected as shown below:

ON THE TITLE PAGE:
Item [56] References Cited:
On page 2, column 2, line 26, delete "Curtiss et al, J. Clin. Invest." and substitute --Curtiss et al., *J. Clin. Invest.*--

Signed and Sealed this

Twenty-eighth Day of October, 1997

Attest:

BRUCE LEHMAN

Attesting Officer

Commissioner of Patents and Trademarks